(12) United States Patent
Kunzer et al.

(10) Patent No.: US 8,338,466 B2
(45) Date of Patent: Dec. 25, 2012

(54) APOPTOSIS-INDUCING AGENTS FOR THE TREATMENT OF CANCER AND IMMUNE AND AUTOIMMUNE DISEASES

(75) Inventors: Aaron R. Kunzer, Arlington Heights, IL (US); Steven W. Elmore, Northbrook, IL (US); Laura A. Hexamer, Grayslake, IL (US); Cheol-Min Park, Singapore (SG); Andrew J. Souers, Evanston, IL (US); Gerard M. Sullivan, Lake Villa, IL (US); Gary T. Wang, Libertyville, IL (US); Xilu Wang, Grayslake, IL (US); Michael D. Wendt, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 201 days.

(21) Appl. No.: 12/689,133

(22) Filed: Jan. 18, 2010

(65) Prior Publication Data

US 2010/0184766 A1  Jul. 22, 2010

Related U.S. Application Data

(60) Provisional application No. 61/145,611, filed on Jan. 19, 2009.

(51) Int. Cl.
*C07D 277/00* (2006.01)
(52) U.S. Cl. ........ 514/369; 514/365; 514/359; 514/183; 548/183; 548/182; 548/146; 548/100
(58) Field of Classification Search ........................ None
See application file for complete search history.

(56) References Cited

U.S. PATENT DOCUMENTS

| | | | |
|---|---|---|---|
| 6,720,338 B2 | 4/2004 | Bruncko et al. | |
| 7,390,799 B2 | 6/2008 | Bruncko et al. | |
| 7,504,512 B2 | 3/2009 | Augeri et al. | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 7,642,260 B2 | 1/2010 | Bruncko et al. | |
| 7,754,886 B2 | 7/2010 | Augeri et al. | |
| 7,767,684 B2 | 8/2010 | Bruncko et al. | |
| 7,906,505 B2 | 3/2011 | Bruncko et al. | |
| 2007/0072860 A1 | 3/2007 | Bruncko et al. | |
| 2008/0076779 A1 | 3/2008 | Elmore et al. | |
| 2008/0182845 A1 | 7/2008 | Bardwell et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2010/0152183 A1 | 6/2010 | Bruncko et al. | |
| 2010/0160322 A1* | 6/2010 | Bruncko et al. | ........... 514/235.8 |
| 2010/0184750 A1 | 7/2010 | Hexamer et al. | |
| 2010/0298323 A1* | 11/2010 | Bruncko et al. | ........... 514/235.2 |

FOREIGN PATENT DOCUMENTS

| | | |
|---|---|---|
| WO | WO0224636 A2 | 3/2002 |
| WO | WO2004014913 A2 | 2/2004 |
| WO | WO2005032488 A2 | 4/2005 |
| WO | WO2005049593 A2 | 6/2005 |
| WO | WO2005049594 A1 | 6/2005 |
| WO | WO2008024337 A2 | 2/2008 |
| WO | WO2008/033747 | 3/2008 |
| WO | WO2009/036035 | 3/2009 |
| WO | WO2009/036051 | 3/2009 |

OTHER PUBLICATIONS

Beylot M., et al., "In vivo studies of intrahepatic metabolic pathways," Diabetes Metabolism, 1997, 23 (3), 251-257.
Blagojevic N., et al., "Role of heavy water In Boron Neutron Capture Therapy," in Topics in Dosimetry & Treatment Planning for Neutron Capture Therapy, Advanced Medical Publishing, Madison, WI, 1994, 125-134.
Blake et al., "Studies with deuterated drugs," J. Pharm. Sci., 1975, 64 (3), 367-391.
Brickner S. J., et al., "Synthesis and antibacterial activity of U-100592 and U-100766, two oxazolidinone antibacterial agents for the potential treatment of multidrug-resistant gram-positive bacterial infections," J Med Chem., 1996, 39 (3), 673-679.
Bruncko M., et al, "Studies leading to potent, dual inhibitors of Bcl-2 and Bcl-xL" Journal of Medicinal Chemistry, 2007, 50 (4), 641-662.
Czajka D. M., "Effect of deuterium oxide on the reproductive potential of mice," Ann NY Aced Sci, 1960, vol. 84, pp. 770-779.
Czajka D.M., et al., "Physiological effects of deuterium on dogs," Am. J. Physiol., 1961, 201 (2), 357-362.
Eliel, E. L. et al., "Stereochemistry of Organic Compounds," 1994, pp. 119-120, 1206, John Wiley & Sons, Inc. New York. Foster, A.B., et al., "Deuterium Isotope Effects in the Metabolism of Drugs and Xenobiotics: Implications for Drug Design," Advances in Drug Research, 1985, 14, Academic Press, London, 2-36.
Holzelova et al., "Autoimmune Lymphoproliferative Syndrome with Somatic Fas Mutations," New England Journal of Medicine, 2004, 351, pp. 1409-1418.
International Search Report for Application No. PCT/US2010/021243, mailed Jul. 13, 2010, 6 pages.
International Search Report for Publication No. PCT/US2010/021245, mailed Apr. 1, 2010, 3 pages.
IUPAC Commission on Nomenclature of Organic Chemistry: Rules for the Nomenclature of Organic Chemistry Section E: Stereochemistry, Pure Appl Chem, 1976, 45, 11-30.
Jones C.D et al., "Effects of Substituent Modification on Face Selection in Reduction," Journal Org. Chem, 1998, pp. 2758-2760, vol. 63.
Kato et al., "Synthesis of Deuterated Mosapride Citrate," J. Labelled Comp. Radiopharmaceut, 1995, 36 (10), 927-932.
Korolkova, A., "Essentials of Medicinal Chemistry," John Wiley-Interscience Publications, John Wiley & Sons, NemYork, pp. 97-118, 1988.

(Continued)

*Primary Examiner* — Anish Gupta
*Assistant Examiner* — Theodore R West
(74) *Attorney, Agent, or Firm* — Jones Day

(57) ABSTRACT

Disclosed are compounds which inhibit the activity of anti-apoptotic Bcl-2 proteins, compositions containing the compounds and methods of treating diseases during which is expressed anti-apoptotic Bcl-2 protein.

6 Claims, No Drawings

OTHER PUBLICATIONS

Kushner et al., "Pharmacological uses and perspectives of heavy water and deuterated compounds," Can J Physiol Pharmacol, 1999, vol. 77, pp. 79-88.

Lizondo J., et al., "Linezolid: Oxazolidinone antibacterial," Drugs of the Future, 1996, 21 (11), 1116-1123.

Mallesham B., et al., "Highly efficient CuI-catalyzed coupling of aryl bromides with oxazolidinones using Buchwald's protocol: a short route to linezolid and toloxatone," Org. Lett., 2003, 5 (7), 963-965.

Park C.M., et al., "Discovery of an orally bioavailable small molecule inhibitor of prosurvival B-cell lymphoma 2 proteins," Journal of Medicinal Chemistry, 2008, 51 (21), 6902-6915.

Puck, et al., "Immune Disorders Caused by Defects in the Caspase Cascade," Current Allergy and Asthma Reports, 2003, 3, pp. 378-384.

Rengan. et al., "Actin cytoskeletal function is spared, but apoptosis is increased, in WAS patient hematopoietic cells," Blood, 2000, 95—Issue 4, pp. 1283-1292.

Shimazaki et al., "Evaluation of apoptosis as a prognostic factor in myelodysplastic syndromes", British J Haematology, 2000, 110 Issue 3, pp. 584-590.

Sutton V.R., et al. "Bcl-2 prevents apoptosis induced by perforin and granzyme B, but not that mediated by whole cytotoxic lymphocytes", Journal of Immunology, 1997, 158 (12), pp. 5783-5790.

Thomson J. F., "Physiological effects of D20 in mammals," Ann. New York Acad. Sci., 1960, 84, 736-744.

Tse et al., "ABT-263: A Potent and Orally Bioavailable Bcl-2 Family Inhibitor," Cancer Research, 2008, 68 (9), pp. 3421-3428.

Wang Z.X., "An exact mathematical expression for describing competitive binding of two different ligands to a protein molecule", FEBS Lett, 1995; 360 (2): pp. 111-114.

\* cited by examiner

APOPTOSIS-INDUCING AGENTS FOR THE TREATMENT OF CANCER AND IMMUNE AND AUTOIMMUNE DISEASES

This application claims priority to U.S. Provisional Application Ser. No. 61/145,611, filed Jan. 19, 2009, which is incorporated by reference in its entirety.

FIELD OF THE INVENTION

This invention pertains to compounds which inhibit the activity of Bcl-2 anti-apoptotic proteins, compositions containing the compounds, and methods of treating diseases during which anti-apoptotic Bcl-2 proteins are expressed.

BACKGROUND OF THE INVENTION

Anti-apoptotic Bcl-2 proteins are associated with a number of diseases. There is therefore an existing need in the therapeutic arts for compounds which inhibit the activity of anti-apoptotic Bcl-2 proteins.

Overexpression of Bcl-2 proteins correlates with resistance to chemotherapy, clinical outcome, disease progression, overall prognosis or a combination thereof in various cancers and disorders of the immune system.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in *Current Allergy and Asthma Reports* 2003, 3, 378-384; *British Journal of Haematology* 2000, 110 (3), 584-90; *Blood* 2000, 95(4), 1283-92; and *New England Journal of Medicine* 2004, 351(14), 1409-1418. Involvement of Bcl-2 proteins in arthritis is disclosed in commonly-owned U.S. Provisional Patent Application Ser. No. 60/988,479. Involvement of Bcl-2 proteins in bone marrow transplant rejection is disclosed in commonly-owned U.S. patent application Ser. No. 11/941,196.

SUMMARY OF THE INVENTION

One embodiment of this invention, therefore, pertains to compounds or therapeutically acceptable salts, prodrugs, metabolites, or salts of prodrugs thereof, which are useful as inhibitors of anti-apoptotic Bcl-2 proteins, the compounds having Formula I

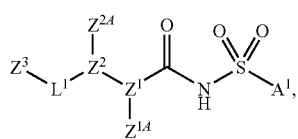

wherein $A^1$ is furyl, imidazolyl, isothiazolyl, isoxazolyl, oxadiazolyl, oxazolyl, pyrazinyl, pyrazolyl, pyridazinyl, 2-pyridinyl, 4-pyridinyl, pyrimidinyl, pyrrolyl, tetrazolyl, thiadiazolyl, thienyl, triazinyl, triazolyl, cycloalkyl, cycloalkenyl, heterocycloalkyl, or heterocycloalkenyl; each of which is unfused or fused with benzene, heteroarene or $A^{1A}$; $A^{1A}$ is cycloalkane, cycloalkene, heterocycloalkane, or heterocycloalkene;

wherein $A^1$ is unsubstituted or substituted with one or two or three or four or five independently selected $R^1$, $OR^1$, $SR^1$, $S(O)R^1$, $SO_2R^1$, $C(O)R^1$, $C(O)OR^1$, $OC(O)R^1$, $NHR^1$, $(R^1)_2$, $C(N)C(O)R^1$, $C(O)NHR^1$, $C(O)N(R^1)_2$, $C(O)NHOH$, $C(O)NHOR^1$, $C(O)NHSO_2R^1$, $NHC(O)R^1$, $NR^1C(O)R^1$, $NHC(O)OR^1$, $NR^1C(O)OR^1$, $NR^1C(O)NHR^1$, $NR^1C(O)N(R^1)_2$, $NHC(O)NH_2$, $NHC(O)NHR^1$, $NHC(O)N(R^1)_2$, $SO_2NH_2$, $SO_2NHR^1$, $SO_2N(R^1)_2$, $NHS(O)R^1$, $NHSO_2R^1$, $NR^1SO_2R^1$, $NHSO_2NHR^1$, $N(CH_3)SO_2N(CH_3)R^1$, (O), $NH_2$, $NO_2$, $N_3$, OH, F, Cl, Br, I, CN, $CF_3$, $OCF_3$, $CF_2CF_3$, $OCF_2CF_3$, $C(O)H$, $C(O)OH$, $C(N)NH_2$, $C(N)NHR^1$, $C(N)N(R^1)_2$, CNOH, $CNOCH_3$, $C(O)NH_2$ or $C(O)OR^{1A}$;

$R^1$ is $R^2$, $R^3$, $R^4$ or $R^5$;

$R^{1A}$ is cycloalkyl, cycloalkenyl or cycloalkynyl;

$R^2$ is phenyl, which is unfused or fused with benzene, heteroarene or $R^{2A}$; $R^{2A}$ is cycloalkane, cycloalkene, heterocycloalkane or heterocycloalkene;

$R^3$ is heteroaryl, which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl, which is unfused or fused with benzene, heteroarene or $R^{8A}$; $R^{8A}$ is cycloalkane, cycloalkene, heterocycloalkane or heterocycloalkene;

$R^9$ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl, or heterocycloalkenyl each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $SR^{12}$, $S(O)R^{12}$, $SO_2R^{12}$, $C(O)R^{12}$, $C(O)OR^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$Z^1$ is $R^{26}$ or $R^{27}$;

$Z^2$ is $R^{28}$, $R^{29}$ or $R^{30}$;

$Z^{1A}$ and $Z^{2A}$ are both absent or are taken together to form $CH_2$, $CH_2CH_2$ or $Z^{12A}$;

$Z^{12A}$ is $C_2$-$C_6$-alkylene having one or two $CH_2$ moieties replaced by $NH$, $N(CH_3)$, $S$, $S(O)$ or $SO_2$;

$L^1$ is a $R^{37}$, $OR^{37}$, $SR^{37}$, $S(O)R^{37}$, $SO_2R^{37}$, $C(O)R^{37}$, $C(O)OR^{37}$, $OC(O)R^{37}$, $OC(O)OR^{37}$, $NHR^{37}$, $C(O)NH$, $C(O)NR^{37}$, $C(O)NHOR^{37}$, $C(O)NHSO_2R^{37}$, $SO_2NH$, $SO_2NHR^{37}$, $C(N)NH$, $C(N)NHR^{37}$;

$R^{26}$ is phenylene which is unfused or fused with benzene or heteroarene or $R^{26A}$; $R^{26A}$ is cycloalkane, cycloalkene, heterocycloalkane or heterocycloalkene;

$R^{27}$ is heteroarylene, which is unfused or fused with benzene or heteroarene or $R^{27A}$; $R^{27A}$ is cycloalkane, cycloalkene, heterocycloalkane or heterocycloalkene;

$R^{28}$ is phenylene, which is unfused or fused with benzene, heteroarene or $R^{28A}$; $R^{28A}$ is cycloalkane, cycloalkene, heterocycloalkane or heterocycloalkene;

$R^{29}$ is heteroarylene, which is unfused or fused with benzene or heteroarene or $R^{29A}$; $R^{28A}$ is cycloalkane, cycloalkene, heterocycloalkane or heterocycloalkene;

$R^{30}$ is cycloalkylene, cycloalkenylene, heterocycloalkylene or heterocycloalkenylene, each of which is unfused or fused with benzene, heteroarene or $R^{30A}$; $R^{30A}$ is cycloalkane, cycloalkene, heterocycloalkane or heterocycloalkene;

$R^{37}$ is a bond or $R^{37A}$;

$R^{37A}$ is alkylene, alkenylene, or alkynylene, each of which is unsubstituted or substituted with one or two or three independently selected $R^{37B}$, $OR^{37B}$, $SR^{37B}$, $S(O)R^{37B}$, $SO_2R^{37B}$, $C(O)R^{37B}$, $C(O)OR^{37B}$, $OC(O)R^{37B}$, $OC(O)OR^{37B}$, $NH_2$, $NHR^{37B}$, $N(R^{37B})_2$, $NHC(O)R^{37B}$, $NR^{37B}C(O)R^{37B}$, $NHS(O)_2R^{37B}$, $NR^{37B}S(O)_2R^{37B}$, $NHC(O)OR^{37B}$, $NR^{37B}C(O)OR^{37B}$, $NHC(O)NH_2$, $NHC(O)NHR^{37B}$, $NHC(O)N(R^{37B})_2$, $NR^{37B}C(O)NHR^{37B}$, $NR^{37B}C(O)N(R^{37B})_2$, $C(O)NH_2$, $C(O)NHR^{37B}$, $C(O)N(R^{37B})_2$, $C(O)NHOH$, $C(O)NHOR^{37B}$, $C(O)NHSO_2R^{37B}$, $C(O)NR^{37B}SO_2R^{37B}$, $SO_2NH_2$, $SO_2NHR^{37B}$, $SO_2N(R^{37B})_2$, $C(O)H$, $C(O)OH$, $C(N)NH_2$, $C(N)NHR^{37B}$, $C(N)N(R^{37B})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{37B}$ is alkyl, alkenyl, alkynyl, phenyl, heteroaryl, cycloalkyl, cycloalkenyl, heterocycloalkyl, or heterocycloalkenyl;

$Z^3$ is $R^{38}$, $R^{39}$ or $R^{40}$;

$R^{38}$ is phenyl, which is unfused or fused with benzene, heteroarene or $R^{38A}$; $R^{38A}$ is cycloalkane, cycloalkene, heterocycloalkane or heterocycloalkene;

$R^{39}$ is heteroaryl, which is unfused or fused with benzene, heteroarene or $R^{39A}$; $R^{39A}$ is cycloalkane, cycloalkene, heterocycloalkane or heterocycloalkene;

$R^{40}$ is cycloalkyl, cycloalkenyl, heterocycloalkyl, or heterocycloalkenyl, each of which is unfused or fused with benzene, heteroarene or $R^{40A}$; $R^{40A}$ is cycloalkane, cycloalkene, heterocycloalkane or heterocycloalkene;

wherein the moieties represented by $R^{26}$ and $R^{27}$ are unsubstituted or substituted, (i.e., if $Z^{1A}$ and $Z^{2A}$ are absent) or further unsubstituted or further substituted (i.e., if $Z^{1A}$ and $Z^{2A}$ are present) with one or more $R^{41}$, $OR^{41}$, $SR^{41}$, $S(O)R^{41}$, $SO_2R^{41}$, $C(O)R^{41}$, $C(O)OR^{41}$, $OC(O)R^{41}$, $OC(O)OR^{41}$, $NH_2$, $NHR^{41}$, $N(R^{41})_2$, $NHC(O)R^{41}$, $NR^{41}C(O)R^{41}$, $NHS(O)_2R^{41}$, $NR^{41}S(O)_2R^{41}$, $NHC(O)OR^{41}$, $NR^{41}C(O)OR^{41}$, $NHC(O)NH_2$, $NHC(O)NHR^{41}$, $NHC(O)N(R^{41})_2$, $NR^{41}C(O)NHR^{41}$, $NR^{41}C(O)N(R^{41})_2$, $C(O)NH_2$, $C(O)NHR^{41}$, $C(O)N(R^{41})_2$, $C(O)NHOH$, $C(O)NHOR^{41}$, $C(O)NHSO_2R^{41}$, $C(O)NR^{41}SO_2R^{41}$, $SO_2NH_2$, $SO_2NHR^{41}$, $SO_2N(R^{41})_2$, $C(O)H$, $C(O)OH$, $C(N)NH_2$, $C(N)NHR^{41}$, $C(N)N(R^{41})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{41}$ is $R^{42}$, $R^{43}$, $R^{44}$ or $R^{45}$;

$R^{42}$ is phenyl, which is unfused or fused with benzene, heteroarene or $R^{42A}$; $R^{42A}$ is cycloalkane, cycloalkene, heterocycloalkane or heterocycloalkene;

$R^{43}$ is heteroaryl, which is unfused or fused with benzene, heteroarene or $R^{43A}$; $R^{43A}$ is cycloalkane, cycloalkene, heterocycloalkane or heterocycloalkene;

$R^{44}$ is cycloalkyl, cycloalkenyl, heterocycloalkyl, or heterocycloalkenyl, each of which is unfused or fused with benzene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $SR^{46}$, $S(O)R^{46}$, $SO_2R^{46}$, $C(O)R^{46}$, $C(O)OR^{46}$, $OC(O)R^{46}$, $OC(O)OR^{46}$, $NH_2$, $NHR^{46}$, $N(R^{46})_2$, $NHC(O)R^{46}$, $NR^{46}C(O)R^{46}$, $NHS(O)_2R^{46}$, $NR^{46}S(O)_2R^{46}$, $NHC(O)OR^{46}$, $NR^{46}C(O)OR^{46}$, $NHC(O)NH_2$, $NHC(O)NHR^{46}$, $NHC(O)N(R^{46})_2$, $NR^{46}C(O)NHR^{46}$, $NR^{46}C(O)N(R^{46})_2$, $C(O)NH_2$, $C(O)NHR^{46}$, $C(O)N(R^{46})_2$, $C(O)NHOH$, $C(O)NHOR^{46}$, $C(O)NHSO_2R^{46}$, $C(O)NR^{46}SO_2R^{46}$, $SO_2NH_2$, $SO_2NHR^{46}$, $SO_2N(R^{46})_2$, $C(O)H$, $C(O)OH$, $C(N)NH_2$, $C(N)NHR^{46}$, $C(N)N(R^{46})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{46}$ is alkyl, alkenyl, alkynyl, $R^{47}$, $R^{48}$ or $R^{49}$;

$R^{47}$ is phenyl, which is unfused or fused with benzene, heteroarene or $R^{47A}$; $R^{47A}$ is cycloalkane, cycloalkene, heterocycloalkane or heterocycloalkene;

$R^{48}$ is heteroaryl, which is unfused or fused with benzene, heteroarene or $R^{48A}$; $R^{48A}$ is cycloalkane, cycloalkene, heterocycloalkane or heterocycloalkene; $R^{49}$ is cycloalkyl, cycloalkenyl, heterocycloalkyl, or heterocycloalkenyl, each of which is unfused or fused with benzene, heteroarene or $R^{49A}$; $R^{49A}$ is cycloalkane, cycloalkene, heterocycloalkane or heterocycloalkene;

the moieties represented by $R^{42}$, $R^{43}$, $R^{44}$, $R^{47}$, $R^{48}$ and $R^{49}$ are independently unsubstituted or substituted with one or more independently selected $R^{50}$, $OR^{50}$, $SR^{50}$, $S(O)R^{50}$, $SO_2R^{50}$, $C(O)R^{50}$, $C(O)OR^{50}$, $OC(O)R^{50}$, $OC(O)OR^{50}$, $NH_2$, $NHR^{50}$, $N(R^{50})_2$, $NHC(O)R^{50}$, $NR^{50}C(O)R^{50}$, $NHS(O)_2R^{50}$, $NR^{50}S(O)_2R^{50}$, $NHC(O)OR^{50}$, $NR^{50}C(O)OR^{50}$, $NHC(O)NH_2$, $NHC(O)NHR^{50}$, $NHC(O)N(R^{50})_2$, $NR^{50}C(O)NHR^{50}$, $NR^{50}C(O)N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{50}SO_2R^{50}$, $SO_2NH_2$, $SO_2NHR^{50}$, $SO_2N(R^{50})_2$, $C(O)H$, $C(O)OH$, $C(N)NH_2$, $C(N)NHR^{50}$, $C(N)N(R^{50})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{50}$ is $R^{51}$, $R^{52}$, $R^{53}$ or $R^{54}$;

$R^{51}$ is phenyl, which is unfused or fused with benzene, heteroarene or $R^{51A}$; $R^{51A}$ is cycloalkane, cycloalkene, heterocycloalkane or heterocycloalkene;

$R^{52}$ is heteroaryl, which is unfused or fused with benzene, heteroarene or $R^{52A}$; $R^{52A}$ is cycloalkane, cycloalkene, heterocycloalkane or heterocycloalkene;

$R^{53}$ is cycloalkyl, cycloalkenyl, heterocycloalkyl, or heterocycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $C(O)R^{55}$, $C(O)OR^{55}$, $OC(O)R^{55}$, $OC(O)OR^{55}$, $NH_2$, $NHR^{55}$, $N(R^{55})_2$, $NHC(O)R^{55}$, $NR^{55}C(O)R^{55}$, $NHS(O)_2R^{55}$, $NR^{55}S(O)_2R^{55}$, $NHC(O)OR^{55}$, $NR^{55}C(O)OR^{55}$, $NHC(O)NH_2$, $NHC(O)NHR^{55}$, $NHC(O)N(R^{55})_2$, $NR^{55}C(O)NHR^{55}$, $NR^{55}C(O)N(R^{55})_2$, $C(O)NH_2$, $C(O)NHR^{55}$, $C(O)N(R^{55})_2$, $C(O)NHOH$, $C(O)NHOR^{55}$, $C(O)NHSO_2R^{55}$, $C(O)NR^{55}SO_2R^{55}$, $SO_2NH_2$, $SO_2NHR^{55}$, $SO_2N(R^{55})_2$, $C(O)H$, $C(O)OH$, $C(N)NH_2$, $C(N)NHR^{55}$, $C(N)N(R^{55})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{55}$ is alkyl, alkenyl, alkynyl, phenyl, heteroaryl, cycloalkyl, cycloalkenyl, heterocycloalkyl, or heterocycloalkenyl;

wherein each foregoing cyclic moiety is independently unsubstituted, further unsubstituted, substituted or further substituted with one or more independently selected $R^{57}$, $OR^{57}$, $SR^{57}$, $S(O)R^{57}$, $SO_2R^{57}$, $C(O)R^{57}$, $C(O)OR^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl, or alkynyl, each of which is unsubstituted or substituted with one or two or three independently selected $R^{62}$, $OR^{62}$, $SR^{62}$, $S(O)R^{62}$, $SO_2R^{62}$, $C(O)R^{62}$, $C(O)OR^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl, or alkenyl, each of which is unsubstituted or substituted with one or two or three independently selected $R^{67}$, $OR^{67}$, $SR^{67}$, $S(O)R^{67}$, $SO_2R^{67}$, $C(O)R^{67}$, $C(O)OR^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the moieties represented by $R^{58}$, $R^{59}$, $R^{60}$, $R^{63}$, $R^{64}$, $R^{65}$, and $R^{67}$ are unsubstituted or substituted with one or more independently selected $R^{68}$, $OR^{68}$, $SR^{68}$, $S(O)R^{68}$, $SO_2R^{68}$, $C(O)R^{68}$, $C(O)OR^{68}$, $OC(O)R^{68}$, $OC(O)OR^{68}$, $NH_2$, $NHR^{68}$, $N(R^{68})_2$, $NHC(O)R^{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{68}$ is $R^{69}$, $R^{70}$, $R^{71}$ or $R^{72}$;

$R^{69}$ is phenyl, which is unfused or fused with benzene, heteroarene or $R^{69A}$; $R^{69A}$ is cycloalkane, cycloalkene, heterocycloalkane or heterocycloalkene;

$R^{70}$ is heteroaryl, which is unfused or fused with benzene, heteroarene or $R^{70A}$; $R^{70A}$ is cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with benzene, heteroarene or $R^{71A}$; $R^{71A}$ is cycloalkane, cycloalkene, heterocycloalkane or heterocycloalkene;

$R^{72}$ is alkyl, alkenyl, or alkenyl, each of which is unsubstituted or substituted with one or two or three independently selected $R^{73}$, $OR^{73}$, $SR^{73}$, $S(O)R^{73}$, $SO_2R^{73}$, $C(O)R^{73}$, $C(O)OR^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, $NHC(O)N(R^{73})_2$, $NR^{73}C(O)NHR^{73}$, $NR^{73}C(O)N(R^{73})_2$, $C(O)NH_2$, $C(O)NHR^{73}$, $C(O)N(R^{73})_2$, $C(O)NHOH$, $C(O)NHOR^{73}$, $C(O)NHSO_2R^{73}$, $C(O)NR^{73}SO_2R^{73}$, $SO_2NH_2$, $SO_2NHR^{73}$, $SO_2N(R^{73})_2$, $C(O)H$, $C(O)OH$, $C(N)NH_2$, $C(N)NHR^{73}$, $C(N)N(R^{73})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{73}$ is alkyl, alkenyl, alkenyl, phenyl, heteroaryl, cycloalkyl, cycloalkenyl, heterocycloalkyl, or heterocycloalkenyl; and the moieties represented by $R^{69}$, $R^{70}$, and $R^{71}$ are unsubstituted or substituted with one or more independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents.

In another embodiment of Formula (I), $A^1$ is furyl, imidazolyl, isothiazolyl, isoxazolyl, pyrazolyl, pyrrolyl, thiazolyl, thiadiazolyl, thienyl, triazolyl, heterocycloalkyl, or heterocycloalkenyl; each of which is unfused or fused with benzene, heteroarene or $A^{1A}$; $A^{1A}$ is heterocycloalkene;

wherein $A^1$ is unsubstituted or substituted with one or two or three or four or five independently selected $R^1$, $OR^1$, $C(O)OR^1$, $NHR^1$, $N(R^1)_2$, $C(N)C(O)R^1$, $C(O)NHR^1$, $NHC(O)R^1$, $NR^1C(O)R^1$, $(O)$, $NO_2$, $F$, $Cl$, $Br$, $I$, $CF_3$;

$R^1$ is $R^2$, $R^3$, $R^4$ or $R^5$;

$R^2$ is phenyl;

$R^3$ is heteroaryl;

$R^4$ is heterocycloalkyl;

$R^5$ is alkyl, or alkenyl, each of which is unsubstituted or substituted $R^7$, $SR^7$, $N(R^7)_2$, $NHC(O)R^7$, $F$, $Cl$, $Br$ or $I$ substituents;

$R^7$ is $R^8$, $R^9$, $R^{10}$ or $R^{11}$;

$R^8$ is phenyl;

$R^9$ is heteroaryl;

$R^{10}$ is heterocycloalkyl;

$R^{11}$ is alkyl;

$Z^1$ is $R^{26}$;

$Z^2$ is $R^{30}$;

$L^1$ is a $R^{37}$;

$R^{26}$ is phenylene;

$R^{30}$ is heterocycloalkylene;

$R^{37}$ is $R^{37A}$;

$R^{37A}$ is alkylene, or alkenylene, each of which is unsubstituted or substituted with $R^{37B}$;

$R^{37B}$ is phenyl;

$Z^3$ is $R^{38}$, or $R^{40}$;

$R^{38}$ is phenyl;

$R^{40}$ is cycloalkyl, or cycloalkenyl;

wherein the moieties represented by $R^{26}$ and $R^{27}$ are unsubstituted or substituted with $OR^{41}$;

$R^{41}$ is $R^{42}$, or $R^{43}$;

$R^{42}$ is phenyl, which is unfused or fused with heteroarene;

$R^{43}$ is heteroaryl, which is unfused or fused with heteroarene;

wherein each foregoing cyclic moiety is independently unsubstituted, further unsubstituted, substituted or further substituted with one or more independently selected $R^{57}$, $OR^{57}$, $C(O)OR^{57}$, $F$, $Cl$, $Br$ or $I$ substituents;

$R^{57}$ is $R^{58}$, or $R^{61}$;

$R^{58}$ is phenyl;

$R^{61}$ is alkyl; and wherein the moieties represented by $R^{58}$, are unsubstituted or substituted with one or more independently selected $F$, $Cl$, $Br$ or $I$ substituents.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula II

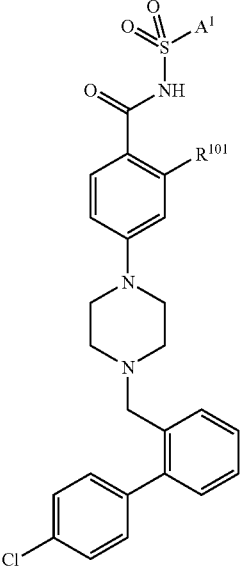

(II)

wherein $A^1$ is furyl, imidazolyl, isothiazolyl, isoxazolyl, oxadiazolyl, oxazolyl, pyrazinyl, pyrazolyl, pyridazinyl, 2-pyridinyl, 4-pyridinyl, pyrimidinyl, pyrrolyl, tetrazolyl, thiazolyl, thiadiazolyl, thienyl, triazinyl, triazolyl, cycloalkyl, cycloalkenyl, heterocycloalkyl, or heterocycloalkenyl; each of which is unfused or fused with benzene, heteroarene or $A^{1A}$; $A^{1A}$ is cycloalkane, cycloalkene, heterocycloalkane, or heterocycloalkene;

wherein $A^1$ is unsubstituted or substituted with one or two or three or four or five independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(N)C(O)R^1$, $C(O)NHR^1$, $C(O)N(R^1)_2$, $C(O)NHOH$, $C(O)NHOR^1$, $C(O)NHSO_2R^1$, $NHC(O)R^1$, $NR^1C(O)R^1$, $NHC(O)OR^1$, $NR^1C(O)OR^1$, $NR^1C(O)NHR^1$, $NR^1C(O)N(R^1)_2$, $NHC(O)NH_2$, $NHC(O)NHR^1$, $NHC(O)N(R^1)_2$, $SO_2NH_2$, $SO_2NHR^1$, $SO_2N(R^1)_2$, $NHS(O)R^1$, $NHSO_2R^1$, $NR^1SO_2R^1$, $NHSO_2NHR^1$, $N(CH_3)SO_2N(CH_3)R^1$, $(O)$, $NH_2$, $NO_2$, $N_3$, $OH$, $F$, $Cl$, $Br$, $I$, $CN$, $CF_3$, $OCF_3$, $CF_2CF_3$, $OCF_2CF_3$, $C(O)H$, $C(O)OH$, $C(N)NH_2$, $C(N)NHR^1$, $C(N)N(R^1)_2$, $CNOH$, $CNOCH_3$, $C(O)NH_2$ or $C(O)OR^{1A}$;

$R^1$ is $R^2$, $R^3$, $R^4$ or $R^5$;

$R^{1A}$ is cycloalkyl, cycloalkenyl or cycloalkynyl;

$R^2$ is phenyl, which is unfused or fused with benzene, heteroarene or $R^{2A}$; $R^{2A}$ is cycloalkane, cycloalkene, heterocycloalkane or heterocycloalkene;

$R^3$ is heteroaryl, which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, $OH$, $(O)$, $C(O)OH$, $(O)$, $N_3$, $CN$, $NH_2$, $CF_3$, $CF_2CF_3$, $F$, $Cl$, $Br$ or $I$ substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl, which is unfused or fused with benzene, heteroarene or $R^{8A}$; $R^{8A}$ is cycloalkane, cycloalkene, heterocycloalkane or heterocycloalkene;

$R^9$ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl, or heterocycloalkenyl each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $SR^{12}$, $S(O)R^{12}$, $SO_2R^{12}$, $C(O)R^{12}$, $C(O)OR^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, C(O)H, C(O)OH, $C(N)NH_2$, $C(N)NHR^{12}$, $C(N)N(R^{12})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

wherein the moiety represented by $R^{101}$ is H, $R^{41}$, $OR^{41}$, $SR^{41}$, $S(O)R^{41}$, $SO_2R^{41}$, $C(O)R^{41}$, $C(O)OR^{41}$, $OC(O)R^{41}$, $OC(O)OR^{41}$, $NH_2$, $NHR^{41}$, $N(R^{41})_2$, $NHC(O)R^{41}$, $NR^{41}C(O)R^{41}$, $NHS(O)_2R^{41}$, $NR^{41}S(O)_2R^{41}$, $NHC(O)OR^{41}$, $NR^{41}C(O)OR^{41}$, $NHC(O)NH_2$, $NHC(O)NHR^{41}$, $NHC(O)N(R^{41})_2$, $NR^{41}C(O)NHR^{41}$, $NR^{41}C(O)N(R^{41})_2$, $C(O)NH_2$, $C(O)NHR^{41}$, $C(O)N(R^{41})_2$, $C(O)NHOH$, $C(O)NHOR^{41}$, $C(O)NHSO_2R^{41}$, $C(O)NR^{41}SO_2R^{41}$, $SO_2NH_2$, $SO_2NHR^{41}$, $SO_2N(R^{41})_2$, C(O)H, C(O)OH, $C(N)NH_2$, $C(N)NHR^{41}$, $C(N)N(R^{41})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{41}$ is $R^{42}$, $R^{43}$, $R^{44}$ or $R^{45}$;

$R^{42}$ is phenyl, which is unfused or fused with benzene, heteroarene or $R^{42A}$; $R^{42A}$ is cycloalkane, cycloalkene, heterocycloalkane or heterocycloalkene;

$R^{43}$ is heteroaryl, which is unfused or fused with benzene, heteroarene or $R^{43A}$; $R^{43A}$ is cycloalkane, cycloalkene, heterocycloalkane or heterocycloalkene;

$R^{44}$ is cycloalkyl, cycloalkenyl, heterocycloalkyl, or heterocycloalkenyl, each of which is unfused or fused with benzene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $SR^{46}$, $S(O)R^{46}$, $SO_2R^{46}$, $C(O)R^{46}$, $C(O)OR^{46}$, $OC(O)R^{46}$, $OC(O)OR^{46}$, $NH_2$, $NHR^{46}$, $N(R^{46})_2$, $NHC(O)R^{46}$, $NR^{46}C(O)R^{46}$, $NHS(O)_2R^{46}$, $NR^{46}S(O)_2R^{46}$, $NHC(O)OR^{46}$, $NR^{46}C(O)OR^{46}$, $NHC(O)NH_2$, $NHC(O)NHR^{46}$, $NHC(O)N(R^{46})_2$, $NR^{46}C(O)NHR^{46}$, $NR^{46}C(O)N(R^{46})_2$, $C(O)NH_2$, $C(O)NHR^{46}$, $C(O)N(R^{46})_2$, $C(O)NHOH$, $C(O)NHOR^{46}$, $C(O)NHSO_2R^{46}$, $C(O)NR^{46}SO_2R^{46}$, $SO_2NH_2$, $SO_2NHR^{46}$, $SO_2N(R^{46})_2$, C(O)H, C(O)OH, $C(N)NH_2$, $C(N)NHR^{46}$, $C(N)N(R^{46})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{46}$ is alkyl, alkenyl, alkynyl, $R^{47}$, $R^{48}$ or $R^{49}$;

$R^{47}$ is phenyl, which is unfused or fused with benzene, heteroarene or $R^{47A}$; $R^{47A}$ is cycloalkane, cycloalkene, heterocycloalkane or heterocycloalkene;

$R^{48}$ is heteroaryl, which is unfused or fused with benzene, heteroarene or $R^{48A}$; $R^{48A}$ is cycloalkane, cycloalkene, heterocycloalkane or heterocycloalkene;

$R^{49}$ is cycloalkyl, cycloalkenyl, heterocycloalkyl, or heterocycloalkenyl, each of which is unfused or fused with benzene, heteroarene or $R^{49A}$; $R^{49A}$ is cycloalkane, cycloalkene, heterocycloalkane or heterocycloalkene;

the moieties represented by $R^{42}$, $R^{43}$, $R^{44}$, $R^{47}$, $R^{48}$, and $R^{49}$ are independently unsubstituted or substituted with one or more independently selected $R^{50}$, $OR^{50}$, $SR^{50}$, $S(O)R^{50}$, $SO_2R^{50}$, $C(O)R^{50}$, $C(O)OR^{50}$, $OC(O)R^{50}$, $OC(O)OR^{50}$, $NH_2$, $NHR^{50}$, $N(R^{50})_2$, $NHC(O)R^{50}$, $NR^{50}C(O)R^{50}$, $NHS(O)_2 R^{50}$, $NR^{50}S(O)_2R^{50}$, $NHC(O)OR^{50}$, $NR^{50}C(O)OR^{50}$, $NHC(O)NH_2$, $NHC(O)NHR^{50}$, $NHC(O)N(R^{50})_2$, $NR^{50}C(O)NHR^{50}$, $NR^{50}C(O)N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{50}SO_2R^{50}$, $SO_2NH_2$, $SO_2NHR^{50}$, $SO_2N(R^{50})_2$, C(O)H, C(O)OH, $C(N)NH_2$, $C(N)NHR^{50}$, $C(N)N(R^{50})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl, which is unfused or fused with benzene, heteroarene or $R^{51A}$; $R^{51A}$ is cycloalkane, cycloalkene, heterocycloalkane or heterocycloalkene;

$R^{52}$ is heteroaryl, which is unfused or fused with benzene, heteroarene or $R^{52A}$; $R^{52A}$ is cycloalkane, cycloalkene, heterocycloalkane or heterocycloalkene;

$R^{53}$ is cycloalkyl, cycloalkenyl, heterocycloalkyl, or heterocycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $C(O)R^{55}$, $C(O)OR^{55}$, $OC(O)R^{55}$, $OC(O)OR^{55}$, $NH_2$, $NHR^{55}$, $N(R^{55})_2$, $NHC(O)R^{55}$, $NR^{55}C(O)R^{55}$, $NHS(O)_2R^{55}$, $NR^{55}S(O)_2R^{55}$, $NHC(O)OR^{55}$, $NR^{55}C(O)OR^{55}$, $NHC(O)NH_2$, $NHC(O)NHR^{55}$, $NHC(O)N(R^{55})_2$, $NR^{55}C(O)NHR^{55}$, $NR^{55}C(O)N(R^{55})_2$, $C(O)NH_2$, $C(O)NHR^{55}$, $C(O)N(R^{55})_2$, $C(O)NHOH$, $C(O)NHOR^{55}$, $C(O)NHSO_2R^{55}$, $C(O)NR^{55}SO_2R^{55}$, $SO_2NH_2$, $SO_2NHR^{55}$, $SO_2N(R^{55})_2$, C(O)H, C(O)OH, $C(N)NH_2$, $C(N)NHR^{55}$, $C(N)N(R^{55})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{55}$ is alkyl, alkenyl, alkynyl, phenyl, heteroaryl, cycloalkyl, cycloalkenyl, heterocycloalkyl, or heterocycloalkenyl;

wherein each foregoing cyclic moiety is independently unsubstituted, further unsubstituted, substituted or further substituted with one or more independently selected $R^{57}$, OR$^{57}$, SR$^{57}$, S(O)R$^{57}$, SO$_2$R$^{57}$, C(O)R$^{57}$, C(O)OR$^{57}$, OC(O)R$^{57}$, OC(O)OR$^{57}$, NH$_2$, NHR$^{57}$, N(R$^{57}$)$_2$, NHC(O)R$^{57}$, NR$^{57}$C(O)R$^{57}$, NHS(O)$_2$R$^{57}$, NR$^{57}$S(O)$_2$R$^{57}$, NHC(O)OR$^{57}$, NR$^{57}$C(O)OR$^{57}$, NHC(O)NH$_2$, NHC(O)NHR$^{57}$, NHC(O)N(R$^{57}$)$_2$, NR$^{57}$C(O)NHR$^{57}$, NR$^{57}$C(O)N(R$^{57}$)$_2$, C(O)NH$_2$, C(O)NHR$^{57}$, C(O)N(R$^{57}$)$_2$, C(O)NHOH, C(O)NHOR$^{57}$, C(O)NHSO$_2$R$^{57}$, C(O)NR$^{57}$SO$_2$R$^{57}$, SO$_2$NH$_2$, SO$_2$NHR$^{57}$, SO$_2$N(R$^{57}$)$_2$, C(O)H, C(O)OH, C(N)NH$_2$, C(N)NHR$^{57}$, C(N)N(R$^{57}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{57}$ is R$^{58}$, R$^{59}$, R$^{60}$ or R$^{61}$;

R$^{58}$ is phenyl, which is unfused or fused with benzene, heteroarene or R$^{58A}$; R$^{58A}$ is cycloalkane, cycloalkene, heterocycloalkane or heterocycloalkene;

R$^{59}$ is heteroaryl, which is unfused or fused with benzene, heteroarene or R$^{59A}$; R$^{59A}$ is cycloalkane, cycloalkene, heterocycloalkane or heterocycloalkene;

R$^{60}$ is cycloalkyl, cycloalkenyl, heterocycloalkyl or heterocycloalkenyl, each of which is unfused or fused with benzene, heteroarene or R$^{60A}$; R$^{60A}$ is cycloalkane, cycloalkene, heterocycloalkane or heterocycloalkene;

R$^{61}$ is alkyl, alkenyl, or alkynyl, each of which is unsubstituted or substituted with one or two or three independently selected R$^{62}$, OR$^{62}$, SR$^{62}$, S(O)R$^{62}$, SO$_2$R$^{62}$, C(O)R$^{62}$, C(O)OR$^{62}$, OC(O)R$^{62}$, OC(O)OR$^{62}$, NH$_2$, NHR$^{62}$, N(R$^{62}$)$_2$, NHC(O)R$^{62}$, NR$^{62}$C(O)R$^{62}$, NHS(O)$_2$R$^{62}$, NR$^{62}$S(O)$_2$R$^{62}$, NHC(O)OR$^{62}$, NR$^{62}$C(O)OR$^{62}$, NHC(O)NH$_2$, NHC(O)NHR$^{62}$, NHC(O)N(R$^{62}$)$_2$, NR$^{62}$C(O)NHR$^{62}$, NR$^{62}$C(O)N(R$^{62}$)$_2$, C(O)NH$_2$, C(O)NHR$^{62}$, C(O)N(R$^{62}$)$_2$, C(O)NHOH, C(O)NHOR$^{62}$, C(O)NHSO$_2$R$^{62}$, C(O)NR$^{62}$SO$_2$R$^{62}$, SO$_2$NH$_2$, SO$_2$NHR$^{62}$, SO$_2$N(R$^{62}$)$_2$, C(O)H, C(O)OH, C(N)NH$_2$, C(N)NHR$^{62}$, C(N)N(R$^{62}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{62}$ is R$^{63}$, R$^{64}$, R$^{65}$ or R$^{66}$;

R$^{63}$ is phenyl, which is unfused or fused with benzene, heteroarene or R$^{63A}$; R$^{63A}$ is cycloalkane, cycloalkene, heterocycloalkane or heterocycloalkene;

R$^{64}$ is heteroaryl, which is unfused or fused with benzene, heteroarene or R$^{64A}$; R$^{64A}$ is cycloalkane, cycloalkene, heterocycloalkane or heterocycloalkene;

R$^{65}$ is cycloalkyl, cycloalkenyl, heterocycloalkyl or heterocycloalkenyl, each of which is unfused or fused with benzene, heteroarene or R$^{65A}$; R$^{65A}$ is cycloalkane, cycloalkene, heterocycloalkane or heterocycloalkene;

R$^{66}$ is alkyl, alkenyl, or alkenyl, each of which is unsubstituted or substituted with one or two or three independently selected R$^{67}$, OR$^{67}$, SR$^{67}$, S(O)R$^{67}$, SO$_2$R$^{67}$, C(O)R$^{67}$, C(O)OR$^{67}$, OC(O)R$^{67}$, OC(O)OR$^{67}$, NH$_2$, NHR$^{67}$, N(R$^{67}$)$_2$, NHC(O)R$^{67}$, NR$^{67}$C(O)R$^{67}$, NHS(O)$_2$R$^{67}$, NR$^{67}$S(O)$_2$R$^{67}$, NHC(O)OR$^{67}$, NR$^{67}$C(O)OR$^{67}$, NHC(O)NH$_2$, NHC(O)NHR$^{67}$, NHC(O)N(R$^{67}$)$_2$, NR$^{67}$C(O)NHR$^{67}$, NR$^{67}$C(O)N(R$^{67}$)$_2$, C(O)NH$_2$, C(O)NHR$^{67}$, C(O)N(R$^{67}$)$_2$, C(O)NHOH, C(O)NHOR$^{67}$, C(O)NHSO$_2$R$^{67}$, C(O)NR$^{67}$SO$_2$R$^{67}$, SO$_2$NH$_2$, SO$_2$NHR$^{67}$, SO$_2$N(R$^{67}$)$_2$, C(O)H, C(O)OH, C(N)NH$_2$, C(N)NHR$^{67}$, C(N)N(R$^{67}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{67}$ is alkyl, alkenyl, alkynyl, phenyl, heteroaryl, cycloalkyl, cycloalkenyl, heterocycloalkyl or heterocycloalkenyl;

wherein the moieties represented by R$^{58}$, R$^{59}$, R$^{60}$, R$^{63}$, R$^{64}$, R$^{65}$, and R$^{67}$ are unsubstituted or substituted with one or more independently selected R$^{68}$, OR$^{68}$, SR$^{68}$, S(O)R$^{68}$, SO$_2$R$^{68}$, C(O)R$^{68}$, C(O)OR$^{68}$, OC(O)R$^{68}$, OC(O)OR$^{68}$, NH$_2$, NHR$^{68}$, N(R$^{68}$)$_2$, NHC(O)R$^{68}$, NR$^{68}$C(O)R$^{68}$, NHS(O)$_2$R$^{68}$, NR$^{68}$S(O)$_2$R$^{68}$, NHC(O)OR$^{68}$, NR$^{68}$C(O)OR$^{68}$, NHC(O)NH$_2$, NHC(O)NHR$^{68}$, NHC(O)N(R$^{68}$)$_2$, NR$^{68}$C(O)NHR$^{68}$, NR$^{68}$C(O)N(R$^{68}$)$_2$, C(O)NH$_2$, C(O)NHR$^{68}$, C(O)N(R$^{68}$)$_2$, C(O)NHOH, C(O)NHOR$^{68}$, C(O)NHSO$_2$R$^{68}$, C(O)NR$^{68}$SO$_2$R$^{68}$, SO$_2$NH$_2$, SO$_2$NHR$^{68}$, SO$_2$N(R$^{68}$)$_2$, C(O)H, C(O)OH, C(N)NH$_2$, C(N)NHR$^{68}$, C(N)N(R$^{68}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{68}$ is R$^{69}$; R$^{70}$; R$^{71}$ or R$^{72}$;

R$^{69}$ is phenyl, which is unfused or fused with benzene, heteroarene or R$^{69A}$; R$^{69A}$ is cycloalkane, cycloalkene, heterocycloalkane or heterocycloalkene;

R$^{70}$ is heteroaryl, which is unfused or fused with benzene, heteroarene or R$^{70A}$; R$^{70A}$ is cycloalkane, cycloalkene, heterocycloalkane or heterocycloalkene;

R$^{71}$ is cycloalkyl, cycloalkenyl, heterocycloalkyl or heterocycloalkenyl, each of which is unfused or fused with benzene, heteroarene or R$^{71A}$; R$^{71A}$ is cycloalkane, cycloalkene, heterocycloalkane or heterocycloalkene;

R$^{72}$ is alkyl, alkenyl, or alkenyl, each of which is unsubstituted or substituted with one or two or three independently selected R$^{73}$, OR$^{73}$, SR$^{73}$, S(O)R$^{73}$, SO$_2$R$^{73}$, C(O)R$^{73}$, C(O)OR$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)NH$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO$_2$NH$_2$, SO$_2$NHR$^{73}$, SO$_2$N(R$^{73}$)$_2$, C(O)H, C(O)OH, C(N)NH$_2$, C(N)NHR$^{73}$, C(N)N(R$^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{73}$ is alkyl, alkenyl, alkenyl, phenyl, heteroaryl, cycloalkyl, cycloalkenyl, heterocycloalkyl, or heterocycloalkenyl; and the moieties represented by R$^{69}$, R$^{70}$, and R$^{71}$ are unsubstituted or substituted with one or more independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, CF$_3$, CF$_2$CF$_3$, OCF$_3$, OCF$_2$CF$_3$, F, Cl, Br or I substituents.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula III

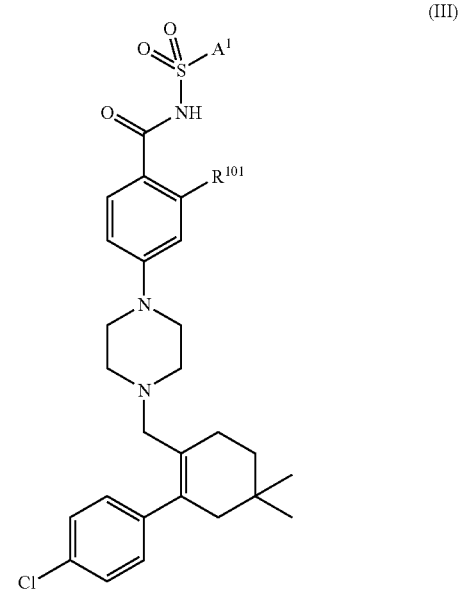

(III)

wherein

A¹ is furyl, imidazolyl, isothiazolyl, isoxazolyl, oxadiazolyl, oxazolyl, pyrazinyl, pyrazolyl, pyridazinyl, 2-pyridinyl, 4-pyridinyl, pyrimidinyl, pyrrolyl, tetrazolyl, thiazolyl, thiadiazolyl, thienyl, triazinyl, triazolyl, cycloalkyl, cycloalkenyl, heterocycloalkyl, or heterocycloalkenyl; each of which is unfused or fused with benzene, heteroarene or $A^{1.4}$; $A^{1.4}$ is cycloalkane, cycloalkene, heterocycloalkane, or heterocycloalkene;

wherein A¹ is unsubstituted or substituted with one or two or three or four or five independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(N)C(O)R^1$, $C(O)NHR^1$, $C(O)N(R^1)_2$, $C(O)NHOH$, $C(O)NHOR^1$, $C(O)NHSO_2R^1$, $NHC(O)R^1$, $NR^1C(O)R^1$, $NHC(O)OR^1$, $NR^1C(O)OR^1$, $NR^1C(O)NHR^1$, $NR^1C(O)N(R^1)_2$, $NHC(O)NH_2$, $NHC(O)NHR^1$, $NHC(O)N(R^1)_2$, $SO_2NH_2$, $SO_2NHR^1$, $SO_2N(R^1)_2$, $NHS(O)R^1$, $NHSO_2R^1$, $NR^1SO_2R^1$, $NHSO_2NHR^1$, $N(CH_3)SO_2N(CH_3)R^1$, (O), $NH_2$, $NO_2$, $N_3$, OH, F, Cl, Br, I, CN, $CF_3$, $OCF_3$, $CF_2CF_3$, $OCF_2CF_3$, C(O)H, C(O)OH, $C(N)NH_2$, $C(N)NHR^1$, $C(N)N(R^1)_2$, CNOH, $CNOCH_3$, $C(O)NH_2$ or $C(O)OR^{1.4}$;

$R^1$ is $R^2$, $R^3$, $R^4$ or $R^5$;

$R^{1.4}$ is cycloalkyl, cycloalkenyl or cycloalkynyl;

$R^2$ is phenyl, which is unfused or fused with benzene, heteroarene or $R^{2.4}$; $R^{2.4}$ is cycloalkane, cycloalkene, heterocycloalkane or heterocycloalkene;

$R^3$ is heteroaryl, which is unfused or fused with benzene, heteroarene or $R^{3.4}$; $R^{3.4}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4.4}$; $R^{4.4}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6.4})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6.4}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl, which is unfused or fused with benzene, heteroarene or $R^{8.4}$; $R^{8.4}$ is cycloalkane, cycloalkene, heterocycloalkane or heterocycloalkene;

$R^9$ is heteroaryl, which is unfused or fused with benzene, heteroarene or $R^{9.4}$; $R^{9.4}$ is cycloalkane, cycloalkene, heterocycloalkane or heterocycloalkene;

$R^{10}$ is cycloalkyl, cycloalkenyl, heterocycloalkyl, or heterocycloalkenyl each of which is unfused or fused with benzene, heteroarene or $R^{10.4}$; $R^{10.4}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $SR^{12}$, $S(O)R^{12}$, $SO_2R^{12}$, $C(O)R^{12}$, $C(O)OR^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, C(O)H, C(O)OH, $C(N)NH_2$, $C(N)NHR^{12}$, $C(N)N(R^{12})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{12}$ is $R^{13}$, $R^{14}$, $R^{15}$ or $R^{16}$;

$R^{13}$ is phenyl, which is unfused or fused with benzene, heteroarene or $R^{13.4}$; $R^{13.4}$ is cycloalkane, cycloalkene, heterocycloalkane or heterocycloalkene;

$R^{14}$ is heteroaryl, which is unfused or fused with benzene, heteroarene or $R^{14.4}$; $R^{14.4}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15.4}$; $R^{15.4}$ is cycloalkane, cycloalkene, heterocycloalkane or heterocycloalkene;

$R^{16}$ is alkyl, alkenyl or alkynyl;

wherein the moiety represented by $R^{101}$ is H, $R^{41}$, $OR^{41}$, $SR^{41}$, $S(O)R^{41}$, $SO_2R^{41}$, $C(O)R^{41}$, $C(O)OR^{41}$, $OC(O)R^{41}$, $OC(O)OR^{41}$, $NH_2$, $NHR^{41}$, $N(R^{41})_2$, $NHC(O)R^{41}$, $NR^{41}C(O)R^{41}$, $NHS(O)_2R^{41}$, $NR^{41}S(O)_2R^{41}$, $NHC(O)OR^{41}$, $NR^{41}C(O)OR^{41}$, $NHC(O)NH_2$, $NHC(O)NHR^{41}$, $NHC(O)N(R^{41})_2$, $NR^{41}C(O)NHR^{41}$, $NR^{41}C(O)N(R^{41})_2$, $C(O)NH_2$, $C(O)NHR^{41}$, $C(O)N(R^{41})_2$, $C(O)NHOH$, $C(O)NHOR^{41}$, $C(O)NHSO_2R^{41}$, $C(O)NR^{41}SO_2R^{41}$, $SO_2NH_2$, $SO_2NHR^{41}$, $SO_2N(R^{41})_2$, C(O)H, C(O)OH, $C(N)NH_2$, $C(N)NHR^{41}$, $C(N)N(R^{41})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{41}$ is $R^{42}$, $R^{43}$, $R^{44}$ or $R^{45}$;

$R^{42}$ is phenyl, which is unfused or fused with benzene, heteroarene or $R^{42.4}$; $R^{42.4}$ is cycloalkane, cycloalkene, heterocycloalkane or heterocycloalkene;

$R^{43}$ is heteroaryl, which is unfused or fused with benzene, heteroarene or $R^{43.4}$; $R^{43.4}$ is cycloalkane, cycloalkene, heterocycloalkane or heterocycloalkene;

$R^{44}$ is cycloalkyl, cycloalkenyl, heterocycloalkyl, or heterocycloalkenyl, each of which is unfused or fused with benzene, heteroarene or $R^{44.4}$; $R^{44.4}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $SR^{46}$, $S(O)R^{46}$, $SO_2R^{46}$, $C(O)R^{46}$, $C(O)OR^{46}$, $OC(O)R^{46}$, $OC(O)OR^{46}$, $NH_2$, $NHR^{46}$, $N(R^{46})_2$, $NHC(O)R^{46}$, $NR^{46}C(O)R^{46}$, $NHS(O)_2R^{46}$, $NR^{46}S(O)_2R^{46}$, $NHC(O)OR^{46}$, $NR^{46}C(O)OR^{46}$, $NHC(O)NH_2$, $NHC(O)NHR^{46}$, $NHC(O)N(R^{46})_2$, $NR^{46}C(O)NHR^{46}$, $NR^{46}C(O)N(R^{46})_2$, $C(O)NH_2$, $C(O)NHR^{46}$, $C(O)N(R^{46})_2$, $C(O)NHOH$, $C(O)NHOR^{46}$, $C(O)NHSO_2R^{46}$, $C(O)NR^{46}SO_2R^{46}$, $SO_2NH_2$, $SO_2NHR^{46}$, $SO_2N(R^{46})_2$, C(O)H, C(O)OH, $C(N)NH_2$, $C(N)NHR^{46}$, $C(N)N(R^{46})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{46}$ is alkyl, alkenyl, alkynyl, $R^{47}$, $R^{48}$ or $R^{49}$;

$R^{47}$ is phenyl, which is unfused or fused with benzene, heteroarene or $R^{47.4}$; $R^{47.4}$ is cycloalkane, cycloalkene, heterocycloalkane or heterocycloalkene;

$R^{48}$ is heteroaryl, which is unfused or fused with benzene, heteroarene or $R^{48.4}$; $R^{48.4}$ is cycloalkane, cycloalkene, heterocycloalkane or heterocycloalkene;

$R^{49}$ is cycloalkyl, cycloalkenyl, heterocycloalkyl, or heterocycloalkenyl, each of which is unfused or fused with benzene, heteroarene or $R^{49.4}$; $R^{49.4}$ is cycloalkane, cycloalkene, heterocycloalkane or heterocycloalkene;

the moieties represented by $R^{42}$, $R^{43}$, $R^{44}$, $R^{47}$, $R^{48}$, and $R^{49}$ are independently unsubstituted or substituted with one or more independently selected $R^{50}$, $OR^{50}$, $SR^{50}$, $S(O)R^{50}$, $SO_2R^{50}$, $C(O)R^{50}$, $C(O)OR^{50}$, $OC(O)R^{50}$, $OC(O)OR^{50}$, $NH_2$, $NHR^{50}$, $N(R^{50})_2$, $NHC(O)R^{50}$, $NR^{50}C(O)R^{50}$, $NHS(O)_2R^{50}$, $NR^{50}S(O)_2R^{50}$, $NHC(O)OR^{50}$, $NR^{50}C(O)OR^{50}$, $NHC(O)NH_2$, $NHC(O)NHR^{50}$, $NHC(O)N(R^{50})_2$, $NR^{50}C(O)NHR^{50}$, $NR^{50}C(O)N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{50}SO_2R^{50}$, $SO_2NH_2$, $SO_2NHR^{50}$, $SO_2N(R^{50})_2$, $C(O)H$, $C(O)OH$, $C(N)NH_2$, $C(N)NHR^{50}$, $C(N)N(R^{50})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl, which is unfused or fused with benzene, heteroarene or $R^{51A}$; $R^{51A}$ is cycloalkane, cycloalkene, heterocycloalkane or heterocycloalkene;

$R^{52}$ is heteroaryl, which is unfused or fused with benzene, heteroarene or $R^{52A}$; $R^{52A}$ is cycloalkane, cycloalkene, heterocycloalkane or heterocycloalkene;

$R^{53}$ is cycloalkyl, cycloalkenyl, heterocycloalkyl, or heterocycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $C(O)R^{55}$, $C(O)OR^{55}$, $OC(O)R^{55}$, $OC(O)OR^{55}$, $NH_2$, $NHR^{55}$, $N(R^{55})_2$, $NHC(O)R^{55}$, $NR^{55}C(O)R^{55}$, $NHS(O)_2R^{55}$, $NR^{55}S(O)_2R^{55}$, $NHC(O)OR^{55}$, $NR^{55}C(O)OR^{55}$, $NHC(O)NH_2$, $NHC(O)NHR^{55}$, $NHC(O)N(R^{55})_2$, $NR^{55}C(O)NHR^{55}$, $NR^{55}C(O)N(R^{55})_2$, $C(O)NH_2$, $C(O)NHR^{55}$, $C(O)N(R^{55})_2$, $C(O)NHOH$, $C(O)NHOR^{55}$, $C(O)NHSO_2R^{55}$, $C(O)NR^{55}SO_2R^{55}$, $SO_2NH_2$, $SO_2NHR^{55}$, $SO_2N(R^{55})_2$, $C(O)H$, $C(O)OH$, $C(N)NH_2$, $C(N)NHR^{55}$, $C(N)N(R^{55})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{55}$ is alkyl, alkenyl, alkynyl, phenyl, heteroaryl, cycloalkyl, cycloalkenyl, heterocycloalkyl, or heterocycloalkenyl;

wherein each foregoing cyclic moiety is independently unsubstituted, further unsubstituted, substituted or further substituted with one or more independently selected $R^{57}$, $OR^{57}$, $SR^{57}$, $S(O)R^{57}$, $SO_2R^{57}$, $C(O)R^{57}$, $C(O)OR^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl, or alkynyl, each of which is unsubstituted or substituted with one or two or three independently selected $R^{62}$, $OR^{62}$, $SR^{62}$, $S(O)R^{62}$, $SO_2R^{62}$, $C(O)R^{62}$, $C(O)OR^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl, or alkenyl, each of which is unsubstituted or substituted with one or two or three independently selected $R^{67}$, $OR^{67}$, $SR^{67}$, $S(O)R^{67}$, $SO_2R^{67}$, $C(O)R^{67}$, $C(O)OR^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the moieties represented by $R^{58}$, $R^{59}$, $R^{60}$, $R^{63}$, $R^{64}$, $R^{65}$, and $R^{67}$ are unsubstituted or substituted with one or more independently selected $R^{68}$, $OR^{68}$, $SR^{68}$, $S(O)R^{68}$, $SO_2R^{68}$, $C(O)R^{68}$, $C(O)OR^{68}$, $OC(O)R^{68}$, $OC(O)OR^{68}$, $NH_2$, $NHR^{68}$, $N(R^{68})_2$, $NHC(O)R^{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{68}$ is $R^{69}$, $R^{70}$, $R^{71}$ or $R^{72}$;

$R^{69}$ is phenyl, which is unfused or fused with benzene, heteroarene or $R^{69A}$; $R^{69A}$ is cycloalkane, cycloalkene, heterocycloalkane or heterocycloalkene;

$R^{70}$ is heteroaryl, which is unfused or fused with benzene, heteroarene or $R^{70A}$; $R^{70A}$ is cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with benzene, heteroarene or $R^{71A}$; $R^{71A}$ is cycloalkane, cycloalkene, heterocycloalkane or heterocycloalkene;

$R^{72}$ is alkyl, alkenyl, or alkenyl, each of which is unsubstituted or substituted with one or two or three independently selected $R^{73}$, $OR^{73}$, $SR^{73}$, $S(O)R^{73}$, $SO_2R^{73}$, $C(O)R^{73}$, $C(O)OR^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, NHC(O)N($R^{73}$)$_2$, $NR^{73}$C(O)$NHR^{73}$, $NR^{73}$C(O)N($R^{73}$)$_2$, C(O)NH$_2$, C(O)$NHR^{73}$, C(O)N($R^{73}$)$_2$, C(O)NHOH, C(O)N-$HOR^{73}$, C(O)NHSO$_2$$R^{73}$, C(O)$NR^{73}$SO$_2$$R^{73}$, SO$_2$NH$_2$, SO$_2$$NHR^{73}$, SO$_2$N($R^{73}$)$_2$, C(O)H, C(O)OH, C(N)NH$_2$, C(N)$NHR^{73}$, C(N)N($R^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

$R^{73}$ is alkyl, alkenyl, alkenyl, phenyl, heteroaryl, cycloalkyl, cycloalkenyl, heterocycloalkyl, or heterocycloalkenyl; and the moieties represented by $R^{69}$, $R^{70}$, and $R^{71}$ are unsubstituted or substituted with one or more independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, CF$_3$, CF$_2$CF$_3$, OCF$_3$, OCF$_2$CF$_3$, F, Cl, Br or I substituents.

Still another embodiment pertains to compounds having Formula I, which are

4-[4-(cyclohexylmethyl)-4-methoxypiperidin-1-yl]-N-{[5-({(1R)-3-(dimethylamino)-1-[(phenylthio)methyl] propyl}amino)-4-nitrothien-2-yl]sulfonyl}benzamide;

N-{[5-({(1R)-3-(dimethylamino)-1-[(phenylthio)methyl] propyl}amino)-4-nitrothien-2-yl]sulfonyl}-4-[4-methoxy-4-(3-methylbenzyl)piperidin-1-yl]benzamide;

N-{[5-({(1R)-3-(dimethylamino)-1-[(phenylthio)methyl] propyl}amino)-4-nitrothien-2-yl]sulfonyl}-4-[4-(3,3-diphenylprop-2-enyl)piperazin-1-yl]benzamide;

4-{4-[(4'-chloro-1,1'-biphenyl-2-yl)methyl]piperazin-1-yl}-N-[(4-{[2-(phenylthio)ethyl]amino}piperidin-1-yl)sulfonyl]benzamide;

N-[(4-{acetyl[2-(phenylthio)ethyl]amino}piperidin-1-yl) sulfonyl]-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-[(4-{methyl[2-(phenylthio)ethyl]amino}piperidin-1-yl)sulfonyl]benzamide;

4-{4-[(4'-chloro-1,1'-biphenyl-2-yl)methyl]piperazin-1-yl}-N-{[5-({(1R)-3-[isopropyl(methyl)amino]-1-[(phenylthio)methyl]propyl}amino)-4-nitrothien-2-yl] sulfonyl}benzamide;

4-(4-{[2-(4-chlorophenyl)cyclohex-1-en-1-yl] methyl}piperazin-1-yl)-N-{[5-({(1R)-3-[isopropyl(methyl)amino]-1-[(phenylthio)methyl]propyl}amino)-4-nitrothien-2-yl]sulfonyl}benzamide;

4-(4-{[2-(4-chlorophenyl)-5,5-dimethylcyclohex-1-en-1-yl]methyl}piperazin-1-yl)-N-{[5-({(1R)-3-[isopropyl(methyl)amino]-1-[(phenylthio)methyl]propyl}amino)-4-nitrothien-2-yl]sulfonyl}benzamide;

N-{[(5Z)-5-(acetylimino)-4-methyl-4,5-dihydro-1,3,4-thiadiazol-2-yl]sulfonyl}-4-{4-[(4'-chloro-1,1'-biphenyl-2-yl)methyl]piperazin-1-yl}benzamide;

N-{[2-(acetylamino)-4-methyl-1,3-thiazol-5-yl]sulfonyl}-4-{4-[(4'-chloro-1,1'-biphenyl-2-yl)methyl]piperazin-1-yl}benzamide;

N-({5-[(benzoylamino)methyl]thien-2-yl}sulfonyl)-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-[(6-chloroimidazo[2,1-b][1,3]thiazol-5-yl)sulfonyl] benzamide;

4-{4-[(4'-chloro-1,1'-biphenyl-2-yl)methyl]piperazin-1-yl}-N-(morpholin-4-ylsulfonyl)benzamide;

4-{4-[(4'-chloro-1,1'-biphenyl-2-yl)methyl]piperazin-1-yl}-N-(2,4-dimethyl-1,3-thiazol-5-yl)sulfonyl]benzamide;

4-{4-[(4'-chloro-1,1'-biphenyl-2-yl)methyl]piperazin-1-yl}-N-{[4-phenyl-5-(trifluoromethyl)thien-3-yl] sulfonyl}benzamide;

4-{4-[(4'-chloro-1,1'-biphenyl-2-yl)methyl]piperazin-1-yl}-N-[(5-fluoro-3-methyl-1-benzothien-2-yl)sulfonyl]benzamide;

N-(1,3-benzothiazol-2-ylsulfonyl)-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-(thien-2-ylsulfonyl)benzamide;

4-{4-[(4'-chloro-1,1'-biphenyl-2-yl)methyl]piperazin-1-yl}-N-[(5,7-dimethyl[1,2,4]triazolo[1,5-a]pyrimidin-2-yl)sulfonyl]benzamide;

ethyl 4-{[(4-{4-[(4'-chloro-1,1'-biphenyl-2-yl)methyl]piperazin-1-yl}benzoyl)amino]sulfonyl}-5-methyl-1,2-diphenyl-1H-pyrrole-3-carboxylate;

methyl 5-{[(4-{4-[(4'-chloro-1,1'-biphenyl-2-yl)methyl]piperazin-1-yl}benzoyl)amino]sulfonyl}-1-methyl-1H-pyrrole-2-carboxylate;

4-{4-[(4'-chloro-1,1'-biphenyl-2-yl)methyl]piperazin-1-yl}-N-{[5-(1,3-dimethyl-1H-pyrazol-5-yl)isoxazol-4-yl] sulfonyl}benzamide;

4-{4-[(4'-chloro-1,1'-biphenyl-2-yl)methyl]piperazin-1-yl}-N-[(4-chloro-3-methylisothiazol-5-yl)sulfonyl]benzamide;

N-[(5-bromo-3-methyl-1-benzothien-2-yl)sulfonyl]-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-({5-[(E)-2-(1,2,4-oxadiazol-3-yl)vinyl]thien-2-yl}sulfonyl)benzamide;

4-{4-[(4'-chloro-1,1'-biphenyl-2-yl)methyl]piperazin-1-yl}-N-{[1-(2-chloroethyl)-3,5-dimethyl-1H-pyrazol-4-yl] sulfonyl}benzamide;

5-{[(4-{4-[(4'-chloro-1,1'-biphenyl-2-yl)methyl]piperazin-1-yl}benzoyl)amino]sulfonyl}-N-(1-ethylpropyl)-1,3,4-thiadiazole-2-carboxamide;

4-{4-[(4'-chloro-1,1'-biphenyl-2-yl)methyl]piperazin-1-yl}-N-[(5-chloro-1,3-dimethyl-1H-pyrazol-4-yl)sulfonyl] benzamide;

4-{4-[(4'-chloro-1,1'-biphenyl-2-yl)methyl]piperazin-1-yl}-N-[(4-nitro-5-piperidin-1-ylthien-2-yl)sulfonyl]benzamide;

4-{4-[(4'-chloro-1,1'-biphenyl-2-yl)methyl]piperazin-1-yl}-N-[(5-isoxazol-5-yl-2-furyl)sulfonyl]benzamide;

4-{4-[(4'-chloro-1,1'-biphenyl-2-yl)methyl]piperazin-1-yl}-N-[(3,5-dimethylisoxazol-4-yl)sulfonyl]benzamide;

4-(4-{[2-(4-chlorophenyl)-4,4-dimethylcyclohex-1-en-1-yl] methyl}piperazin-1-yl)-2-(1H-indol-5-yloxy)-N-({4-nitro-5-[(3-pyrrolidin-1-ylpropyl)amino]thien-2-yl}sulfonyl)benzamide;

4-(4-{[2-(4-chlorophenyl)-4,4-dimethylcyclohex-1-en-1-yl] methyl}piperazin-1-yl)-N-[(5-{[3-(dimethylamino)propyl]amino}-4-nitrothien-2-yl)sulfonyl]-2-(1H-indol-5-yloxy)benzamide;

4-(4-{[2-(4-chlorophenyl)-4,4-dimethylcyclohex-1-en-1-yl] methyl}piperazin-1-yl)-2-(1H-indol-5-yloxy)-N-({5-[(3-morpholin-4-ylpropyl)amino]-4-nitrothien-2-yl}sulfonyl) benzamide;

N-{[5-({(1R)-3-(dimethylamino)-1-[(phenylthio)methyl] propyl}amino)-4-nitrothien-2-yl]sulfonyl}-4-{4-[2-(trifluoromethyl)benzylidene]piperidin-1-yl}benzamide;

4-{4-[(4'-chloro-1,1'-biphenyl-2-yl)methylene]piperidin-1-yl}-N-[(1,1-dioxidotetrahydrothien-3-yl)sulfonyl]benzamide;

4-{4-[(4'-chloro-1,1'-biphenyl-2-yl)methylene]piperidin-1-yl}-N-[(5-chloro-3-methyl-1-benzothien-2-yl)sulfonyl] benzamide;

4-{4-[(4'-chloro-1,1'-biphenyl-2-yl)methyl]piperazin-1-yl}-N-[(5-chloro-3-methyl-1-benzothien-2-yl)sulfonyl]-2-phenoxybenzamide;

2-(3-chlorophenoxy)-4-(4-{[2-(4-chlorophenyl)-4,4-dimethylcyclohex-1-en-1-yl]methyl}piperazin-1-yl)-N-[(5,7-dimethyl[1,2,4]triazolo[1,5-a]pyrimidin-2-yl)sulfonyl]benzamide;

4-(4-{[2-(4-chlorophenyl)-4,4-dimethylcyclohex-1-en-1-yl]methyl}piperazin-1-yl)-N-[(5,7-dimethyl[1,2,4]triazolo[1,5-a]pyrimidin-2-yl)sulfonyl]-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-[(5,7-dimethyl[1,2,4]triazolo[1,5-a]pyrimidin-2-yl)sulfonyl]benzamide;

tert-butyl (2S)-2-{[(5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-4-methyl-1,3-thiazol-2-yl)oxy]methyl}morpholine-4-carboxylate;

tert-butyl (2S)-2-{[(5-{[2-(1H-benzimidazol-4-yloxy)-4-(4-{[2-(4-chlorophenyl)-4,4-dimethylcyclohex-1-en-1-yl]methyl}piperazin-1-yl)benzoyl]sulfamoyl}-4-methyl-1,3-thiazol-2-yl)oxy]methyl}morpholine-4-carboxylate;

4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-pyrrolo[2,3-b]pyridin-5-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)benzamide;

tert-butyl (2S)-2-{[(5-{[4-(4-{[2-(4-chlorophenyl)-4,4-dimethylcyclohex-1-en-1-yl]methyl}piperazin-1-yl)-2-(1H-indazol-4-yloxy)benzoyl]sulfamoyl}-4-methyl-1,3-thiazol-2-yl)oxy]methyl}morpholine-4-carboxylate;

4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-indazol-4-yloxy)benzamide;

and therapeutically acceptable salts, prodrugs, salts of prodrugs and metabolites thereof.

Another embodiment pertains to a composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said composition comprising an excipient and a therapeutically effective amount of the compound of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient a therapeutically effective amount of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient therapeutically effective amount of the compound of Formula (I) and a therapeutically effective amount of one additional therapeutic agent or more than one additional therapeutic agent.

DETAILED DESCRIPTION OF THE INVENTION

Variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "alkenyl" as used herein, means a straight or branched hydrocarbon chain containing from 2 to 10 carbons and containing at least one carbon-carbon double bond. The term "$C_x$-$C_y$ alkyl" means a straight or branched hydrocarbon chain containing at least one carbon-carbon double bond containing x to y carbon atoms. The term "$C_2$-$C_4$ alkenyl" means an alkenyl group containing 2-4 carbon atoms. Representative examples of alkenyl include, but are not limited to buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. The term "$C_x$-$C_y$ alkylene" means a divalent group derived from a straight or branched hydrocarbon chain containing at least one carbon-carbon double bond and containing x to y carbon atoms. Representative examples of alkenylene include, but are not limited to, —CH=CH— and —CH$_2$CH=CH—.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_2$-$C_{10}$ alkyl" means a straight or branched chain, saturated hydrocarbon containing 2 to 10 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 4 carbon atoms. The term "$C_x$-$C_y$ alkylene" means a divalent group derived from a straight or branched chain, saturated hydrocarbon containing x to y carbon atoms. For example "$C_2$-$C_6$ alkylene" means a straight or branched chain, saturated hydrocarbon containing 2 to 6 carbon atoms. Examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_x$-$C_y$ alkynyl" means a straight or branched chain hydrocarbon group containing from x to y carbon atoms. Representative examples of alkynyl include, but are not limited, to acetylenyl, 1-propynyl, 2-propynyl, 3-butynyl, 2-pentynyl, and 1-butynyl.

The term "alkynylene," as used herein, means a divalent radical derived from a straight or branched chain hydrocarbon group containing from 2 to 10 carbon atoms and containing at least one carbon-carbon triple bond.

The term "aryl" as used herein, means phenyl.

The term "cyclic moiety," as used herein, means benzene, phenyl, phenylene, cycloalkane, cycloalkyl, cycloalkylene, cycloalkene, cycloalkenyl, cycloalkenylene, cycloalkyne, cycloalkynyl, cycloalkynylene, heteroarene, heteroaryl, heterocycloalkane, heterocycloalkyl, heterocycloalkene, heterocycloalkenyl and spiroalkyl.

The term "cycloalkylene" or cycloalkyl" or "cycloalkane" as used herein, means a monocyclic or bridged hydrocarbon ring system. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and bridged cycloalkyl can be attached to the parent molecular moiety through any substitutable atom contained within the ring system.

The term "cycloalkenylene," or "cycloalkenyl" or "cycloalkene" as used herein, means a monocyclic or a bridged hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The monocyclic cycloalkenyl ring may contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems.

The term "cycloalkyne," or "cycloalkynyl," or "cycloalkynylene," as used herein, means a monocyclic or a bridged hydrocarbon ring system. The monocyclic cycloalkynyl has eight or more carbon atoms, zero heteroatoms, and one or more triple bonds. The monocyclic cycloalkynyl ring may contain one or two alkylene bridges, each consisting of one, two, or three carbon atoms, each linking two non-adjacent carbon atoms of the ring system. The monocyclic and bridged cycloalkynyl can be attached to the parent molecular moiety through any substitutable atom contained within the ring systems.

The term "heteroarene," or "heteroaryl," or "heteroarylene," as used herein, means a five-membered or six-membered aromatic ring having at least one carbon atom and one or more than one independently selected nitrogen, oxygen or sulfur atom. The heteroarenes of this invention are connected through any adjacent atoms in the ring, provided that proper valences are maintained. Representative examples of heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, thiazolyl, thienyl (including, but not limited thereto, thien-2-yl, thien-3-yl), triazolyl, and triazinyl.

The term "heterocycloalkane," or "heterocycloalkyl," or "heterocycloalkylene," as used herein, means monocyclic or bridged three-, four-, five-, six-, seven-, or eight-membered ring containing at least one heteroatom independently selected from the group consisting of O, N, and S and zero double bonds. The monocyclic and bridged heterocycloalkane are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkane groups include, but are not limited to, Representative examples of heterocycloalkane groups include, but are not limited to, morpholinyl, tetrahydropyranyl, pyrrolidinyl, piperidinyl, dioxolanyl, tetrahydrofuranyl, thiomorpholinyl, dioxanyl, tetrahydrothienyl, tetrahydrothiopyranyl, oxetanyl, piperazinyl, imidazolidinyl, azetidine, azepanyl, aziridinyl, diazepanyl, dithiolanyl, dithianyl, isoxazolidinyl, isothiazolidinyl, oxadiazolidinyl, oxazolidinyl, pyrazolidinyl, tetrahydrothienyl, thiadiazolidinyl, thiazolidinyl, thiomorpholinyl, trithianyl, and trithianyl.

The term "heterocycloalkene," or "heterocycloalkenyl," or "heterocycloalkenylene," as used herein, means monocyclic or bridged three-, four-, five-, six-, seven-, or eight-membered ring containing at least one heteroatom independently selected from the group consisting of O, N, and S and one or more double bonds. The monocyclic and bridged heterocycloalkene are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkene groups include, but are not limited to, tetrahydrooxocinyl, 1,4,5,6-tetrahydropyridazinyl, 1,2,3,6-tetrahydropyridinyl, dihydropyranyl, imidazolinyl, isothiazolinyl, oxadiazolinyl, isoxazolinyl, oxazolinyl, pyranyl, pyrazolinyl, pyrrolinyl, thiadiazolinyl, thiazolinyl, dihydro-1,3,4-thiadiazol-2-yl, and thiopyranyl.

The term "phenylene," as used herein, means a divalent radical formed by removal of a hydrogen atom from phenyl.

The term "spiroalkyl," as used herein, means alkylene, both ends of which are attached to the same carbon atom and is exemplified by $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl, $C_9$-spiroalkyl and the like.

The term "spiroheteroalkyl," as used herein, means spiroalkyl having one or two $CH_2$ moieties replaced with independently selected O, C(O), CNOH, CNOCH$_3$, S, S(O), SO$_2$ or NH and one or two CH moieties unreplaced or replaced with N.

The term "spiroheteroalkenyl," as used herein, means spiroalkenyl having one or two CH$_2$ moieties replaced with independently selected O, C(O), CNOH, CNOCH$_3$, S, S(O), SO$_2$ or NH and one or two CH moieties unreplaced or replaced with N and also means spiroalkenyl having one or two CH$_2$ moieties unreplaced or replaced with independently selected O, C(O), CNOH, CNOCH$_3$, S, S(O), SO$_2$ or NH and one or two CH moieties replaced with N.

The term, "spirocyclo," as used herein, means two substituents on the same carbon atom, that, together with the carbon atom to which they are attached, form a cycloalkane, heterocycloalkane, cycloalkene, or heterocycloalkene ring.

The term "C$_2$-C$_5$-spiroalkyl," as used herein, means C$_2$-spiroalkyl, C$_3$-spiroalkyl, C$_4$-spiroalkyl, and C$_5$-spiroalkyl.

The term "C$_2$-spiroalkyl," as used herein, means eth-1,2-ylene, both ends of which replace hydrogen atoms of the same CH$_2$ moiety.

The term "C$_3$-spiroalkyl," as used herein, means prop-1,3-ylene, both ends of which replace hydrogen atoms of the same CH$_2$ moiety.

The term "C$_4$-spiroalkyl," as used herein, means but-1,4-ylene, both ends of which replace hydrogen atoms of the same CH$_2$ moiety.

The term "C$_5$-spiroalkyl," as used herein, means pent-1,5-ylene, both ends of which replace hydrogen atoms of the same CH$_2$ moiety.

The term "C$_6$-spiroalkyl," as used herein, means hex-1,6-ylene, both ends of which replace hydrogen atoms of the same CH$_2$ moiety.

The term "NH protecting group," as used herein, means trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble *J. Org. Chem.* 1998, 63, 2758-2760 and E. L. Eliel, and S. H. Wilen. (1994) *Stereochemistry of Organic Compounds*. New York, N.Y.: John Wiley & Sons, Inc.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of this invention containing NH, C(O)OH, OH or SH moieties may have attached thereto prodrug-forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance Isotope Enriched or Labeled Compounds Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521, 421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999)).

In addition, non-radio active isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-isotopic compound.

Amides, Esters and Prodrugs

Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, phosphates, phosphate esters, and enamines of the active drug, b) functionalizing the drug with azo, glycoside, peptide, and ether functional groups, c) use of aminals, hemi-aminals, polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated in its entirety by reference herein.

Esters can be prepared from substrates of formula (I) containing either a hydroxyl group or a carboxy group by general methods known to persons skilled in the art. The typical reactions of these compounds are substitutions replacing one of the heteroatoms by another atom, for example:

Scheme 1

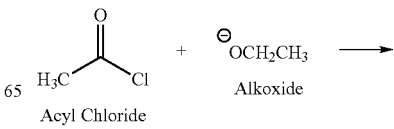

Acyl Chloride

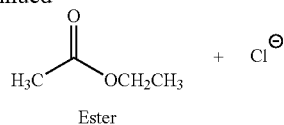
Ester

Amides can be prepared from substrates of formula (I) containing either an amino group or a carboxy group in similar fashion. Esters can also react with amines or ammonia to form amides.

Scheme 2

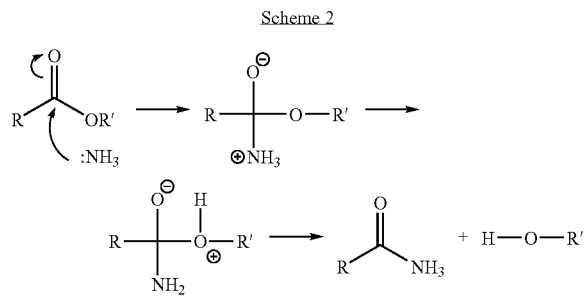

Another way to make amides from compounds of formula (I) is to heat carboxylic acids and amines together.

Scheme 3

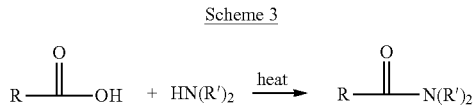

In Schemes 2 and 3 above, R and R' are independently substrates of formula (I), alkyl or hydrogen.

Suitable groups for $A^1$, $L^1$, $Z^{1A}$, $Z^{2A}$, $Z^1$, $Z^2$, and $Z^3$ in compounds of Formula (I) are independently selected. The described embodiments of the present invention may be combined. Such combination is contemplated and within the scope of the present invention. For example, it is contemplated that embodiments for any of $A^1$, $L^1$, $Z^{1A}$, $Z^{2A}$, $Z^1$, $Z^2$, and $Z^3$ can be combined with embodiments defined for any other of $A^1$, $L^1$, $Z^{1A}$, $Z^{2A}$, $Z^1$, $Z^2$, and $Z^3$.

One embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (I)

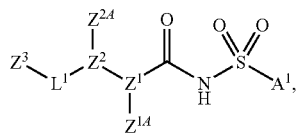

wherein $A^1$ is furyl, imidazolyl, isothiazolyl, isoxazolyl, oxadiazolyl, oxazolyl, pyrazinyl, pyrazolyl, pyridazinyl, 2-pyridinyl, 4-pyridinyl, pyrimidinyl, pyrrolyl, tetrazolyl, thiazolyl, thiadiazolyl, thienyl, triazinyl, triazolyl, cycloalkyl, cycloalkenyl, heterocycloalkyl, or heterocycloalkenyl; each of which is unfused or fused with benzene, heteroarene or $A^{1A}$; $A^{1A}$ is cycloalkane, cycloalkene, heterocycloalkane, or heterocycloalkene;

wherein $A^1$ is unsubstituted or substituted with one or two or three or four or five independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(N)C(O)R^1$, $C(O)NHR^1$, $C(O)N(R^1)_2$, $C(O)NHOH$, $C(O)NHOR^1$, $C(O)NHSO_2R^1$, $NHC(O)R^1$, $NR^1C(O)R^1$, $NHC(O)OR^1$, $NR^1C(O)OR^1$, $NR^1C(O)NHR^1$, $NR^1C(O)N(R^1)_2$, $NHC(O)NH_2$, $NHC(O)NHR^1$, $NHC(O)N(R^1)_2$, $SO_2NH_2$, $SO_2NHR^1$, $SO_2N(R^1)_2$, $NHS(O)R^1$, $NHSO_2R^1$, $NR^1SO_2R^1$, $NHSO_2NHR^1$, $N(CH_3)SO_2N(CH_3)R^1$, (O), $NH_2$, $NO_2$, $N_3$, OH, F, Cl, Br, I, CN, $CF_3$, $OCF_3$, $CF_2CF_3$, $OCF_2CF_3$, $C(O)H$, $C(O)OH$, $C(N)NH_2$, $C(N)NHR^1$, $C(N)N(R^1)_2$, CNOH, $CNOCH_3$, $C(O)NH_2$ or $C(O)OR^{1A}$;

$R^1$ is $R^2$, $R^3$, $R^4$ or $R^5$;

$R^{1A}$ is cycloalkyl, cycloalkenyl or cycloalkynyl;

$R^2$ is phenyl, which is unfused or fused with benzene, heteroarene or $R^{2A}$; $R^{2A}$ is cycloalkane, cycloalkene, heterocycloalkane or heterocycloalkene;

$R^3$ is heteroaryl, which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl, which is unfused or fused with benzene, heteroarene or $R^{8A}$; $R^{8A}$ is cycloalkane, cycloalkene, heterocycloalkane or heterocycloalkene;

$R^9$ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl, or heterocycloalkenyl each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $SR^{12}$, $S(O)R^{12}$, $SO_2R^{12}$, $C(O)R^{12}$, $C(O)OR^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$Z^1$ is $R^{26}$ or $R^{27}$;

$Z^2$ is $R^{28}$, $R^{29}$ or $R^{30}$;

$Z^{1A}$ and $Z^{2A}$ are both absent or are taken together to form $CH_2$, $CH_2CH_2$ or $Z^{12A}$;

$Z^{12A}$ is $C_2$-$C_6$-alkylene having one or two $CH_2$ moieties replaced by NH, $N(CH_3)$, S, S(O) or $SO_2$;

$L^1$ is a $R^{37}$, $OR^{37}$, $SR^{37}$, $S(O)R^{37}$, $SO_2R^{37}$, $C(O)R^{37}$, $C(O)OR^{37}$, $OC(O)R^{37}$, $OC(O)OR^{37}$, $NHR^{37}$, C(O)NH, $C(O)NR^{37}$, $C(O)NHOR^{37}$, $C(O)NHSO_2R^{37}$, $SO_2NH$, $SO_2NHR^{37}$, C(N)NH, $C(N)NHR^{37}$;

$R^{26}$ is phenylene which is unfused or fused with benzene or heteroarene or $R^{26A}$; $R^{26A}$ is cycloalkane, cycloalkene, heterocycloalkane or heterocycloalkene;

$R^{27}$ is heteroarylene, which is unfused or fused with benzene or heteroarene or $R^{27A}$; $R^{27A}$ is cycloalkane, cycloalkene, heterocycloalkane or heterocycloalkene;

$R^{28}$ is phenylene, which is unfused or fused with benzene, heteroarene or $R^{28A}$; $R^{28A}$ is cycloalkane, cycloalkene, heterocycloalkane or heterocycloalkene;

$R^{29}$ is heteroarylene, which is unfused or fused with benzene or heteroarene or $R^{29A}$; $R^{29A}$ is cycloalkane, cycloalkene, heterocycloalkane or heterocycloalkene;

$R^{30}$ is cycloalkylene, cycloalkenylene, heterocycloalkylene or heterocycloalkenylene, each of which is unfused or fused with benzene, heteroarene or $R^{30A}$; $R^{30A}$ is cycloalkane, cycloalkene, heterocycloalkane or heterocycloalkene;

$R^{37}$ is a bond or $R^{37A}$;

$R^{37A}$ is alkylene, alkenylene, or alkynylene, each of which is unsubstituted or substituted with one or two or three independently selected $R^{37B}$, $OR^{37B}$, $SR^{37B}$, $S(O)R^{37B}$, $SO_2R^{37B}$, $C(O)R^{37B}$, $C(O)OR^{37B}$, $OC(O)R^{37B}$, $OC(O)OR^{37B}$, $NH_2$, $NHR^{37B}$, $N(R^{37B})_2$, $NHC(O)R^{37B}$, $NR^{37B}C(O)R^{37B}$, $NHS(O)_2R^{37B}$, $NR^{37B}S(O)_2R^{37B}$, $NHC(O)OR^{37B}$, $NR^{37B}C(O)OR^{37B}$, $NHC(O)NH_2$, $NHC(O)NHR^{37B}$, $NHC(O)N(R^{37B})_2$, $NR^{37B}C(O)NHR^{37B}$, $NR^{37B}C(O)N(R^{37B})_2$, $C(O)NH_2$, $C(O)NHR^{37B}$, $C(O)N(R^{37B})_2$, $C(O)NHOH$, $C(O)NHOR^{37B}$, $C(O)NHSO_2R^{37B}$, $C(O)NR^{37B}SO_2R^{37B}$, $SO_2NH_2$, $SO_2NHR^{37B}$, $SO_2N(R^{37B})_2$, C(O)H, C(O)OH, $C(N)NH_2$, $C(N)NHR^{37B}$, $C(N)N(R^{37B})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{37B}$ is alkyl, alkenyl, alkynyl, phenyl, heteroaryl, cycloalkyl, cycloalkenyl, heterocycloalkyl, or heterocycloalkenyl;

$Z^3$ is $R^{38}$, $R^{39}$ or $R^{40}$;

$R^{38}$ is phenyl, which is unfused or fused with benzene, heteroarene or $R^{38A}$; $R^{38A}$ is cycloalkane, cycloalkene, heterocycloalkane or heterocycloalkene;

$R^{39}$ is heteroaryl, which is unfused or fused with benzene, heteroarene or $R^{39A}$; $R^{39A}$ is cycloalkane, cycloalkene, heterocycloalkane or heterocycloalkene;

$R^{40}$ is cycloalkyl, cycloalkenyl, heterocycloalkyl, or heterocycloalkenyl, each of which is unfused or fused with benzene, heteroarene or $R^{40A}$; $R^{40A}$ is cycloalkane, cycloalkene, heterocycloalkane or heterocycloalkene;

wherein the moieties represented by $R^{26}$ and $R^{27}$ are unsubstituted or substituted, (i.e., if $Z^{1A}$ and $Z^{2A}$ are absent) or further unsubstituted or further substituted (i.e., if $Z^{1A}$ and $Z^{2A}$ are present) with one or more $R^{41}$, $OR^{41}$, $SR^{41}$, $S(O)R^{41}$, $SO_2R^{41}$, $C(O)R^{41}$, $C(O)OR^{41}$, $OC(O)R^{41}$, $OC(O)OR^{41}$, $NH_2$, $NHR^{41}$, $N(R^{41})_2$, $NHC(O)R^{41}$, $NR^{41}C(O)R^{41}$, $NHS(O)_2R^{41}$, $NR^{41}S(O)_2R^{41}$, $NHC(O)OR^{41}$, $NR^{41}C(O)OR^{41}$, $NHC(O)NH_2$, $NHC(O)NHR^{41}$, $NHC(O)N(R^{41})_2$, $NR^{41}C(O)NHR^{41}$, $NR^{41}C(O)N(R^{41})_2$, $C(O)NH_2$, $C(O)NHR^{41}$, $C(O)N(R^{41})_2$, $C(O)NHOH$, $C(O)NHOR^{41}$, $C(O)NHSO_2R^{41}$, $C(O)NR^{41}SO_2R^{41}$, $SO_2NH_2$, $SO_2NHR^{41}$, $SO_2N(R^{41})_2$, C(O)H, C(O)OH, $C(N)NH_2$, $C(N)NHR^{41}$, $C(N)N(R^{41})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{41}$ is $R^{42}$, $R^{43}$, $R^{44}$ or $R^{45}$;

$R^{42}$ is phenyl, which is unfused or fused with benzene, heteroarene or $R^{42A}$; $R^{42A}$ is cycloalkane, cycloalkene, heterocycloalkane or heterocycloalkene;

$R^{43}$ is heteroaryl, which is unfused or fused with benzene, heteroarene or $R^{43A}$; $R^{43A}$ is cycloalkane, cycloalkene, heterocycloalkane or heterocycloalkene;

$R^{44}$ is cycloalkyl, cycloalkenyl, heterocycloalkyl, or heterocycloalkenyl, each of which is unfused or fused with benzene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $SR^{46}$, $S(O)R^{46}$, $SO_2R^{46}$, $C(O)R^{46}$, $C(O)OR^{46}$, $OC(O)R^{46}$, $OC(O)OR^{46}$, $NH_2$, $NHR^{46}$, $N(R^{46})_2$, $NHC(O)R^{46}$, $NR^{46}C(O)R^{46}$, $NHS(O)_2R^{46}$, $NR^{46}S(O)_2R^{46}$, $NHC(O)OR^{46}$, $NR^{46}C(O)OR^{46}$, $NHC(O)NH_2$, $NHC(O)NHR^{46}$, $NHC(O)N(R^{46})_2$, $NR^{46}C(O)NHR^{46}$, $NR^{46}C(O)N(R^{46})_2$, $C(O)NH_2$, $C(O)NHR^{46}$, $C(O)N(R^{46})_2$, $C(O)NHOH$, $C(O)NHOR^{46}$, $C(O)NHSO_2R^{46}$, $C(O)NR^{46}SO_2R^{46}$, $SO_2NH_2$, $SO_2NHR^{46}$, $SO_2N(R^{46})_2$, C(O)H, C(O)OH, $C(N)NH_2$, $C(N)NHR^{46}$, $C(N)N(R^{46})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{46}$ is alkyl, alkenyl, alkynyl, $R^{47}$, $R^{48}$ or $R^{49}$;

$R^{47}$ is phenyl, which is unfused or fused with benzene, heteroarene or $R^{47A}$; $R^{47A}$ is cycloalkane, cycloalkene, heterocycloalkane or heterocycloalkene;

$R^{48}$ is heteroaryl, which is unfused or fused with benzene, heteroarene or $R^{48A}$; $R^{48A}$ is cycloalkane, cycloalkene, heterocycloalkane or heterocycloalkene;

$R^{49}$ is cycloalkyl, cycloalkenyl, heterocycloalkyl, or heterocycloalkenyl, each of which is unfused or fused with benzene, heteroarene or $R^{49A}$; $R^{49A}$ is cycloalkane, cycloalkene, heterocycloalkane or heterocycloalkene;

the moieties represented by $R^{42}$, $R^{43}$, $R^{44}$, $R^{47}$, $R^{48}$, and $R^{49}$ are independently unsubstituted or substituted with one or more independently selected $R^{50}$, $OR^{50}$, $SR^{50}$, $S(O)R^{50}$, $SO_2R^{50}$, $C(O)R^{50}$, $C(O)OR^{50}$, $OC(O)R^{50}$, $OC(O)OR^{50}$, $NH_2$, $NHR^{50}$, $N(R^{50})_2$, $NHC(O)R^{50}$, $NR^{50}C(O)R^{50}$, $NHS(O)_2R^{50}$, $NR^{50}S(O)_2R^{50}$, $NHC(O)OR^{50}$, $NR^{50}C(O)OR^{50}$, $NHC(O)NH_2$, $NHC(O)NHR^{50}$, $NHC(O)N(R^{50})_2$, $NR^{50}C(O)NHR^{50}$, $NR^{50}C(O)N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{50}SO_2R^{50}$, $SO_2NH_2$, $SO_2NHR^{50}$, $SO_2N(R^{50})_2$, C(O)H, C(O)OH, $C(N)NH_2$, $C(N)NHR^{50}$, $C(N)N(R^{50})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl, which is unfused or fused with benzene, heteroarene or $R^{51A}$; $R^{51A}$ is cycloalkane, cycloalkene, heterocycloalkane or heterocycloalkene;

R$^{52}$ is heteroaryl, which is unfused or fused with benzene, heteroarene or R$^{52A}$; R$^{52A}$ is cycloalkane, cycloalkene, heterocycloalkane or heterocycloalkene;

R$^{53}$ is cycloalkyl, cycloalkenyl, heterocycloalkyl, or heterocycloalkenyl, each of which is unfused or fused with benzene, heteroarene or R$^{53A}$; R$^{53A}$ is cycloalkane, cycloalkene, heterocycloalkane or heterocycloalkene;

R$^{54}$ is alkyl, alkenyl or alkynyl, each of which is unsubstituted or substituted with one or two or three independently selected R$^{55}$, OR$^{55}$, SR$^{55}$, S(O)R$^{55}$, SO$_2$R$^{55}$, C(O)R$^{55}$, C(O)OR$^{55}$, OC(O)R$^{55}$, OC(O)OR$^{55}$, NH$_2$, NHR$^{55}$, N(R$^{55}$)$_2$, NHC(O)R$^{55}$, NR$^{55}$C(O)R$^{55}$, NHS(O)$_2$R$^{55}$, NR$^{55}$S(O)$_2$R$^{55}$, NHC(O)OR$^{55}$, NR$^{55}$C(O)OR$^{55}$, NHC(O)NH$_2$, NHC(O)NHR$^{55}$, NHC(O)N(R$^{55}$)$_2$, NR$^{55}$C(O)NHR$^{55}$, NR$^{55}$C(O)N(R$^{55}$)$_2$, C(O)NH$_2$, C(O)NHR$^{55}$, C(O)N(R$^{55}$)$_2$, C(O)NHOH, C(O)NHOR$^{55}$, C(O)NHSO$_2$R$^{55}$, C(O)NR$^{55}$SO$_2$R$^{55}$, SO$_2$NH$_2$, SO$_2$NHR$^{55}$, SO$_2$N(R$^{55}$)$_2$, C(O)H, C(O)OH, C(N)NH$_2$, C(N)NHR$^{55}$, C(N)N(R$^{55}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{55}$ is alkyl, alkenyl, alkynyl, phenyl, heteroaryl, cycloalkyl, cycloalkenyl, heterocycloalkyl, or heterocycloalkenyl;

wherein each foregoing cyclic moiety is independently unsubstituted, further unsubstituted, substituted or further substituted with one or more independently selected R$^{57}$, OR$^{57}$, SR$^{57}$, S(O)R$^{57}$, SO$_2$R$^{57}$, C(O)R$^{57}$, C(O)OR$^{57}$, OC(O)R$^{57}$, OC(O)OR$^{57}$, NH$_2$, NHR$^{57}$, N(R$^{57}$)$_2$, NHC(O)R$^{57}$, NR$^{57}$C(O)R$^{57}$, NHS(O)$_2$R$^{57}$, NR$^{57}$S(O)$_2$R$^{57}$, NHC(O)OR$^{57}$, NR$^{57}$C(O)OR$^{57}$, NHC(O)NH$_2$, NHC(O)NHR$^{57}$, NHC(O)N(R$^{57}$)$_2$, NR$^{57}$C(O)NHR$^{57}$, NR$^{57}$C(O)N(R$^{57}$)$_2$, C(O)NH$_2$, C(O)NHR$^{57}$, C(O)N(R$^{57}$)$_2$, C(O)NHOH, C(O)NHOR$^{57}$, C(O)NHSO$_2$R$^{57}$, C(O)NR$^{57}$SO$_2$R$^{57}$, SO$_2$NH$_2$, SO$_2$NHR$^{57}$, SO$_2$N(R$^{57}$)$_2$, C(O)H, C(O)OH, C(N)NH$_2$, C(N)NHR$^{57}$, C(N)N(R$^{57}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{57}$ is R$^{58}$, R$^{59}$, R$^{60}$ or R$^{61}$;

R$^{58}$ is phenyl, which is unfused or fused with benzene, heteroarene or R$^{58A}$; R$^{58A}$ is cycloalkane, cycloalkene, heterocycloalkane or heterocycloalkene;

R$^{59}$ is heteroaryl, which is unfused or fused with benzene, heteroarene or R$^{59A}$; R$^{59A}$ is cycloalkane, cycloalkene, heterocycloalkane or heterocycloalkene;

R$^{60}$ is cycloalkyl, cycloalkenyl, heterocycloalkyl or heterocycloalkenyl, each of which is unfused or fused with benzene, heteroarene or R$^{60A}$; R$^{60A}$ is cycloalkane, cycloalkene, heterocycloalkane or heterocycloalkene;

R$^{61}$ is alkyl, alkenyl, or alkynyl, each of which is unsubstituted or substituted with one or two or three independently selected R$^{62}$, OR$^{62}$, SR$^{62}$, S(O)R$^{62}$, SO$_2$R$^{62}$, C(O)R$^{62}$, C(O)OR$^{62}$, OC(O)R$^{62}$, OC(O)OR$^{62}$, NH$_2$, NHR$^{62}$, N(R$^{62}$)$_2$, NHC(O)R$^{62}$, NR$^{62}$C(O)R$^{62}$, NHS(O)$_2$R$^{62}$, NR$^{62}$S(O)$_2$R$^{62}$, NHC(O)OR$^{62}$, NR$^{62}$C(O)OR$^{62}$, NHC(O)NH$_2$, NHC(O)NHR$^{62}$, NHC(O)N(R$^{62}$)$_2$, NR$^{62}$C(O)NHR$^{62}$, NR$^{62}$C(O)N(R$^{62}$)$_2$, C(O)NH$_2$, C(O)NHR$^{62}$, C(O)N(R$^{62}$)$_2$, C(O)NHOH, C(O)NHOR$^{62}$, C(O)NHSO$_2$R$^{62}$, C(O)NR$^{62}$SO$_2$R$^{62}$, SO$_2$NH$_2$, SO$_2$NHR$^{62}$, SO$_2$N(R$^{62}$)$_2$, C(O)H, C(O)OH, C(N)NH$_2$, C(N)NHR$^{62}$, C(N)N(R$^{62}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{62}$ is R$^{63}$, R$^{64}$, R$^{65}$ or R$^{66}$;

R$^{63}$ is phenyl, which is unfused or fused with benzene, heteroarene or R$^{63A}$; R$^{63A}$ is cycloalkane, cycloalkene, heterocycloalkane or heterocycloalkene;

R$^{64}$ is heteroaryl, which is unfused or fused with benzene, heteroarene or R$^{64A}$; R$^{64A}$ is cycloalkane, cycloalkene, heterocycloalkane or heterocycloalkene;

R$^{65}$ is cycloalkyl, cycloalkenyl, heterocycloalkyl or heterocycloalkenyl, each of which is unfused or fused with benzene, heteroarene or R$^{65A}$; R$^{65A}$ is cycloalkane, cycloalkene, heterocycloalkane or heterocycloalkene;

R$^{66}$ is alkyl, alkenyl, or alkenyl, each of which is unsubstituted or substituted with one or two or three independently selected R$^{67}$, OR$^{67}$, SR$^{67}$, S(O)R$^{67}$, SO$_2$R$^{67}$, C(O)R$^{67}$, C(O)OR$^{67}$, OC(O)R$^{67}$, OC(O)OR$^{67}$, NH$_2$, NHR$^{67}$, N(R$^{67}$)$_2$, NHC(O)R$^{67}$, NR$^{67}$C(O)R$^{67}$, NHS(O)$_2$R$^{67}$, NR$^{67}$S(O)$_2$R$^{67}$, NHC(O)OR$^{67}$, NR$^{67}$C(O)OR$^{67}$, NHC(O)NH$_2$, NHC(O)NHR$^{67}$, NHC(O)N(R$^{67}$)$_2$, NR$^{67}$C(O)NHR$^{67}$, NR$^{67}$C(O)N(R$^{67}$)$_2$, C(O)NH$_2$, C(O)NHR$^{67}$, C(O)N(R$^{67}$)$_2$, C(O)NHOH, C(O)NHOR$^{67}$, C(O)NHSO$_2$R$^{67}$, C(O)NR$^{67}$SO$_2$R$^{67}$, SO$_2$NH$_2$, SO$_2$NHR$^{67}$, SO$_2$N(R$^{67}$)$_2$, C(O)H, C(O)OH, C(N)NH$_2$, C(N)NHR$^{67}$, C(N)N(R$^{67}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{67}$ is alkyl, alkenyl, alkynyl, phenyl, heteroaryl, cycloalkyl, cycloalkenyl, heterocycloalkyl or heterocycloalkenyl;

wherein the moieties represented by R$^{58}$, R$^{59}$, R$^{60}$, R$^{63}$, R$^{64}$, R$^{65}$, and R$^{67}$ are unsubstituted or substituted with one or more independently selected R$^{68}$, OR$^{68}$, SR$^{68}$, S(O)R$^{68}$, SO$_2$R$^{68}$, C(O)R$^{68}$, C(O)OR$^{68}$, OC(O)R$^{68}$, OC(O)OR$^{68}$, NH$_2$, NHR$^{68}$, N(R$^{68}$)$_2$, NHC(O)R$^{68}$, NR$^{68}$C(O)R$^{68}$, NHS(O)$_2$ R$^{68}$, NR$^{68}$S(O)$_2$R$^{68}$, NHC(O)OR$^{68}$, NR$^{68}$C(O)OR$^{68}$, NHC(O)NH$_2$, NHC(O)NHR$^{68}$, NHC(O)N(R$^{68}$)$_2$, NR$^{68}$C(O)NHR$^{68}$, NR$^{68}$C(O)N(R$^{68}$)$_2$, C(O)NH$_2$, C(O)NHR$^{68}$, C(O)N(R$^{68}$)$_2$, C(O)NHOH, C(O)NHOR$^{68}$, C(O)NHSO$_2$R$^{68}$, C(O)NR$^{68}$SO$_2$R$^{68}$, SO$_2$NH$_2$, SO$_2$NHR$^{68}$, SO$_2$N(R$^{68}$)$_2$, C(O)H, C(O)OH, C(N)NH$_2$, C(N)NHR$^{68}$, C(N)N(R$^{68}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{68}$ is R$^{69}$, R$^{70}$, R$^{71}$ or R$^{72}$;

R$^{69}$ is phenyl, which is unfused or fused with benzene, heteroarene or R$^{69A}$; R$^{69A}$ is cycloalkane, cycloalkene, heterocycloalkane or heterocycloalkene;

R$^{70}$ is heteroaryl, which is unfused or fused with benzene, heteroarene or R$^{70A}$; R$^{70A}$ is cycloalkane, cycloalkene, heterocycloalkane or heterocycloalkene;

R$^{71}$ is cycloalkyl, cycloalkenyl, heterocycloalkyl or heterocycloalkenyl, each of which is unfused or fused with benzene, heteroarene or R$^{71A}$; R$^{71A}$ is cycloalkane, cycloalkene, heterocycloalkane or heterocycloalkene;

R$^{72}$ is alkyl, alkenyl, or alkenyl, each of which is unsubstituted or substituted with one or two or three independently selected R$^{73}$, OR$^{73}$, SR$^{73}$, S(O)R$^{73}$, SO$_2$R$^{73}$, C(O)R$^{73}$, C(O)OR$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)NH$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO$_2$NH$_2$, SO$_2$NHR$^{73}$, SO$_2$N(R$^{73}$)$_2$, C(O)H, C(O)OH, C(N)NH$_2$, C(N)NHR$^{73}$, C(N)N(R$^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{73}$ is alkyl, alkenyl, alkenyl, phenyl, heteroaryl, cycloalkyl, cycloalkenyl, heterocycloalkyl, or heterocycloalkenyl; and the moieties represented by R$^{69}$, R$^{70}$, and R$^{71}$ are unsubstituted or substituted with one or more independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, CF$_3$, CF$_2$CF$_3$, OCF$_3$, OCF$_2$CF$_3$, F, Cl, Br or I substituents.

In another embodiment of Formula (I),

A$^1$ is furyl, imidazolyl, isothiazolyl, isoxazolyl, pyrazolyl, pyrrolyl, thiazolyl, thiadiazolyl, thienyl, triazolyl, heterocycloalkyl, or heterocycloalkenyl; each of which is unfused or fused with benzene, heteroarene or A$^{1A}$; A$^{1A}$ is heterocycloalkene;

wherein A$^1$ is unsubstituted or substituted with one or two or three or four or five independently selected R$^1$, OR$^1$, C(O)OR$^1$, NHR$^1$, N(R$^1$)$_2$, C(N)C(O)R$^1$, C(O)NHR$^1$, NHC(O)R$^1$, NR$^1$C(O)R$^1$, (O), NO$_2$, F, Cl, Br, I, CF$_3$;

R$^1$ is R$^2$, R$^3$, R$^4$ or R$^5$;
R$^2$ is phenyl;
R$^3$ is heteroaryl;
R$^4$ is heterocycloalkyl;
R$^5$ is alkyl, or alkenyl, each of which is unsubstituted or substituted R$^7$, SR$^7$, N(R$^7$)$_2$, NHC(O)R$^7$, F, Cl, Br or I substituents;
R$^7$ is R$^8$, R$^9$, R$^{10}$ or R$^{11}$;
R$^8$ is phenyl;
R$^9$ is heteroaryl;
R$^{10}$ is heterocycloalkyl;
R$^{11}$ is alkyl;
Z$^1$ is R$^{26}$;
Z$^2$ is R$^{30}$;
L$^1$ is a R$^{37}$;
R$^{26}$ is phenylene;
R$^{30}$ is heterocycloalkylene;
R$^{37}$ is R$^{37A}$;
R$^{37A}$ is alkylene, or alkenylene, each of which is unsubstituted or substituted with R$^{37B}$;
R$^{37B}$ is phenyl;
Z$^3$ is R$^{38}$, or R$^{40}$;
R$^{38}$ is phenyl;
R$^{40}$ is cycloalkyl, or cycloalkenyl;
wherein the moieties represented by R$^{26}$ and R$^{27}$ are unsubstituted or substituted with OR$^{41}$;
R$^{41}$ is R$^{42}$, or R$^{43}$;
R$^{42}$ is phenyl, which is unfused or fused with heteroarene;
R$^{43}$ is heteroaryl, which is unfused or fused with heteroarene;
wherein each foregoing cyclic moiety is independently unsubstituted, further unsubstituted, substituted or further substituted with one or more independently selected R$^{57}$, OR$^{57}$, C(O)OR$^{57}$, F, Cl, Br or I substituents;
R$^{57}$ is R$^{58}$, or R$^{61}$;
R$^{58}$ is phenyl;
R$^{61}$ is alkyl; and
wherein the moieties represented by R$^{58}$, are unsubstituted or substituted with one or more independently selected F, Cl, Br or I substituents.

In one embodiment of Formula (I), A$^1$ is furyl, imidazolyl, isothiazolyl, isoxazolyl, pyrazolyl, pyrrolyl, thiazolyl, thiadiazolyl, thienyl, triazolyl, heterocycloalkyl, or heterocycloalkenyl; each of which is unfused or fused with benzene, heteroarene or A$^{1A}$; and A$^{1A}$ is heterocycloalkene. In another embodiment of Formula (I), A$^1$ is furyl. In another embodiment of Formula (I), A$^1$ is imidazolyl. In another embodiment of Formula (I), A$^1$ is isothiazolyl. In another embodiment of Formula (I), A$^1$ is isoxazolyl. In another embodiment of Formula (I), A$^1$ is pyrazolyl. In another embodiment of Formula (I), A$^1$ is pyrrolyl. In another embodiment of Formula (I), A$^1$ is thiazolyl. In another embodiment of Formula (I), A$^1$ is thiadiazolyl. In another embodiment of Formula (I), A$^1$ is thienyl. In another embodiment of Formula (I), A$^1$ is
In another embodiment of Formula (I), A$^1$ is triazolyl. In another embodiment of Formula (I), A$^1$ is heterocycloalkyl.

In another embodiment of Formula (I), A$^1$ is heterocycloalkenyl. In another embodiment of Formula (I), A$^1$ is piperidinyl. In another embodiment of Formula (I), A$^1$ is morpholinyl. In another embodiment of Formula (I), A$^1$ is dihydro-1,3,4-thiadiazol-2-yl. In another embodiment of Formula (I), A$^1$ is benzothien-2-yl. In another embodiment of Formula (I), A$^1$ is benzothiazol-2-yl. In another embodiment of Formula (I), A$^1$ is benzothiazol-2-yl. In another embodiment of Formula (I), A$^1$ is [1,2,4]triazolo[1,5-a]pyrimidin-2-yl. In another embodiment of Formula (I), A$^1$ is tetrahydrothien-3-yl. In another embodiment of Formula (I), A$^1$ is [1,2,4]triazolo[1,5-a]pyrimidin-2-yl. In another embodiment of Formula (I), A$^1$ is imidazo[2,1-b][1,3]thiazol-5-yl.

In one embodiment of Formula (I), A$^1$ is unsubstituted. In another embodiment of Formula (I), A$^1$ is substituted with one or two or three or four or five independently selected R$^1$, OR$^1$, C(O)OR$^1$, NHR$^1$, N(R$^1$)$_2$, C(N)C(O)R$^1$, C(O)NHR$^1$, NHC(O)R$^1$, NR$^1$C(O)R$^1$, (O), NO$_2$, F, Cl, Br, I, or CF$_3$. In one embodiment of Formula (I), A$^1$ is unsubstituted. In another embodiment of Formula (I), A$^1$ is substituted with NHR$^1$. In another embodiment of Formula (I), A$^1$ is substituted with NHR$^1$, and NO$_2$. In another embodiment of Formula (I), A$^1$ is substituted with NHR$^1$. In another embodiment of Formula (I), A$^1$ is substituted with NR$^1$C(O)R$^1$. In another embodiment of Formula (I), A$^1$ is substituted with N(R$^1$)$_2$. In another embodiment of Formula (I), A$^1$ is substituted with C(N)C(O)R$^1$, and R$^1$. In another embodiment of Formula (I), A$^1$ is substituted with NHC(O)R$^1$, and R$^1$. In another embodiment of Formula (I), A$^1$ is substituted with R$^1$. In another embodiment of Formula (I), A$^1$ is substituted with two independently selected R$^1$. In another embodiment of Formula (I), A$^1$ is substituted with Cl. In another embodiment of Formula (I), A$^1$ is substituted with CF$_3$. In another embodiment of Formula (I), A$^1$ is substituted with F. In another embodiment of Formula (I), A$^1$ is substituted with three independently selected R$^1$, and C(O)OR$^1$. In another embodiment of Formula (I), A$^1$ is substituted R$^1$, and C(O)OR$^1$. In another embodiment of Formula (I), A$^1$ is substituted R$^1$, and Cl. In another embodiment of Formula (I), A$^1$ is substituted R$^1$, and Br. In another embodiment of Formula (I), A$^1$ is substituted with three independently selected R$^1$. In another embodiment of Formula (I), A$^1$ is substituted with C(O)NHR$^1$. In another embodiment of Formula (I), A$^1$ is substituted with two independently selected R$^1$, and Cl. In another embodiment of Formula (I), A$^1$ is substituted with R$^1$, and NO$_2$. In another embodiment of Formula (I), A$^1$ is substituted NHR$^1$, and NO$_2$. In another embodiment of Formula (I), A$^1$ is substituted with (O). In another embodiment of Formula (I), A$^1$ is substituted with OR$^1$.

In one embodiment of Formula (I), R$^1$ is phenyl. In another embodiment of Formula (I), R$^1$ is pyrazolyl. In another embodiment of Formula (I), R$^1$ is morpholinyl. In another embodiment of Formula (I), R$^1$ is isoxazolyl. In another embodiment of Formula (I), R$^1$ is piperidinyl. In another embodiment of Formula (I), R$^1$ is alkyl, which is unsubstituted. In another embodiment of Formula (I), R$^1$ is alkyl, which is substituted with one or more R$^7$, SR$^7$, N(R$^7$)$_2$, NHC(O)R$^7$, or Cl.

In one embodiment of Formula (I), R$^7$ is phenyl. In another embodiment of Formula (I), R$^7$ is methyl. In another embodiment of Formula (I), R$^7$ is isopropyl. In another embodiment of Formula (I), R$^7$ is pyrrolinyl. In another embodiment of Formula (I), R$^7$ is morpholinyl. In another embodiment of Formula (I), R$^7$ is tetrahydropyranyl.

Still another embodiment pertains to compounds having Formula I, which are

4-[4-(cyclohexylmethyl)-4-methoxypiperidin-1-yl]-N-{[5-({(1R)-3-(dimethylamino)-1-[(phenylthio)methyl]propyl}amino)-4-nitrothien-2-yl]sulfonyl}benzamide;

N-{[5-({(1R)-3-(dimethylamino)-1-[(phenylthio)methyl]propyl}amino)-4-nitrothien-2-yl]sulfonyl}-4-[4-methoxy-4-(3-methylbenzyl)piperidin-1-yl]benzamide;

N-{[5-({(1R)-3-(dimethylamino)-1-[(phenylthio)methyl]propyl}amino)-4-nitrothien-2-yl]sulfonyl}-4-[4-(3,3-diphenylprop-2-enyl)piperazin-1-yl]benzamide;

4-{4-[(4'-chloro-1,1'-biphenyl-2-yl)methyl]piperazin-1-yl}-N-[(4-{[2-(phenylthio)ethyl]amino}piperidin-1-yl)sulfonyl]benzamide;

N-[(4-{acetyl[2-(phenylthio)ethyl]amino}piperidin-1-yl)sulfonyl]-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-(4-{methyl[2-(phenylthio)ethyl]amino}piperidin-1-yl)sulfonyl]benzamide;

4-{4-[(4'-chloro-1,1'-biphenyl-2-yl)methyl]piperazin-1-yl}-N-{[5-({(1R)-3-[isopropyl(methyl)amino]-1-[(phenylthio)methyl]propyl}amino)-4-nitrothien-2-yl]sulfonyl}benzamide;

4-(4-{[2-(4-chlorophenyl)cyclohex-1-en-1-yl]methyl}piperazin-1-yl)-N-{[5-({(1R)-3-[isopropyl(methyl)amino]-1-[(phenylthio)methyl]propyl}amino)-4-nitrothien-2-yl]sulfonyl}benzamide;

4-(4-{[2-(4-chlorophenyl)-5,5-dimethylcyclohex-1-en-1-yl]methyl}piperazin-1-yl)-N-{[5-({(1R)-3-[isopropyl(methyl)amino]-1-[(phenylthio)methyl]propyl}amino)-4-nitrothien-2-yl]sulfonyl}benzamide;

N-{[(5Z)-5-(acetylimino)-4-methyl-4,5-dihydro-1,3,4-thiadiazol-2-yl]sulfonyl}-4-{4-[(4'-chloro-1,1'-biphenyl-2-yl)methyl]piperazin-1-yl}benzamide;

N-{[2-(acetylamino)-4-methyl-1,3-thiazol-5-yl]sulfonyl}-4-{4-[(4'-chloro-1,1'-biphenyl-2-yl)methyl]piperazin-1-yl}benzamide;

N-({5-[(benzoylamino)methyl]thien-2-yl}sulfonyl)-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-[(6-chloroimidazo[2,1-b][1,3]thiazol-5-yl)sulfonyl]benzamide;

4-{4-[(4'-chloro-1,1'-biphenyl-2-yl)methyl]piperazin-1-yl}-N-(morpholin-4-ylsulfonyl)benzamide;

4-{4-[(4'-chloro-1,1'-biphenyl-2-yl)methyl]piperazin-1-yl}-N-[(2,4-dimethyl-1,3-thiazol-5-yl)sulfonyl]benzamide;

4-{4-[(4'-chloro-1,1'-biphenyl-2-yl)methyl]piperazin-1-yl}-N-{[4-phenyl-5-(trifluoromethyl)thien-3-yl]sulfonyl}benzamide;

4-{4-[(4'-chloro-1,1'-biphenyl-2-yl)methyl]piperazin-1-yl}-N-[(5-fluoro-3-methyl-1-benzothien-2-yl)sulfonyl]benzamide;

N-(1,3-benzothiazol-2-ylsulfonyl)-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-(thien-2-ylsulfonyl)benzamide;

4-{4-[(4'-chloro-1,1'-biphenyl-2-yl)methyl]piperazin-1-yl}-N-[(5,7-dimethyl[1,2,4]triazolo[1,5-a]pyrimidin-2-yl)sulfonyl]benzamide;

ethyl 4-{[(4-{4-[(4'-chloro-1,1'-biphenyl-2-yl)methyl]piperazin-1-yl}benzoyl)amino]sulfonyl}-5-methyl-1,2-diphenyl-1H-pyrrole-3-carboxylate;

methyl 5-{[(4-{4-[(4'-chloro-1,1'-biphenyl-2-yl)methyl]piperazin-1-yl}benzoyl)amino]sulfonyl}-1-methyl-1H-pyrrole-2-carboxylate;

4-{4-[(4'-chloro-1,1'-biphenyl-2-yl)methyl]piperazin-1-yl}-N-{[5-(1,3-dimethyl-1H-pyrazol-5-yl)isoxazol-4-yl]sulfonyl}benzamide;

4-{4-[(4'-chloro-1,1'-biphenyl-2-yl)methyl]piperazin-1-yl}-N-[(4-chloro-3-methylisothiazol-5-yl)sulfonyl]benzamide;

N-[(5-bromo-3-methyl-1-benzothien-2-yl)sulfonyl]-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-({5-[(E)-2-(1,2,4-oxadiazol-3-yl)vinyl]thien-2-yl}sulfonyl)benzamide;

4-{4-[(4'-chloro-1,1'-biphenyl-2-yl)methyl]piperazin-1-yl}-N-{[1-(2-chloroethyl)-3,5-dimethyl-1H-pyrazol-4-yl]sulfonyl}benzamide;

5-{[(4-{4-[(4'-chloro-1,1'-biphenyl-2-yl)methyl]piperazin-1-yl}benzoyl)amino]sulfonyl}-N-(1-ethylpropyl)-1,3,4-thiadiazole-2-carboxamide;

4-{4-[(4'-chloro-1,1'-biphenyl-2-yl)methyl]piperazin-1-yl}-N-[(5-chloro-1,3-dimethyl-1H-pyrazol-4-yl)sulfonyl]benzamide;

4-{4-[(4'-chloro-1,1'-biphenyl-2-yl)methyl]piperazin-1-yl}-N-[(4-nitro-5-piperidin-1-ylthien-2-yl)sulfonyl]benzamide;

4-{4-[(4'-chloro-1,1'-biphenyl-2-yl)methyl]piperazin-1-yl}-N-[(5-isoxazol-5-yl-2-furyl)sulfonyl]benzamide;

4-{4-[(4'-chloro-1,1'-biphenyl-2-yl)methyl]piperazin-1-yl}-N-[(3,5-dimethylisoxazol-4-yl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({4-nitro-5-[(3-pyrrolidin-1-ylpropyl)amino]thien-2-yl}sulfonyl)benzamide;

4-(4-{[2-(4-chlorophenyl)-4,4-dimethylcyclohex-1-en-1-yl]methyl}piperazin-1-yl)-N-[(5-{[3-(dimethylamino)propyl]amino}-4-nitrothien-2-yl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({5-[(3-morpholin-4-ylpropyl)amino]-4-nitrothien-2-yl}sulfonyl)benzamide;

N-{[5-({(1R)-3-(dimethylamino)-1-[(phenylthio)methyl]propyl}amino)-4-nitrothien-2-yl]sulfonyl}-4-{4-[2-(trifluoromethyl)benzylidene]piperidin-1-yl}benzamide;

4-{4-[(4'-chloro-1,1'-biphenyl-2-yl)methylene]piperidin-1-yl}-N-[(1,1-dioxidotetrahydrothien-3-yl)sulfonyl]benzamide;

4-{4-[(4'-chloro-1,1'-biphenyl-2-yl)methylene]piperidin-1-yl}-N-[(5-chloro-3-methyl-1-benzothien-2-yl)sulfonyl]benzamide;

4-{4-[(4'-chloro-1,1'-biphenyl-2-yl)methyl]piperazin-1-yl}-N-[(5-chloro-3-methyl-1-benzothien-2-yl)sulfonyl]-2-phenoxybenzamide;

2-(3-chlorophenoxy)-4-(4-{[2-(4-chlorophenyl)-4,4-dimethylcyclohex-1-en-1-yl]methyl}piperazin-1-yl)-N-[(5,7-dimethyl[1,2,4]triazolo[1,5-a]pyrimidin-2-yl)sulfonyl]benzamide;

4-(4-{[2-(4-chlorophenyl)-4,4-dimethylcyclohex-1-en-1-yl]methyl}piperazin-1-yl)-N-[(5,7-dimethyl[1,2,4]triazolo[1,5-a]pyrimidin-2-yl)sulfonyl]-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-[(5,7-dimethyl[1,2,4]triazolo[1,5-a]pyrimidin-2-yl)sulfonyl]benzamide;

tert-butyl (2S)-2-{[(5-{[4-(4-{[2-(4-chlorophenyl)-4,4-dimethylcyclohex-1-en-1-yl]methyl}piperazin-1-yl)-2-(1H- pyrrolo[2,3-b]pyridin-5-yloxy)benzoyl]sulfamoyl}-4-methyl-1,3-thiazol-2-yl)oxy]methyl}morpholine-4-carboxylate;

tert-butyl (2S)-2-{[(5-{[2-(1H-benzimidazol-4-yloxy)-4-(4-{[2-(4-chlorophenyl)-4,4-dimethylcyclohex-1-en-1-yl]methyl}piperazin-1-yl)benzoyl]sulfamoyl}-4-methyl-1,3-thiazol-2-yl)oxy]methyl}morpholine-4-carboxylate;

4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-pyrrolo[2,3-b]pyridin-5-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)benzamide;

tert-butyl (2S)-2-{[(5-{[4-(4-{[2-(4-chlorophenyl)-4,4-dimethylcyclohex-1-en-1-yl]methyl}piperazin-1-yl)-2-(1H-indazol-4-yloxy)benzoyl]sulfamoyl}-4-methyl-1,3-thiazol-2-yl)oxy]methyl}morpholine-4-carboxylate;

4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-indazol-4-yloxy)benzamide;

and therapeutically acceptable salts, prodrugs, salts of prodrugs and metabolites thereof.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (II)

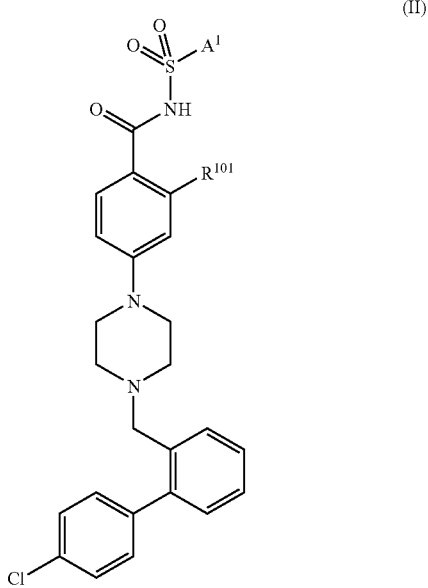

(II)

wherein $R^{101}$ is H or is as described for substituents on $R^{26}$, and $A^1$ is as described in Formula (I).

In one embodiment of Formula (II), $A^1$ is furyl, imidazolyl, isothiazolyl, isoxazolyl, pyrazolyl, pyrrolyl, thiazolyl, thiadiazolyl, thienyl, triazolyl, heterocycloalkyl, or heterocycloalkenyl; each of which is unfused or fused with benzene, heteroarene or $A^{1A}$; and $A^{1A}$ is heterocycloalkene. In another embodiment of Formula (II), $A^1$ is furyl. In another embodiment of Formula (II), $A^1$ is imidazolyl. In another embodiment of Formula (II), $A^1$ is isothiazolyl. In another embodiment of Formula (II), $A^1$ is isoxazolyl. In another embodiment of Formula (II), $A^1$ is pyrazolyl. In another embodiment of Formula (II), $A^1$ is pyrrolyl. In another embodiment of Formula (II), $A^1$ is thiazolyl. In another embodiment of Formula (II), $A^1$ is thiadiazolyl. In another embodiment of Formula (II), $A^1$ is thienyl. In another embodiment of Formula (II), $A^1$ is In another embodiment of Formula (II), $A^1$ is triazolyl. In another embodiment of Formula (II), $A^1$ is heterocycloalkyl. In another embodiment of Formula (II), $A^1$ is heterocycloalkenyl. In another embodiment of Formula (II), $A^1$ is piperidinyl. In another embodiment of Formula (II), $A^1$ is morpholinyl. In another embodiment of Formula (II), $A^1$ is dihydro-1,3,4-thiadiazol-2-yl. In another embodiment of Formula (II), $A^1$ is benzothien-2-yl. In another embodiment of Formula (II), $A^1$ is benzothiazol-2-yl. In another embodiment of Formula (II), $A^1$ is benzothiazol-2-yl. In another embodiment of Formula (II), $A^1$ is [1,2,4]triazolo[1,5-a]pyrimidin-2-yl. In another embodiment of Formula (II), $A^1$ is tetrahydrothien-3-yl. In another embodiment of Formula (II), $A^1$ is [1,2,4]triazolo[1,5-a]pyrimidin-2-yl. In another embodiment of Formula (II), $A^1$ is imidazo[2,1-b][1,3]thiazol-5-yl.

In one embodiment of Formula (II), $A^1$ is unsubstituted. In another embodiment of Formula (II), $A^1$ is substituted with one or two or three or four or five independently selected $R^1$, $OR^1$, $C(O)OR^1$, $NHR^1$, $N(R^1)_2$, $C(N)C(O)R^1$, $C(O)NHR^1$, $NHC(O)R^1$, $NR^1C(O)R^1$, (O), $NO_2$, F, Cl, Br, I, or $CF_3$. In one embodiment of Formula (II), $A^1$ is unsubstituted. In another embodiment of Formula (II), $A^1$ is substituted with $NHR^1$. In another embodiment of Formula (II), $A^1$ is substituted with $NHR^1$, and $NO_2$. In another embodiment of Formula (II), $A^1$ is substituted with $NHR^1$. In another embodiment of Formula (II), $A^1$ is substituted with $NR^1C(O)R^1$. In another embodiment of Formula (II), $A^1$ is substituted with $N(R^1)_2$. In another embodiment of Formula (II), $A^1$ is substituted with $C(N)C(O)R^1$, and $R^1$. In another embodiment of Formula (II), $A^1$ is substituted with $NHC(O)R^1$, and $R^1$. In another embodiment of Formula (II), $A^1$ is substituted with $R^1$. In another embodiment of Formula (II), $A^1$ is substituted with two independently selected $R^1$. In another embodiment of Formula (II), $A^1$ is substituted with Cl. In another embodiment of Formula (II), $A^1$ is substituted with $CF_3$. In another embodiment of Formula (II), $A^1$ is substituted with F. In another embodiment of Formula (II), $A^1$ is substituted with three independently selected $R^1$, and $C(O)OR^1$. In another embodiment of Formula (II), $A^1$ is substituted $R^1$, and $C(O)OR^1$. In another embodiment of Formula (II), $A^1$ is substituted $R^1$, and Cl. In another embodiment of Formula (II), $A^1$ is substituted $R^1$, and Br. In another embodiment of Formula (II), $A^1$ is substituted with three independently selected $R^1$. In another embodiment of Formula (II), $A^1$ is substituted with $C(O)NHR^1$. In another embodiment of Formula (II), $A^1$ is substituted with two independently selected $R^1$, and Cl. In another embodiment of Formula (II), $A^1$ is substituted with $R^1$, and $NO_2$. In another embodiment of Formula (II), $A^1$ is substituted $NHR^1$, and $NO_2$. In another embodiment of Formula (II), $A^1$ is substituted with (O). In another embodiment of Formula (II), $A^1$ is substituted with $OR^1$.

In one embodiment of Formula (II), $R^1$ is phenyl. In another embodiment of Formula (II), $R^1$ is pyrazolyl. In another embodiment of Formula (II), $R^1$ is morpholinyl. In another embodiment of Formula (II), $R^1$ is isoxazolyl. In another embodiment of Formula (II), $R^1$ is piperidinyl. In another embodiment of Formula (II), $R^1$ is alkyl, which is unsubstituted. In another embodiment of Formula (II), $R^1$ is alkyl, which is substituted with one or more $R^7$, $SR^7$, $N(R^7)_2$, $NHC(O)R^7$, or Cl.

In one embodiment of Formula (II), $R^7$ is phenyl. In another embodiment of Formula (II), $R^7$ is methyl. In another embodiment of Formula (II), $R^7$ is isopropyl. In another embodiment of Formula (II), $R^7$ is pyrrolinyl. In another embodiment of Formula (II), $R^7$ is morpholinyl. In another embodiment of Formula (II), $R^7$ is tetrahydropyranyl.

Still another embodiment pertains to compounds having Formula II, which are

4-{4-[(4'-chloro-1,1'-biphenyl-2-yl)methyl]piperazin-1-yl}-N-[(4-{[2-(phenylthio)ethyl]amino}piperidin-1-yl)sulfonyl]benzamide;

N-[(4-{acetyl[2-(phenylthio)ethyl]amino}piperidin-1-yl)sulfonyl]-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-(4-{methyl[2-(phenylthio)ethyl]amino}piperidin-1-yl)sulfonyl]benzamide;

4-{4-[(4'-chloro-1,1'-biphenyl-2-yl)methyl]piperazin-1-yl}-N-{[5-({(1R)-3-[isopropyl(methyl)amino]-1-[(phenylthio)methyl]propyl}amino)-4-nitrothien-2-yl]sulfonyl}benzamide;

N-{[(5Z)-5-(acetylimino)-4-methyl-4,5-dihydro-1,3,4-thiadiazol-2-yl]sulfonyl}-4-{4-[(4'-chloro-1,1'-biphenyl-2-yl)methyl]piperazin-1-yl}benzamide;

N-{[2-(acetylamino)-4-methyl-1,3-thiazol-5-yl]sulfonyl}-4-{4-[(4'-chloro-1,1'-biphenyl-2-yl)methyl]piperazin-1-yl}benzamide;

N-({5-[(benzoylamino)methyl]thien-2-yl}sulfonyl)-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-[(6-chloroimidazo[2,1-b][1,3]thiazol-5-yl)sulfonyl]benzamide;

4-{4-[(4'-chloro-1,1'-biphenyl-2-yl)methyl]piperazin-1-yl}-N-(morpholin-4-ylsulfonyl)benzamide;

4-{4-[(4'-chloro-1,1'-biphenyl-2-yl)methyl]piperazin-1-yl}-N-[(2,4-dimethyl-1,3-thiazol-5-yl)sulfonyl]benzamide;

4-{4-[(4'-chloro-1,1'-biphenyl-2-yl)methyl]piperazin-1-yl}-N-{[4-phenyl-5-(trifluoromethyl)thien-3-yl]sulfonyl}benzamide;

4-{4-[(4'-chloro-1,1'-biphenyl-2-yl)methyl]piperazin-1-yl}-N-[(5-fluoro-3-methyl-1-benzothien-2-yl)sulfonyl]benzamide;

N-(1,3-benzothiazol-2-ylsulfonyl)-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-(thien-2-ylsulfonyl)benzamide;

4-{4-[(4'-chloro-1,1'-biphenyl-2-yl)methyl]piperazin-1-yl}-N-[(5,7-dimethyl[1,2,4]triazolo[1,5-a]pyrimidin-2-yl)sulfonyl]benzamide;

ethyl 4-{[(4-{4-[(4'-chloro-1,1'-biphenyl-2-yl)methyl]piperazin-1-yl}benzoyl)amino]sulfonyl}-5-methyl-1,2-diphenyl-1H-pyrrole-3-carboxylate;

methyl 5-{[(4-{4-[(4'-chloro-1,1'-biphenyl-2-yl)methyl]piperazin-1-yl}benzoyl)amino]sulfonyl}-1-methyl-1H-pyrrole-2-carboxylate;

4-{4-[(4'-chloro-1,1'-biphenyl-2-yl)methyl]piperazin-1-yl}-N-{[5-(1,3-dimethyl-1H-pyrazol-5-yl)isoxazol-4-yl]sulfonyl}benzamide;

4-{4-[(4'-chloro-1,1'-biphenyl-2-yl)methyl]piperazin-1-yl}-N-[(4-chloro-3-methylisothiazol-5-yl)sulfonyl]benzamide;

N-[(5-bromo-3-methyl-1-benzothien-2-yl)sulfonyl]-4-{4-[(4'-chloro-1,1'-biphenyl-2-yl)methyl]piperazin-1-yl}benzamide;

4-{4-[(4'-chloro-1,1'-biphenyl-2-yl)methyl]piperazin-1-yl}-N-({5-[(E)-2-(1,2,4-oxadiazol-3-yl)vinyl]thien-2-yl}sulfonyl)benzamide;

4-{4-[(4'-chloro-1,1'-biphenyl-2-yl)methyl]piperazin-1-yl}-N-{[1-(2-chloroethyl)-3,5-dimethyl-1H-pyrazol-4-yl]sulfonyl}benzamide;

5-{[(4-{4-[(4'-chloro-1,1'-biphenyl-2-yl)methyl]piperazin-1-yl}benzoyl)amino]sulfonyl}-N-(1-ethylpropyl)-1,3,4-thiadiazole-2-carboxamide;

4-{4-[(4'-chloro-1,1'-biphenyl-2-yl)methyl]piperazin-1-yl}-N-[(5-chloro-1,3-dimethyl-1H-pyrazol-4-yl)sulfonyl]benzamide;

4-{4-[(4'-chloro-1,1'-biphenyl-2-yl)methyl]piperazin-1-yl}-N-[(4-nitro-5-piperidin-1-ylthien-2-yl)sulfonyl]benzamide;

4-{4-[(4'-chloro-1,1'-biphenyl-2-yl)methyl]piperazin-1-yl}-N-[(5-isoxazol-5-yl-2-furyl)sulfonyl]benzamide;

4-{4-[(4'-chloro-1,1'-biphenyl-2-yl)methyl]piperazin-1-yl}-N-[(3,5-dimethylisoxazol-4-yl)sulfonyl]benzamide;

4-{4-[(4'-chloro-1,1'-biphenyl-2-yl)methyl]piperazin-1-yl}-N-[(5-chloro-3-methyl-1-benzothien-2-yl)sulfonyl]-2-phenoxybenzamide;

and therapeutically acceptable salts, prodrugs, salts of prodrugs and metabolites thereof.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (III)

wherein $R^{101}$ is H or is as described for substituents on $R^{26}$, and $A^1$ is as described in Formula (I).

In one embodiment of Formula (III), $A^1$ is furyl, imidazolyl, isothiazolyl, isoxazolyl, pyrazolyl, pyrrolyl, thiazolyl, thiadiazolyl, thienyl, triazolyl, heterocycloalkyl, or heterocycloalkenyl; each of which is unfused or fused with benzene, heteroarene or $A^{1A}$; and $A^{1A}$ is heterocycloalkene. In another embodiment of Formula (III), $A^1$ is furyl. In another embodiment of Formula (III), $A^1$ is imidazolyl. In another embodiment of Formula (III), $A^1$ is isothiazolyl. In another embodiment of Formula (III), $A^1$ is isoxazolyl. In another embodiment of Formula (III), $A^1$ is pyrazolyl. In another embodiment of Formula (III), A¹ is pyrrolyl. In another embodiment of Formula (III), A¹ is thiazolyl. In another embodiment of Formula (III), A¹ is thiadiazolyl. In another embodiment of Formula (III), A¹ is thienyl. In another embodiment of Formula (III), A¹ is In another embodiment of Formula (III), A¹ is triazolyl. In another embodiment of Formula (III), A¹ is heterocycloalkyl. In another embodiment of Formula (III), A¹ is heterocycloalkenyl. In another embodiment of Formula (III), A¹ is piperidinyl. In another embodiment of Formula (III), A¹ is morpholinyl. In another embodiment of Formula (III), A¹ is dihydro-1,3,4-thiadiazol-2-yl. In another embodiment of Formula (III), A¹ is benzothien-2-yl. In another embodiment of Formula (III), A¹ is benzothiazol-2-yl. In another embodiment of Formula (III), A¹ is benzothiazol-2-yl. In another embodiment of Formula (III), A¹ is [1,2,4]triazolo[1,5-a]pyrimidin-2-yl. In another embodiment of Formula (III), A¹ is tetrahydrothien-3-yl. In another embodiment of Formula (III), A¹ is [1,2,4]triazolo[1,5-a]pyrimidin-2-yl. In another embodiment of Formula (III), A¹ is imidazo[2,1-b][1,3]thiazol-5-yl.

In one embodiment of Formula (III), A¹ is unsubstituted. In another embodiment of Formula (III), A¹ is substituted with one or two or three or four or five independently selected R¹, OR¹, C(O)OR¹, NHR¹, N(R¹)₂, C(N)C(O)R¹, C(O)NHR¹, NHC(O)R¹, NR¹C(O)R¹, (O), NO₂, F, Cl, Br, I, or CF₃. In one embodiment of Formula (III), A¹ is unsubstituted. In another embodiment of Formula (III), A¹ is substituted with NHR¹. In another embodiment of Formula (III), A¹ is substituted with NHR¹, and NO₂. In another embodiment of Formula (III), A¹ is substituted with NHR¹. In another embodiment of Formula (III), A¹ is substituted with NR¹C(O)R¹. In another embodiment of Formula (III), A¹ is substituted with N(R¹)₂. In another embodiment of Formula (III), A¹ is substituted with C(N)C(O)R¹, and R¹. In another embodiment of Formula (III), A¹ is substituted with NHC(O)R¹, and R¹. In another embodiment of Formula (III), A¹ is substituted with R¹. In another embodiment of Formula (III), A¹ is substituted with two independently selected R¹. In another embodiment of Formula (III), A¹ is substituted with Cl. In another embodiment of Formula (III), A¹ is substituted with CF₃. In another embodiment of Formula (III), A¹ is substituted with F. In another embodiment of Formula (III), A¹ is substituted with three independently selected R¹, and C(O)OR¹. In another embodiment of Formula (III), A¹ is substituted R¹, and C(O)OR¹. In another embodiment of Formula (III), A¹ is substituted R¹, and Cl. In another embodiment of Formula (III), A¹ is substituted R¹, and Br. In another embodiment of Formula (III), A¹ is substituted with three independently selected R¹. In another embodiment of Formula (III), A¹ is substituted with C(O)NHR¹. In another embodiment of Formula (III), A¹ is substituted with two independently selected R¹, and Cl. In another embodiment of Formula (III), A¹ is substituted with R¹, and NO₂. In another embodiment of Formula (III), A¹ is substituted NHR¹, and NO₂. In another embodiment of Formula (III), A¹ is substituted with (O). In another embodiment of Formula (III), A¹ is substituted with OR¹.

In one embodiment of Formula (III), R¹ is phenyl. In another embodiment of Formula (III), R¹ is pyrazolyl. In another embodiment of Formula (III), R¹ is morpholinyl. In another embodiment of Formula (III), R¹ is isoxazolyl. In another embodiment of Formula (III), R¹ is piperidinyl. In another embodiment of Formula (III), R¹ is alkyl, which is unsubstituted. In another embodiment of Formula (III), R¹ is alkyl, which is substituted with one or more R⁷, SR⁷, N(R⁷)₂, NHC(O)R⁷, or Cl.

In one embodiment of Formula (III), R⁷ is phenyl. In another embodiment of Formula (III), R⁷ is methyl. In another embodiment of Formula (III), R⁷ is isopropyl. In another embodiment of Formula (III), R⁷ is pyrrolinyl. In another embodiment of Formula (III), R⁷ is morpholinyl. In another embodiment of Formula (III), R⁷ is tetrahydropyranyl.

Still another embodiment pertains to compounds having Formula III, which are 4-(4-{[2-(4-chlorophenyl)-5,5-dimethylcyclohex-1-en-1-yl]methyl}piperazin-1-yl)-N-{[5-({(1R)-3-[isopropyl(methyl)amino]-1-[(phenylthio)methyl]propyl}amino)-4-nitrothien-2-yl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-({4-nitro-5-[(3-pyrrolidin-1-ylpropyl)amino]thien-2-yl}sulfonyl)benzamide;

4-(4-{[2-(4-chlorophenyl)-4,4-dimethylcyclohex-1-en-1-yl]methyl}piperazin-1-yl)-N-[(5-{[3-(dimethylamino)propyl]amino}-4-nitrothien-2-yl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({5-[(3-morpholin-4-ylpropyl)amino]-4-nitrothien-2-yl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(5,7-dimethyl[1,2,4]triazolo[1,5-a]pyrimidin-2-yl)sulfonyl]benzamide;

4-(4-{[2-(4-chlorophenyl)-4,4-dimethylcyclohex-1-en-1-yl]methyl}piperazin-1-yl)-N-[(5,7-dimethyl[1,2,4]triazolo[1,5-a]pyrimidin-2-yl)sulfonyl]-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-[(5,7-dimethyl[1,2,4]triazolo[1,5-a]pyrimidin-2-yl)sulfonyl]benzamide;

tert-butyl (2S)-2-{[(5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-4-methyl-1,3-thiazol-2-yl)oxy]methyl}morpholine-4-carboxylate;

tert-butyl (2S)-2-{[(5-{[2-(1H-benzimidazol-4-yloxy)-4-(4-{[2-(4-chlorophenyl)-4,4-dimethylcyclohex-1-en-1-yl]methyl}piperazin-1-yl)benzoyl]sulfamoyl}-4-methyl-1,3-thiazol-2-yl)oxy]methyl}morpholine-4-carboxylate;

4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-pyrrolo[2,3-b]pyridin-5-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)benzamide;

tert-butyl (2S)-2-{[(5-{[4-(4-{[2-(4-chlorophenyl)-4,4-dimethylcyclohex-1-en-1-yl]methyl}piperazin-1-yl)-2-(1H-indazol-4-yloxy)benzoyl]sulfamoyl}-4-methyl-1,3-thiazol-2-yl)oxy]methyl}morpholine-4-carboxylate;

4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-indazol-4-yloxy)benzamide;

and therapeutically acceptable salts, prodrugs, salts of prodrugs and metabolites thereof.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (IV)

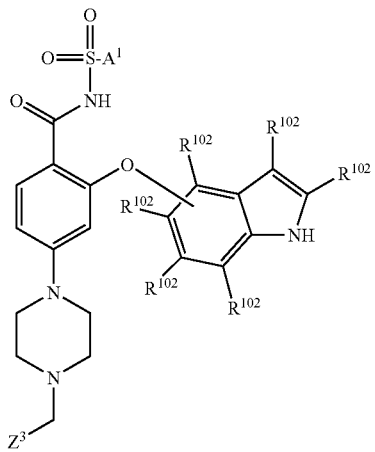

(IV)

wherein one $R^{102}$ is the point of attachment to the indole, and the remainder are H or are as described for substituents on $R^{42}$, and $A^1$ and $Z^3$ are as described in Formula (I).

In one embodiment of Formula (IV), $A^1$ is furyl, imidazolyl, isothiazolyl, isoxazolyl, pyrazolyl, pyrrolyl, thiazolyl, thiadiazolyl, thienyl, triazolyl, heterocycloalkyl, or heterocycloalkenyl; each of which is unfused or fused with benzene, heteroarene or $A^{1A}$; and $A^{1A}$ is heterocycloalkene. In another embodiment of Formula (IV), $A^1$ is furyl. In another embodiment of Formula (IV), $A^1$ is imidazolyl. In another embodiment of Formula (IV), $A^1$ is isothiazolyl. In another embodiment of Formula (IV), $A^1$ is isoxazolyl. In another embodiment of Formula (IV), $A^1$ is pyrazolyl. In another embodiment of Formula (IV), $A^1$ is pyrrolyl. In another embodiment of Formula (IV), $A^1$ is thiazolyl. In another embodiment of Formula (IV), $A^1$ is thiadiazolyl. In another embodiment of Formula (IV), $A^1$ is thienyl. In another embodiment of Formula (IV), $A^1$ is
In another embodiment of Formula (IV), $A^1$ is triazolyl. In another embodiment of Formula (IV), $A^1$ is heterocycloalkyl. In another embodiment of Formula (IV), $A^1$ is heterocycloalkenyl. In another embodiment of Formula (IV), $A^1$ is piperidinyl. In another embodiment of Formula (IV), $A^1$ is morpholinyl. In another embodiment of Formula (IV), $A^1$ is dihydro-1,3,4-thiadiazol-2-yl. In another embodiment of Formula (IV), $A^1$ is benzothien-2-yl. In another embodiment of Formula (IV), $A^1$ is benzothiazol-2-yl. In another embodiment of Formula (IV), $A^1$ is benzothiazol-2-yl. In another embodiment of Formula (IV), $A^1$ is [1,2,4]triazolo[1,5-a]pyrimidin-2-yl. In another embodiment of Formula (IV), $A^1$ is tetrahydrothien-3-yl. In another embodiment of Formula (IV), $A^1$ is [1,2,4]triazolo[1,5-a]pyrimidin-2-yl. In another embodiment of Formula (IV), $A^1$ is imidazo[2,1-b][1,3]thiazol-5-yl.

In one embodiment of Formula (IV), $A^1$ is unsubstituted. In another embodiment of Formula (IV), $A^1$ is substituted with one or two or three or four or five independently selected $R^1$, $OR^1$, $C(O)OR^1$, $NHR^1$, $N(R^1)_2$, $C(N)C(O)R^1$, $C(O)NHR^1$, $NHC(O)R^1$, $NR^1C(O)R^1$, (O), $NO_2$, F, Cl, Br, I, or $CF_3$. In one embodiment of Formula (IV), $A^1$ is unsubstituted. In another embodiment of Formula (IV), $A^1$ is substituted with $NHR^1$. In another embodiment of Formula (IV), $A^1$ is substituted with $NHR^1$, and $NO_2$. In another embodiment of Formula (IV), $A^1$ is substituted with $NHR^1$. In another embodiment of Formula (IV), $A^1$ is substituted with $NR^1C(O)R^1$. In another embodiment of Formula (IV), $A^1$ is substituted with $N(R^1)_2$. In another embodiment of Formula (IV), $A^1$ is substituted with $C(N)C(O)R^1$, and $R^1$. In another embodiment of Formula (IV), $A^1$ is substituted with $NHC(O)R^1$, and $R^1$. In another embodiment of Formula (IV), $A^1$ is substituted with $R^1$. In another embodiment of Formula (IV), $A^1$ is substituted with two independently selected $R^1$. In another embodiment of Formula (IV), $A^1$ is substituted with Cl. In another embodiment of Formula (IV), $A^1$ is substituted with $CF_3$. In another embodiment of Formula (IV), $A^1$ is substituted with F. In another embodiment of Formula (IV), $A^1$ is substituted with three independently selected $R^1$, and $C(O)OR^1$. In another embodiment of Formula (IV), $A^1$ is substituted $R^1$, and $C(O)OR^1$. In another embodiment of Formula (IV), $A^1$ is substituted $R^1$, and Cl. In another embodiment of Formula (IV), $A^1$ is substituted $R^1$, and Br. In another embodiment of Formula (IV), $A^1$ is substituted with three independently selected $R^1$. In another embodiment of Formula (IV), $A^1$ is substituted with $C(O)NHR^1$. In another embodiment of Formula (IV), $A^1$ is substituted with two independently selected $R^1$, and Cl. In another embodiment of Formula (IV), $A^1$ is substituted with $R^1$, and $NO_2$. In another embodiment of Formula (IV), $A^1$ is substituted $NHR^1$, and $NO_2$. In another embodiment of Formula (IV), $A^1$ is substituted with (O). In another embodiment of Formula (IV), $A^1$ is substituted with $OR^1$.

In one embodiment of Formula (IV), $R^1$ is phenyl. In another embodiment of Formula (IV), $R^1$ is pyrazolyl. In another embodiment of Formula (IV), $R^1$ is morpholinyl. In another embodiment of Formula (IV), $R^1$ is isoxazolyl. In another embodiment of Formula (IV), $R^1$ is piperidinyl. In another embodiment of Formula (IV), $R^1$ is alkyl, which is unsubstituted. In another embodiment of Formula (IV), $R^1$ is alkyl, which is substituted with one or more $R^7$, $SR^7$, $N(R^7)_2$, $NHC(O)R^7$, or Cl.

In one embodiment of Formula (IV), $R^7$ is phenyl. In another embodiment of Formula (IV), $R^7$ is methyl. In another embodiment of Formula (IV), $R^7$ is isopropyl. In another embodiment of Formula (IV), $R^7$ is pyrrolinyl. In another embodiment of Formula (IV), $R^7$ is morpholinyl. In another embodiment of Formula (IV), $R^7$ is tetrahydropyranyl.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (V)

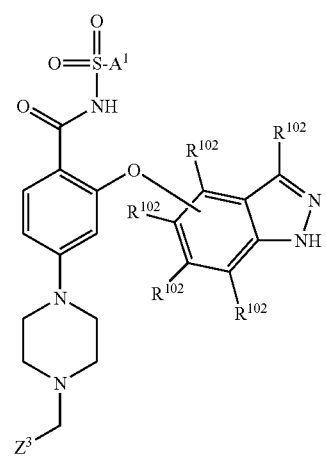

(V)

wherein one R¹⁰² is the point of attachment to the indazole, and the remainder are H or are as described for substituents on R⁴², and A¹ and Z³ are as described in Formula (I).

In one embodiment of Formula (V), A¹ is furyl, imidazolyl, isothiazolyl, isoxazolyl, pyrazolyl, pyrrolyl, thiazolyl, thiadiazolyl, thienyl, triazolyl, heterocycloalkyl, or heterocycloalkenyl; each of which is unfused or fused with benzene, heteroarene or A¹·⁴; and A¹·⁴ is heterocycloalkene. In another embodiment of Formula (V), A¹ is furyl. In another embodiment of Formula (V), A¹ is imidazolyl. In another embodiment of Formula (V), A¹ is isothiazolyl. In another embodiment of Formula (V), A¹ is isoxazolyl. In another embodiment of Formula (V), A¹ is pyrazolyl. In another embodiment of Formula (V), A¹ is pyrrolyl. In another embodiment of Formula (V), A¹ is thiazolyl. In another embodiment of Formula (V), A¹ is thiadiazolyl. In another embodiment of Formula (V), A¹ is thienyl. In another embodiment of Formula (V), A¹ is
In another embodiment of Formula (V), A¹ is triazolyl. In another embodiment of Formula (V), A¹ is heterocycloalkyl. In another embodiment of Formula (V), A¹ is heterocycloalkenyl. In another embodiment of Formula (V), A¹ is piperidinyl. In another embodiment of Formula (V), A¹ is morpholinyl. In another embodiment of Formula (V), A¹ is dihydro-1,3,4-thiadiazol-2-yl. In another embodiment of Formula (V), A¹ is benzothien-2-yl. In another embodiment of Formula (V), A¹ is benzothiazol-2-yl. In another embodiment of Formula (V), A¹ is benzothiazol-2-yl. In another embodiment of Formula (V), A¹ is [1,2,4]triazolo[1,5-a]pyrimidin-2-yl. In another embodiment of Formula (V), A¹ is tetrahydrothien-3-yl. In another embodiment of Formula (V), A¹ is [1,2,4]triazolo[1,5-a]pyrimidin-2-yl. In another embodiment of Formula (V), A¹ is imidazo[2,1-b][1,3]thiazol-5-yl.

In one embodiment of Formula (V), A¹ is unsubstituted. In another embodiment of Formula (V), A¹ is substituted with one or two or three or four or five independently selected R¹, OR¹, C(O)OR¹, NHR¹, N(R¹)₂, C(N)C(O)R¹, C(O)NHR¹, NHC(O)R¹, NR¹C(O)R¹, (O), NO₂, F, Cl, Br, I, or CF₃. In one embodiment of Formula (V), A¹ is unsubstituted. In another embodiment of Formula (V), A¹ is substituted with NHR¹. In another embodiment of Formula (V), A¹ is substituted with NHR¹, and NO₂. In another embodiment of Formula (V), A¹ is substituted with NHR¹. In another embodiment of Formula (V), A¹ is substituted with NR¹C(O)R¹. In another embodiment of Formula (V), A¹ is substituted with N(R¹)₂. In another embodiment of Formula (V), A¹ is substituted with C(N)C(O)R¹, and R¹. In another embodiment of Formula (V), A¹ is substituted with NHC(O)R¹, and R¹. In another embodiment of Formula (V), A¹ is substituted with R¹. In another embodiment of Formula (V), A¹ is substituted with two independently selected R¹. In another embodiment of Formula (V), A¹ is substituted with Cl. In another embodiment of Formula (V), A¹ is substituted with CF₃. In another embodiment of Formula (V), A¹ is substituted with F. In another embodiment of Formula (V), A¹ is substituted with three independently selected R¹, and C(O)OR¹. In another embodiment of Formula (V), A¹ is substituted R¹, and C(O)OR¹. In another embodiment of Formula (V), A¹ is substituted R¹, and Cl. In another embodiment of Formula (V), A¹ is substituted R¹, and Br. In another embodiment of Formula (V), A¹ is substituted with three independently selected R¹. In another embodiment of Formula (V), A¹ is substituted with C(O)NHR¹. In another embodiment of Formula (V), A¹ is substituted with two independently selected R¹, and Cl. In another embodiment of Formula (V), A¹ is substituted with R¹, and NO₂. In another embodiment of Formula (V), A¹ is substituted NHR¹, and NO₂. In another embodiment of Formula (V), A¹ is substituted with (O). In another embodiment of Formula (V), A¹ is substituted with OR¹.

In one embodiment of Formula (V), R¹ is phenyl. In another embodiment of Formula (V), R¹ is pyrazolyl. In another embodiment of Formula (V), R¹ is morpholinyl. In another embodiment of Formula (V), R¹ is isoxazolyl. In another embodiment of Formula (V), R¹ is piperidinyl. In another embodiment of Formula (V), R¹ is alkyl, which is unsubstituted. In another embodiment of Formula (V), R¹ is alkyl, which is substituted with one or more R⁷, SR⁷, N(R⁷)₂, NHC(O)R⁷, or Cl.

In one embodiment of Formula (V), R⁷ is phenyl. In another embodiment of Formula (V), R⁷ is methyl. In another embodiment of Formula (V), R⁷ is isopropyl. In another embodiment of Formula (V), R⁷ is pyrrolinyl. In another embodiment of Formula (V), R⁷ is morpholinyl. In another embodiment of Formula (V), R⁷ is tetrahydropyranyl.

Still another embodiment pertains to compounds having Formula V, which are
tert-butyl (2S)-2-{[(5-{[4-(4-{[2-(4-chlorophenyl)-4,4-dimethylcyclohex-1-en-1-yl]methyl}piperazin-1-yl)-2-(1H-indazol-4-yloxy)benzoyl]sulfamoyl}-4-methyl-1,3-thiazol-2-yl)oxy]methyl}morpholine-4-carboxylate;
4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-indazol-4-yloxy)benzamide;
and therapeutically acceptable salts, prodrugs, salts of prodrugs and metabolites thereof.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (VI)

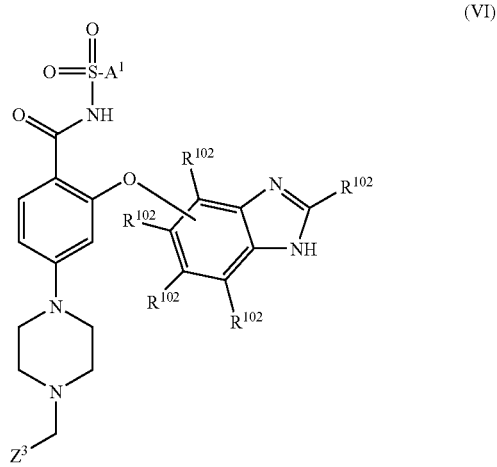

(VI)

wherein one R¹⁰² is the point of attachment to the benzimidazole, and the remainder are H or are as described for substituents on R⁴², and A¹ and Z³ are as described in Formula (I).

In one embodiment of Formula (VI), A¹ is furyl, imidazolyl, isothiazolyl, isoxazolyl, pyrazolyl, pyrrolyl, thiazolyl, thiadiazolyl, thienyl, triazolyl, heterocycloalkyl, or heterocycloalkenyl; each of which is unfused or fused with benzene, heteroarene or A¹·⁴; and A¹·⁴ is heterocycloalkene. In another embodiment of Formula (VI), A¹ is furyl. In another embodiment of Formula (VI), A¹ is imidazolyl. In another embodiment of Formula (VI), A¹ is isothiazolyl. In another embodiment of Formula (VI), A¹ is isoxazolyl. In another embodiment of Formula (VI), A¹ is pyrazolyl. In another embodiment of Formula (VI), A¹ is pyrrolyl. In another embodiment of Formula (VI), A¹ is thiazolyl. In another embodiment of Formula (VI), A¹ is thiadiazolyl. In another embodiment of Formula (VI), A¹ is thienyl. In another embodiment of Formula (VI), A¹ is triazolyl. In another embodiment of Formula (VI), A¹ is heterocycloalkyl. In another embodiment of Formula (VI), A¹ is heterocycloalkenyl. In another embodiment of Formula (VI), A¹ is piperidinyl. In another embodiment of Formula (VI), A¹ is morpholinyl. In another embodiment of Formula (VI), A¹ is dihydro-1,3,4-thiadiazol-2-yl. In another embodiment of Formula (VI), A¹ is benzothien-2-yl. In another embodiment of Formula (VI), A¹ is benzothiazol-2-yl. In another embodiment of Formula (VI), A¹ is benzothiazol-2-yl. In another embodiment of Formula (VI), A¹ is [1,2,4]triazolo[1,5-a]pyrimidin-2-yl. In another embodiment of Formula (VI), A¹ is tetrahydrothien-3-yl. In another embodiment of Formula (VI), A¹ is [1,2,4]triazolo[1,5-a]pyrimidin-2-yl. In another embodiment of Formula (VI), A¹ is imidazo[2,1-b][1,3]thiazol-5-yl.

In one embodiment of Formula (VI), A¹ is unsubstituted. In another embodiment of Formula (VI), A¹ is substituted with one or two or three or four or five independently selected R¹, OR¹, C(O)OR¹, NHR¹, N(R¹)₂, C(N)C(O)R¹, C(O)NHR¹, NHC(O)R¹, NR¹C(O)R¹, (O), NO₂, F, Cl, Br, I, or CF₃. In one embodiment of Formula (VI), A¹ is unsubstituted. In another embodiment of Formula (VI), A¹ is substituted with NHR¹. In another embodiment of Formula (VI), A¹ is substituted with NHR¹, and NO₂. In another embodiment of Formula (VI), A¹ is substituted with NHR¹. In another embodiment of Formula (VI), A¹ is substituted with NR¹C(O)R¹. In another embodiment of Formula (VI), A¹ is substituted with N(R¹)₂. In another embodiment of Formula (VI), A¹ is substituted with C(N)C(O)R¹, and R¹. In another embodiment of Formula (VI), A¹ is substituted with NHC(O)R¹, and R¹. In another embodiment of Formula (VI), A¹ is substituted with R¹. In another embodiment of Formula (VI), A¹ is substituted with two independently selected R¹. In another embodiment of Formula (VI), A¹ is substituted with Cl. In another embodiment of Formula (VI), A¹ is substituted with CF₃. In another embodiment of Formula (VI), A¹ is substituted with F. In another embodiment of Formula (VI), A¹ is substituted with three independently selected R¹, and C(O)OR¹. In another embodiment of Formula (VI), A¹ is substituted R¹, and C(O)OR¹. In another embodiment of Formula (VI), A¹ is substituted R¹, and Cl. In another embodiment of Formula (VI), A¹ is substituted R¹, and Br. In another embodiment of Formula (VI), A¹ is substituted with three independently selected R¹. In another embodiment of Formula (VI), A¹ is substituted with C(O)NHR¹. In another embodiment of Formula (VI), A¹ is substituted with two independently selected R¹, and Cl. In another embodiment of Formula (VI), A¹ is substituted with R¹, and NO₂. In another embodiment of Formula (VI), A¹ is substituted NHR¹, and NO₂. In another embodiment of Formula (VI), A¹ is substituted with (O). In another embodiment of Formula (VI), A¹ is substituted with OR¹.

In one embodiment of Formula (VI), R¹ is phenyl. In another embodiment of Formula (VI), R¹ is pyrazolyl. In another embodiment of Formula (VI), R¹ is morpholinyl. In another embodiment of Formula (VI), R¹ is isoxazolyl. In another embodiment of Formula (VI), R¹ is piperidinyl. In another embodiment of Formula (VI), R¹ is alkyl, which is unsubstituted. In another embodiment of Formula (VI), R¹ is alkyl, which is substituted with one or more R⁷, SR⁷, N(R⁷)₂, NHC(O)R⁷, or Cl.

In one embodiment of Formula (VI), R⁷ is phenyl. In another embodiment of Formula (VI), R⁷ is methyl. In another embodiment of Formula (VI), R⁷ is isopropyl. In another embodiment of Formula (VI), R⁷ is pyrrolinyl. In another embodiment of Formula (VI), R⁷ is morpholinyl. In another embodiment of Formula (VI), R⁷ is tetrahydropyranyl.

Still another embodiment pertains to compounds having Formula VI, which are
tert-butyl (2S)-2-{[(5-{[2-(1H-benzimidazol-4-yloxy)-4-(4-{[2-(4-chlorophenyl)-4,4-dimethylcyclohex-1-en-1-yl]methyl}piperazin-1-yl)benzoyl]sulfamoyl}-4-methyl-1,3-thiazol-2-yl)oxy]methyl}morpholine-4-carboxylate;
2-(1H-benzimidazol-4-yloxy)-4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)benzamide;
and therapeutically acceptable salts, prodrugs, salts of prodrugs and metabolites thereof.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (VII)

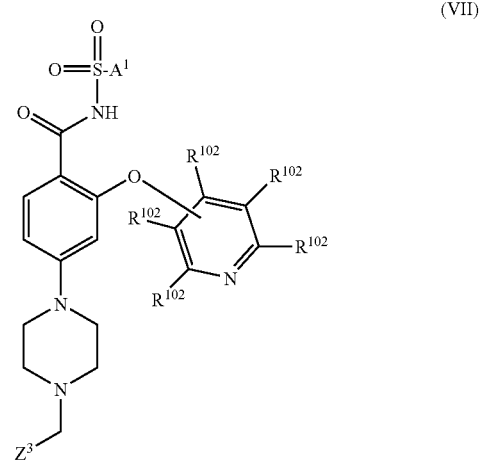

(VII)

wherein one R¹⁰² is the point of attachment to the pyridine, and the remainder are H or are as described for substituents on R⁴², and A¹ and Z³ are as described in Formula (I).

In one embodiment of Formula (VII), A¹ is furyl, imidazolyl, isothiazolyl, isoxazolyl, pyrazolyl, pyrrolyl, thiazolyl, thiadiazolyl, thienyl, triazolyl, heterocycloalkyl, or heterocycloalkenyl; each of which is unfused or fused with benzene, heteroarene or A¹·⁴; and A¹·⁴ is heterocycloalkene. In another embodiment of Formula (VII), A¹ is furyl. In another embodiment of Formula (VII), A¹ is imidazolyl. In another embodiment of Formula (VII), A¹ is isothiazolyl. In another embodiment of Formula (VII), A¹ is isoxazolyl. In another embodiment of Formula (VII), A¹ is pyrazolyl. In another embodiment of Formula (VII), A¹ is pyrrolyl. In another embodiment of Formula (VII), A¹ is thiazolyl. In another embodiment of Formula (VII), A¹ is thiadiazolyl. In another embodiment of Formula (VII), A¹ is thienyl. In another embodiment of Formula (VII), A¹ is triazolyl. In another embodiment of Formula (VII), A¹ is heterocycloalkyl. In another embodiment of Formula (VII), A¹ is heterocycloalkenyl. In another embodiment of Formula (VII), A¹ is piperidinyl. In another embodiment of Formula (VII), A¹ is morpholinyl. In another embodiment of Formula (VII), A¹ is dihydro-1,3,4-thiadiazol-2-yl. In another embodiment of Formula (VII), A¹ is benzothien-2-yl. In another embodiment of Formula (VII), A¹ is benzothiazol-2-yl. In another embodiment of Formula (VII), A¹ is benzothiazol-2-yl. In another embodiment of Formula (VII), A¹ is [1,2,4]triazolo[1,5-a]pyrimidin-2-yl. In another embodiment of Formula (VII), A¹ is tetrahydrothien-3-yl. In another embodiment of Formula (VII), A¹ is [1,2,4]triazolo[1,5-a]pyrimidin-2-yl. In another embodiment of Formula (VII), A¹ is imidazo[2,1-b][1,3]thiazol-5-yl.

In one embodiment of Formula (VII), A¹ is unsubstituted. In another embodiment of Formula (VII), A¹ is substituted with one or two or three or four or five independently selected R¹, OR¹, C(O)OR¹, NHR¹, N(R¹)₂, C(N)C(O)R¹, C(O)NHR¹, NHC(O)R¹, NR¹C(O)R¹, (O), NO₂, F, Cl, Br, I, or CF₃. In one embodiment of Formula (VII), A¹ is unsubstituted. In another embodiment of Formula (VII), A¹ is substituted with NHR¹. In another embodiment of Formula (VII), A¹ is substituted with NHR¹, and NO₂. In another embodiment of Formula (VII), A¹ is substituted with NHR¹. In another embodiment of Formula (VII), A¹ is substituted with NR¹C(O)R¹. In another embodiment of Formula (VII), A¹ is substituted with N(R¹)₂. In another embodiment of Formula (VII), A¹ is substituted with C(N)C(O)R¹, and R¹. In another embodiment of Formula (VII), A¹ is substituted with NHC(O)R¹, and R¹. In another embodiment of Formula (VII), A¹ is substituted with R¹. In another embodiment of Formula (VII), A¹ is substituted with two independently selected R¹. In another embodiment of Formula (VII), A¹ is substituted with Cl. In another embodiment of Formula (VII), A¹ is substituted with CF₃. In another embodiment of Formula (VII), A¹ is substituted with F. In another embodiment of Formula (VII), A¹ is substituted with three independently selected R¹, and C(O)OR¹. In another embodiment of Formula (VII), A¹ is substituted R¹, and C(O)OR¹. In another embodiment of Formula (VII), A¹ is substituted R¹, and Cl. In another embodiment of Formula (VII), A¹ is substituted R¹, and Br. In another embodiment of Formula (VII), A¹ is substituted with three independently selected R¹. In another embodiment of Formula (VII), A¹ is substituted with C(O)NHR¹. In another embodiment of Formula (VII), A¹ is substituted with two independently selected R¹, and Cl. In another embodiment of Formula (VII), A¹ is substituted with R¹, and NO₂. In another embodiment of Formula (VII), A¹ is substituted NHR¹, and NO₂. In another embodiment of Formula (VII), A¹ is substituted with (O). In another embodiment of Formula (VII), A¹ is substituted with OR¹.

In one embodiment of Formula (VII), R¹ is phenyl. In another embodiment of Formula (VII), R¹ is pyrazolyl. In another embodiment of Formula (VII), R¹ is morpholinyl. In another embodiment of Formula (VII), R¹ is isoxazolyl. In another embodiment of Formula (VII), R¹ is piperidinyl. In another embodiment of Formula (VII), R¹ is alkyl, which is unsubstituted. In another embodiment of Formula (VII), R¹ is alkyl, which is substituted with one or more R⁷, SR⁷, N(R⁷)₂, NHC(O)R⁷, or Cl.

In one embodiment of Formula (VII), R⁷ is phenyl. In another embodiment of Formula (VII), R⁷ is methyl. In another embodiment of Formula (VII), R⁷ is isopropyl. In another embodiment of Formula (VII), R⁷ is pyrrolinyl. In another embodiment of Formula (VII), R⁷ is morpholinyl. In another embodiment of Formula (VII), R⁷ is tetrahydropyranyl.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (VIII)

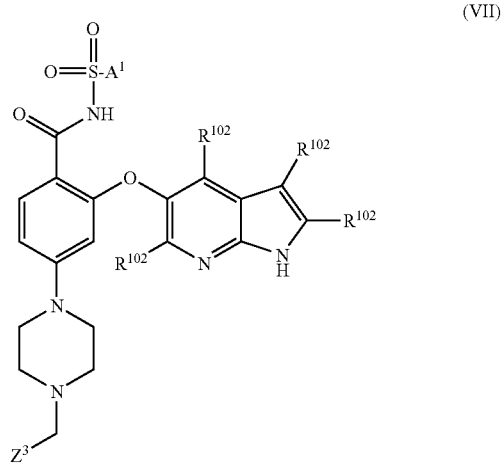

wherein each R¹⁰² are independently H or are as described for substituents on R⁴², and A¹ and Z³ are as described in Formula (I).

In one embodiment of Formula (VIII), A¹ is furyl, imidazolyl, isothiazolyl, isoxazolyl, pyrazolyl, pyrrolyl, thiazolyl, thiadiazolyl, thienyl, triazolyl, heterocycloalkyl, or heterocycloalkenyl; each of which is unfused or fused with benzene, heteroarene or A¹ᴬ; and A¹ᴬ is heterocycloalkene. In another embodiment of Formula (VIII), A¹ is furyl. In another embodiment of Formula (VIII), A¹ is imidazolyl. In another embodiment of Formula (VIII), A¹ is isothiazolyl. In another embodiment of Formula (VIII), A¹ is isoxazolyl. In another embodiment of Formula (VIII), A¹ is pyrazolyl. In another embodiment of Formula (VIII), A¹ is pyrrolyl. In another embodiment of Formula (VIII), A¹ is thiazolyl. In another embodiment of Formula (VIII), A¹ is thiadiazolyl. In another embodiment of Formula (VIII), A¹ is thienyl. In another embodiment of Formula (VIII), A¹ is triazolyl. In another embodiment of Formula (VIII), A¹ is heterocycloalkyl. In another embodiment of Formula (VIII), A¹ is heterocycloalkenyl. In another embodiment of Formula (VIII), A¹ is piperidinyl. In another embodiment of Formula (VIII), A¹ is morpholinyl. In another embodiment of Formula (VIII), A¹ is dihydro-1,3,4-thiadiazol-2-yl. In another embodiment of Formula (VIII), A¹ is benzothien-2-yl. In another embodiment of Formula (VIII), A¹ is benzothiazol-2-yl. In another embodiment of Formula (VIII), A¹ is benzothiazol-2-yl. In another embodiment of Formula (VIII), A¹ is [1,2,4]triazolo[1,5-a]pyrimidin-2-yl. In another embodiment of Formula (VIII), A¹ is tetrahydrothien-3-yl. In another embodiment of Formula (VIII), A¹ is [1,2,4]triazolo[1,5-a]pyrimidin-2-yl. In another embodiment of Formula (VIII), A¹ is imidazo[2,1-b][1,3]thiazol-5-yl.

In one embodiment of Formula (VIII), A¹ is unsubstituted. In another embodiment of Formula (VIII), A¹ is substituted with one or two or three or four or five independently selected R¹, OR¹, C(O)OR¹, NHR¹, N(R¹)₂, C(N)C(O)R¹, C(O)NHR¹, NHC(O)R¹, NR¹C(O)R¹, (O), NO₂, F, Cl, Br, I, or CF₃. In one embodiment of Formula (VIII), A¹ is unsubstituted. In another embodiment of Formula (VIII), A¹ is substituted with NHR¹. In another embodiment of Formula (VIII), A¹ is substituted with NHR¹, and NO₂. In another embodiment of Formula (VIII), A¹ is substituted with NHR¹. In another embodiment of Formula (VIII), A¹ is substituted with NR¹C(O)R¹. In another embodiment of Formula (VIII), A¹ is substituted with N(R¹)₂. In another embodiment of Formula (VIII), A¹ is substituted with C(N)C(O)R¹, and R¹.

In another embodiment of Formula (VIII), $A^1$ is substituted with $NHC(O)R^1$, and $R^1$. In another embodiment of Formula (VIII), $A^1$ is substituted with $R^1$. In another embodiment of Formula (VIII), $A^1$ is substituted with two independently selected $R^1$. In another embodiment of Formula (VIII), $A^1$ is substituted with Cl. In another embodiment of Formula (VIII), $A^1$ is substituted with $CF_3$. In another embodiment of Formula (VIII), $A^1$ is substituted with F. In another embodiment of Formula (VIII), $A^1$ is substituted with three independently selected $R^1$, and $C(O)OR^1$. In another embodiment of Formula (VIII), $A^1$ is substituted $R^1$, and $C(O)OR^1$. In another embodiment of Formula (VIII), $A^1$ is substituted $R^1$, and Cl. In another embodiment of Formula (VIII), $A^1$ is substituted $R^1$, and Br. In another embodiment of Formula (VIII), $A^1$ is substituted with three independently selected $R^1$. In another embodiment of Formula (VIII), $A^1$ is substituted with $C(O)NHR^1$. In another embodiment of Formula (VIII), $A^1$ is substituted with two independently selected $R^1$, and Cl. In another embodiment of Formula (VIII), $A^1$ is substituted with $R^1$, and $NO_2$. In another embodiment of Formula (VIII), $A^1$ is substituted $NHR^1$, and $NO_2$. In another embodiment of Formula (VIII), $A^1$ is substituted with (O). In another embodiment of Formula (VIII), $A^1$ is substituted with $OR^1$.

In one embodiment of Formula (VIII), $R^1$ is phenyl. In another embodiment of Formula (VIII), $R^1$ is pyrazolyl. In another embodiment of Formula (VIII), $R^1$ is morpholinyl. In another embodiment of Formula (VIII), $R^1$ is isoxazolyl. In another embodiment of Formula (VIII), $R^1$ is piperidinyl. In another embodiment of Formula (VIII), $R^1$ is alkyl, which is unsubstituted. In another embodiment of Formula (VIII), $R^1$ is alkyl, which is substituted with one or more $R^7$, $SR^7$, $N(R^7)_2$, $NHC(O)R^7$, or Cl.

In one embodiment of Formula (VIII), $R^7$ is phenyl. In another embodiment of Formula (VIII), $R^7$ is methyl. In another embodiment of Formula (VIII), $R^7$ is isopropyl. In another embodiment of Formula (VIII), $R^7$ is pyrrolinyl. In another embodiment of Formula (VIII), $R^7$ is morpholinyl. In another embodiment of Formula (VIII), $R^7$ is tetrahydropyranyl.

Still another embodiment pertains to compounds having Formula VIII, which are
tert-butyl (2S)-2-{[(5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-4-methyl-1,3-thiazol-2-yl)oxy]methyl}morpholine-4-carboxylate;
4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-pyrrolo[2,3-b]pyridin-5-yloxy)benzamide;
and therapeutically acceptable salts, prodrugs, salts of prodrugs and metabolites thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment comprises methods of treating autoimmune disease in a mammal comprising administering thereto a therapeutically acceptable amount of a compound having Formula (I).

Still another embodiment pertains to compositions for treating diseases during which anti-apoptotic Bcl-2 proteins are expressed, said compositions comprising an excipient and a therapeutically effective amount of the compound having Formula (I).

Still another embodiment pertains to methods of treating disease in a patient during which anti-apoptotic Bcl-2 proteins are expressed, said methods comprising administering to the patient a therapeutically effective amount of a compound having Formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having Formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound having Formula (I).

Still another embodiment pertains to compositions for treating diseases during which are expressed anti-apoptotic Bcl-2 proteins, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which are expressed anti-apoptotic Bcl-2 proteins, said methods comprising administering to the patient a therapeutically effective amount of a compound having Formula (I) and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said compositions comprising an excipient and a therapeutically effective amount of the compound having Formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with anti-apoptotic Bcl-2 proteins.

Certain precursor compounds which may be metabolized in vitro or in vivo to form compounds having Formula (I) may also have utility for treating diseases associated with expression of anti-apoptotic Bcl-2 proteins.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds and prodrugs thereof are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT 103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, J. of Immunology 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide) or ABT-737 (i.e., N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, Cancer Research 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine)(ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

Determination of the utility of compounds having Formula (I) as binders to and inhibitors of anti-apoptotic Bcl-2 proteins was performed using the Time Resolved-Fluorescence Resonance Energy Transfer (TR-FRET) Assay. Tb-anti-GST antibody was purchased from Invitrogen (Catalog No. PV4216).

Probe Synthesis

All reagents were used as obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1,1,3,3-tetramethyluronium hexafluorophosphate (HBTU), N-hydroxybenzotriazole (HOBt) and piperidine were obtained from Applied Biosystems, Inc. (ABI), Foster City, Calif. or American Bioanalytical, Natick, Mass. Preloaded 9-Fluorenylmethyloxycarbonyl (Fmoc) amino acid cartridges (Fmoc-Ala-OH, Fmoc-Cys(Trt)-OH, Fmoc-Asp (tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmoc-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, Calif. The peptide synthesis resin (Fmoc-Rink amide MBHA resin) and Fmoc-Lys(Mtt)-OH were obtained from Novabiochem, San Diego, Calif. Single-isomer 6-carboxyfluorescein succinimidyl ester (6-FAM-NHS) was obtained from Anaspec. Trifluoroacetic acid (TFA) was obtained from Oakwood Products, West Columbia, S.C. Thioanisole, phenol, triisopropylsilane (TIS), 3,6-dioxa-1,8-octanedithiol (DODT) and isopropanol were obtained from Aldrich Chemical Co., Milwaukee, Wis. Matrix-assisted laser desorption ionization mass-spectra (MALDI-MS) were recorded on an Applied Biosystems Voyager DE-PRO MS). Electrospray mass-spectra (ESI-MS) were recorded on Finnigan SSQ7000 (Finnigan Corp., San Jose, Calif.) in both positive and negative ion mode.

General Procedure for Solid-Phase Peptide Synthesis (SPPS)

Peptides were synthesized with, at most, 250 μmol preloaded Wang resin/vessel on an ABI 433A peptide synthesizer using 250 μmol scale Fastmoc™ coupling cycles. Preloaded cartridges containing 1 mmol standard Fmoc-amino acids, except for the position of attachment of the fluorophore, where 1 mmol Fmoc-Lys(Mtt)-OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) from Lysine

The resin from the synthesizer was washed thrice with dichloromethane and kept wet. 150 mL of 95:4:1 dichloromethane:triisopropylsilane:trifluoroacetic acid was flowed through the resin bed over 30 minutes. The mixture turned deep yellow then faded to pale yellow. 100 mL of N,N-dimethylformamide was flowed through the bed over 15 minutes. The resin was then washed thrice with N,N-dimethylformamide and filtered. Ninhydrin tests showed a strong signal for primary amine

Resin Labeling with 6-Carboxyfluorescein-NHS (6-FAM-NHS)

The resin was treated with 2 equivalents 6-FAM-NHS in 1% DIEA/N,N-dimethylformamide and stirred or shaken at ambient temperature overnight. When complete, the resin was drained, washed thrice with N,N-dimethylformamide, thrice with (1×DCM and 1× methanol) and dried to provide an orange resin that was negative by ninhydrin test.

General Procedure for Cleavage and Deprotection of Resin-Bound Peptide

Peptides were cleaved from the resin by shaking for 3 hours at ambient temperature in a cleavage cocktail consisting of 80% TFA, 5% water, 5% thioanisole, 5% phenol, 2.5% TIS, and 2.5% EDT (1 mL/0.1 g resin). The resin was removed by filtration and rinsing twice with TFA. The TFA was evaporated from the filtrates, and product was precipitated with ether (10 mL/0.1 g resin), recovered by centrifugation, washed twice with ether (10 mL/0.1 g resin) and dried to give the crude peptide.

General Procedure for Purification of Peptides

The crude peptides were purified on a Gilson preparative HPLC system running Unipoint® analysis software (Gilson, Inc., Middleton, Wis.) on a radial compression column containing two 25×100 mm segments packed with Delta-Pak™ C18 15 μm particles with 100 Å pore size and eluted with one of the gradient methods listed below. One to two milliliters of crude peptide solution (10 mg/mL in 90% DMSO/water) was purified per injection. The peaks containing the product(s) from each run were pooled and lyophilized. All preparative runs were run at 20 mL/min with eluents as buffer A: 0.1% TFA-water and buffer B: acetonitrile.

General Procedure for Analytical HPLC

Analytical HPLC was performed on a Hewlett-Packard 1200 series system with a diode-array detector and a Hewlett-Packard 1046A fluorescence detector running HPLC 3D CHEMSTATION software version A.03.04 (Hewlett-Packard. Palo Alto, Calif.) on a 4.6×250 mm YMC column packed with ODS-AQ 5 μm particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/min.

F-Bak: Peptide Probe Acetyl-GQVGRQLAIIGDK(6-FAM)INR-NH$_2$ (SEQ ID NO:1)

Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude product as an orange solid (0.37 g). This product was purified by RP-HPLC. Fractions across the main peak were tested by analytical RP-HPLC, and the pure fractions were isolated and lyophilized, with the major peak providing the title compound (0.0802 g) as a yellow solid; MALDI-MS m/z=2137.1 [(M+H)$^+$].

Alternative Synthesis of Peptide Probe F-Bak

Acetyl-GQVGRQLAIIGDK(6-FAM)INR-NH$_2$ (SEQ ID NO:1)

The protected peptide was assembled on 0.25 mmol Fmoc-Rink amide MBHA resin (Novabiochem) on an Applied Biosystems 433A automated peptide synthesizer running FASTMOC™ coupling cycles using pre-loaded 1 mmol amino acid cartridges, except for the fluorescein(6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 DCM:TIS:TFA (v/v/v) flowed through the resin over 15 minutes, followed by quenching with a flow of dimethylformamide. Single-isomer 6 carboxyfluorescein-NHS was reacted with the lysine side-chain in 1% DIEA in N,N-dimethylformamide and confirmed complete by ninhydrin testing. The peptide was cleaved from the resin and side-chains deprotected by treating with 80:5:5:5:2.5:2.5 TFA/water/phenol/thioanisole/triisopropylsilane: 3,6-dioxa-1,8-octanedithiol (v/v/v/v/v/v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z=2137.1 ((M+H)+)).

Time Resolved-Fluorescence Resonance Energy Transfer (TR-FRET) Assay

Representative compounds were serially diluted in dimethyl sulfoxide (DMSO) starting at 50 μM (2× starting concentration; 10% DMSO) and 10 μL were transferred into a 384-well plate. Then 10 μL of a protein/probe/antibody mix was added to each well at final concentrations listed in TABLE 1. The samples are then mixed on a shaker for 1 minute and incubated for an additional 3 hours at room temperature. For each assay, the probe/antibody and protein/probe/antibody were included on each assay plate as negative and positive controls, respectively. Fluorescence was measured on the ENVISION plate reader (Perkin Elmer) using a 340/35 nm excitation filter and 520/525 (F-Bak peptide) and 495/510 nm (Tb-labeled anti-Histidine antibody) emission filters. Inhibition constants (Ki) are shown in TABLE 2 below and were determined using Wang's equation (Wang Z.-X. An Exact Mathematical Expression For Describing Competitive Binding Of Two Different Ligands To A Protein Molecule. *FEBS Lett.* 1995, 360:111-4).

one protein to another protein. So a large $K_i$ value indicates a low binding affinity and a small $K_i$ value indicates a high binding affinity.

TABLE 1

Protein, Probe And Antibody Used For TR-FRET Assays

| Protein | Probe | Protein (nM) | Probe (nM) | Antibody | Antibody (nM) |
|---|---|---|---|---|---|
| GST-Bcl-2 | F-Bak Peptide Probe Acetyl-GQVGRQLAIIGDK (6-FAM)INR-amide (SEQ ID NO: 1) | 1 | 100 | Tb-anti-GST | 1 |

6-FAM = 6-carboxyfluorescein.;
Tb = terbium;
GST = glutathione S-transferase

TABLE 2

TR-FRET Bcl-2 Binding Ki (µM)

| Example No. | TR-FRET Binding: Bcl-2 Ki (µM) |
|---|---|
| 1 | 0.051449 |
| 2 | 0.082918 |
| 3 | 0.051702 |
| 5 | 0.176183 |
| 6 | 0.703735 |
| 7 | 0.000084 |
| 8 | 0.000064 |
| 9 | 0.000307 |
| 10 | 0.743178 |
| 11 | 0.177064 |
| 12 | 0.392534 |
| 13 | 0.387693 |
| 14 | 0.408575 |
| 15 | 0.282112 |
| 16 | 0.037859 |
| 17 | 0.356257 |
| 18 | 0.128531 |
| 19 | 0.234118 |
| 20 | 0.048076 |
| 22 | 0.188226 |
| 23 | 0.447133 |
| 24 | 0.3421 |
| 25 | 0.372106 |
| 26 | 0.393356 |
| 27 | 0.433996 |
| 28 | 0.417285 |
| 29 | 0.339986 |
| 30 | 0.269175 |
| 31 | 0.138755 |
| 32 | 0.43792 |
| 33 | 0.000649 |
| 34 | 0.001791 |
| 35 | 0.002067 |
| 36 | 0.293805 |
| 39 | 0.020238 |
| 40 | 0.000407 |
| 41 | 0.000053 |
| 42 | 0.000039 |
| 43 | 0.046497 |
| 44 | 0.024776 |
| 45 | 0.0067348 |
| 46 | 0.0017502 |
| 47 | 0.020416 |
| 48 | 0.001637 |

The inhibition constant ($K_i$) is the dissociation constant of an enzyme-inhibitor complex or a protein/small molecule complex, wherein the small molecule is inhibiting binding of one protein to another protein. So a large $K_i$ value indicates a low binding affinity and a small $K_i$ value indicates a high binding affinity.

The data in TABLE 2 shows inhibition constants for the inhibition of a Bak BH3 peptide probe to Bcl-2 protein and indicate that compounds according to the invention have high binding affinities for anti-apoptotic Bcl-2 protein. The compounds are therefore expected to have utility in treatment of diseases during which anti-apoptotic Bcl-2 protein is expressed.

It is expected that, because compounds having Formula I bind to Bcl-2, they would also have utility as binders to anti-apoptotic proteins having close structural homology to Bcl-2, such as, for example, anti-apoptotic Bcl-$X_L$, Bcl-w, Mcl-1 and Bfl-1/A1 proteins.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, chronic lymphocytic leukemia, myeloma, prostate cancer spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in *Current Allergy and Asthma Reports* 2003, 3, 378-384; *British Journal of Haematology* 2000, 110 (3), 584-90; *Blood* 2000, 95(4), 1283-92; and *New England Journal of Medicine* 2004, 351(14), 1409-1418.

Involvement of Bcl-2 proteins in arthritis is disclosed in commonly-owned U.S. Provisional Patent Application Ser. No. 60/988,479.

Involvement of Bcl-2 proteins in bone marrow transplant rejection is disclosed in commonly-owned U.S. patent application Ser. No. 11/941,196.

Overexpression of Bcl-2 proteins correlates with resistance to chemotherapy, clinical outcome, disease progression, overall prognosis or a combination thereof in various cancers and disorders of the immune system. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds having Formula (I) would inhibit growth of cells expressing Bcl-2 proteins derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, *mycobacterium avium intracellulare, mycobacterium tuberculosis*, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherosclerotic disease, peripheral vascular disorders, peritonitis, pernicious anemia, phacogenic uveitis, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthopathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, *yersinia* and *salmonella*-associated arthropathy and the like.

SCHEMES AND EXPERIMENTALS

The following abbreviations have the meanings indicated. ADDP means 1,1'-(azodicarbonyl)dipiperidine; AD-mix-13 means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; $MP-BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

SCHEME 1

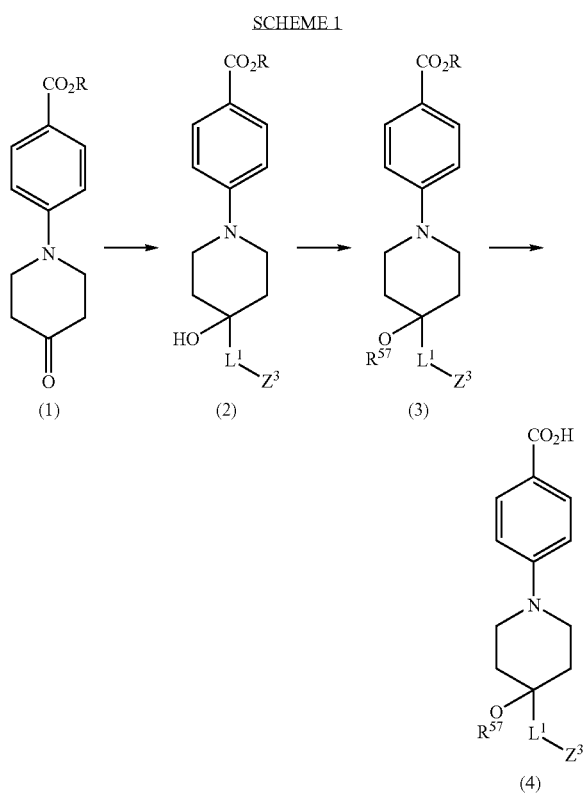

Compounds of Formula (4) can be prepared as shown in SCHEME 1, and can be used as described in SCHEME 8 to prepare compounds of Formula I, which are representative of the compounds of the present invention. Compounds of Formula (1) wherein R is alkyl, can be converted to compounds of Formula (2) using $Z^3L^1MgX^1$, wherein $X^1$ is a halide, in a solvent such as but not limited to ether or tetrahydrofuran. Compounds of Formula (3) can be prepared from compounds of Formula (2) using a strong base such as NaH and $R^{57}X^2$, wherein $X^2$ is a halide and $R^{57}$ is as described herein. Compounds of Formula (3), when treated with aqueous NaOH or LiOH, will provide compounds of Formula (4).

SCHEME 2

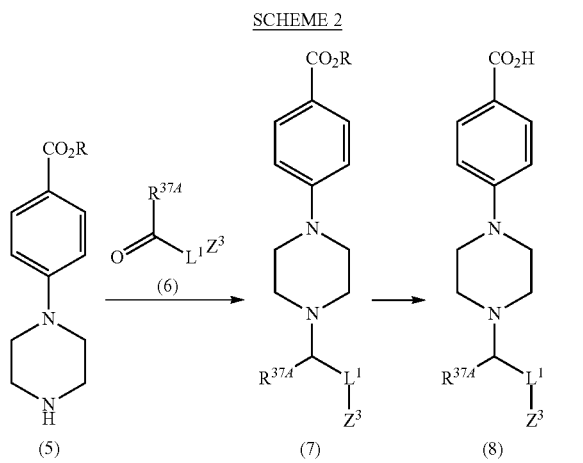

As shown in SCHEME 2, compounds of Formula (5) can be reacted with compounds of Formula (6) and a reducing agent to provide compounds of Formula (7). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, and dichloromethane or mixtures thereof. Compounds of Formula (8) can be prepared from compounds of Formula (7) as described in SCHEME 1, and can be used as described in SCHEME 8 to prepare compounds of Formula I.

SCHEME 3

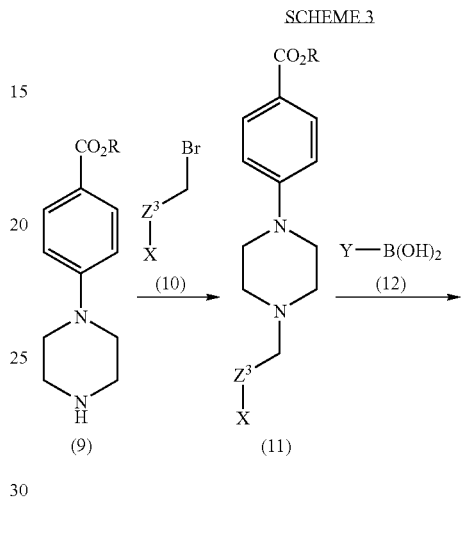

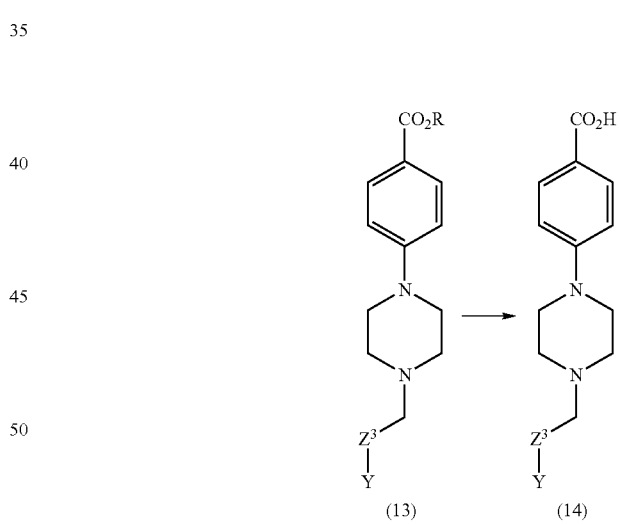

Compounds of Formula (9), when reacted with a compound a Formula (10) wherein X is a halide or triflate, and a base will provide a compound of Formula (11). Bases useful in the reaction include triethylamine, diisopropylethylamine and the like. Compounds of Formula (13), wherein Y is as described herein for substituents on $Z^3$, can be prepared from compounds of Formula (11) and compounds of Formula (12) using Suzuki coupling conditions known to those skilled in the art and readily available in the literature. Compounds of Formula (14) can be prepared from compounds of Formula (13) as described in SCHEME 1, and can be used as described in SCHEME 8 to prepare compounds of Formula I.

SCHEME 4

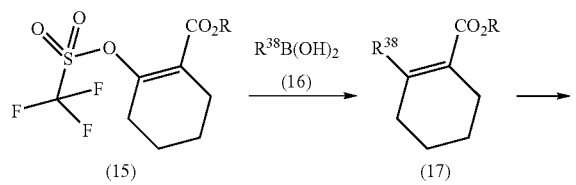

SCHEME 5

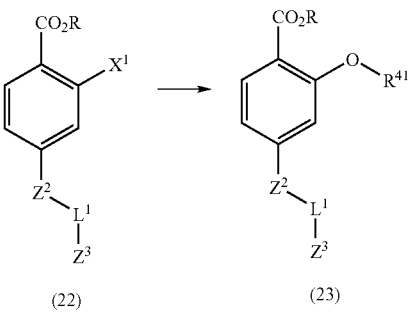

As shown in SCHEME 5, compounds of Formula (22), wherein R is alkyl, may be converted to compounds of Formula (23) by reacting the former, wherein $X^1$ is Cl, Br, I, or $CF_3SO_3$—, and compounds of Formula $R^{41}$—OH and a catalyst, with or without a first base. Examples of catalysts include copper(I) trifluoromethanesulfonate toluene complex, $PdCl_2$, $Pd(OAc)_2$, and $Pd_2(dba)_3$. Examples of first bases include triethylamine, N,N-diisopropylethylamine, $Cs_2CO_3$, $Na_2CO_3$, $K_3PO_4$, and mixtures thereof. Compounds of Formula (22) may also be converted to compounds of Formula (23) by reacting the former, when $X^1$ is Cl, F, or $NO_2$, and compounds of Formula $R^{41}$—OH with a first base. Examples of first bases include triethylamine, N,N-diisopropylethylamine, $Cs_2CO_3$, $Na_2CO_3$, $K_3PO_4$, and mixtures thereof.

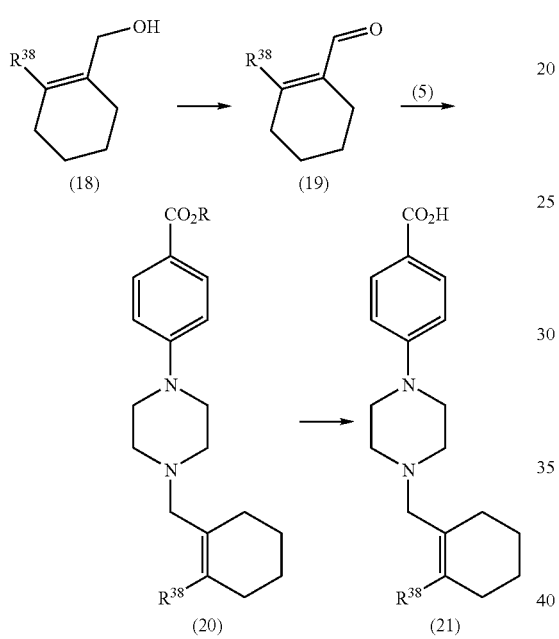

As shown in SCHEME 4, compounds of Formula (17) can be prepared from compounds of Formula (15) and compounds of Formula (16), wherein R is alkyl and $R^{38}$ is as described herein, using Suzuki coupling conditions known to those skilled in the art and readily available in the literature. Compounds of Formula (17) can be reduced to compounds of Formula (18) using a reducing agent such as $LiAlH_4$ in a solvent such as but not limited to diethyl ether or THF. Compounds of Formula (19) can be prepared from compounds of Formula (18) using Dess-Martin periodinane or Swern oxidation conditions known to those skilled in the art and readily available in the literature. Compounds of Formula (19) can be reacted with a compound of Formula (5) and a reducing agent to provide compounds of Formula (20). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, 1,2-dichloroethane, and dichloromethane or mixtures thereof. Compounds of Formula (21) can be prepared from compounds of Formula (20) as described in SCHEME 1, and can be used as described in SCHEME 8 to prepare compounds of Formula I.

SCHEME 6

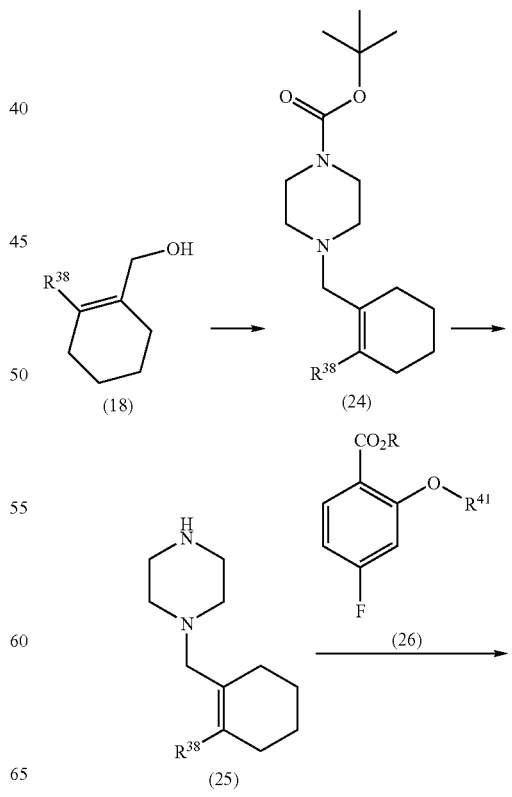

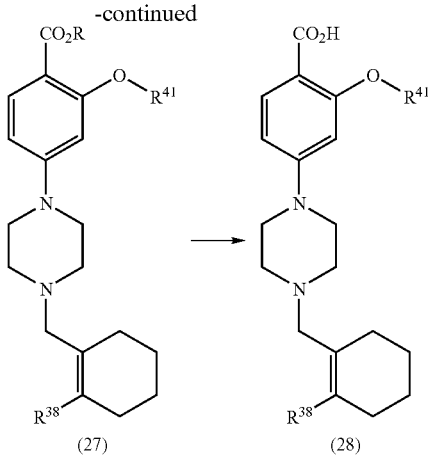

Compounds of Formula (18) can be reacted with mesyl chloride and a base such as but not limited to triethylamine, followed by N-t-butoxycarbonylpiperazine, to provide compounds of Formula (24). Compounds of Formula (25) can be prepared by reacting compounds of Formula (24) with triethylsilane and trifluoroacetic acid. Compounds of Formula (25) can be reacted with compounds of Formula (26) and $HK_2PO_4$ to provide compounds of Formula (27) in a solvent such as but not limited to dimethylsulfoxide. Compounds of Formula (28) can be prepared from compounds of Formula (27) as described in SCHEME 1, and can be used as described in SCHEME 8 to prepare compounds of Formula I.

SCHEME 7

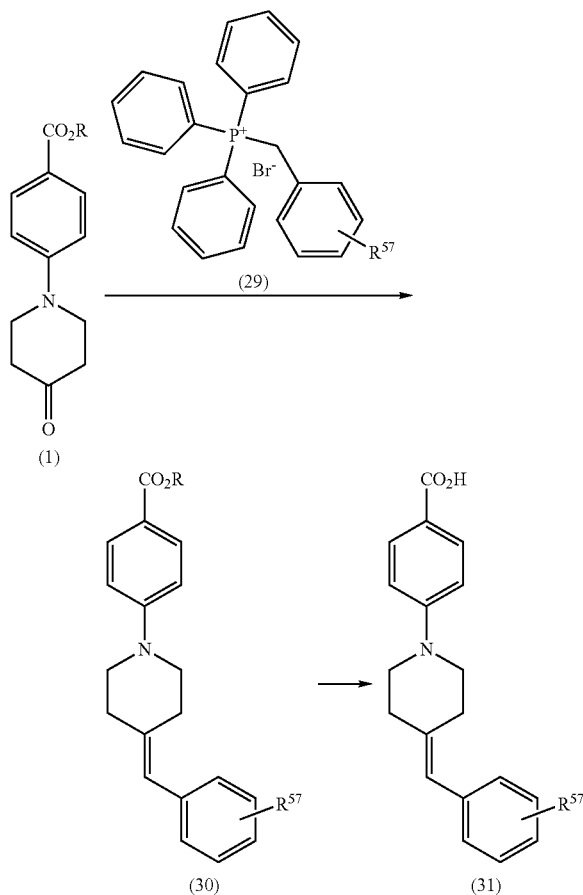

As shown in SCHEME 7, compounds of Formula (1) can be reacted with an appropriate triphenylphosphonium bromide of Formula (29) and a base such as but not limited to sodium hydride or n-butyllithium to provide compounds of Formula (30). The reaction is typically performed in a solvent such as THF or DMSO. Compounds of Formula (31) can be prepared from compounds of Formula (30) as described in SCHEME 1, and can be used as described in SCHEME 8 to prepare compounds of Formula I.

SCHEME 8

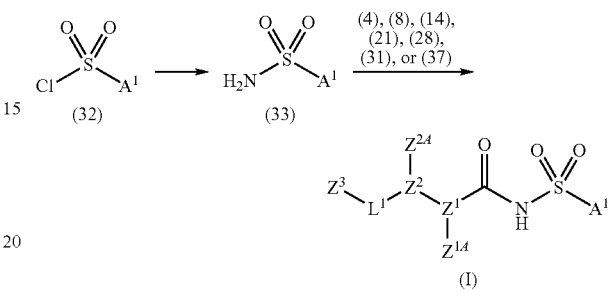

As shown in SCHEME 8, compounds of Formula (32), which can be prepared as described herein, may be converted to compounds of Formula (33) by reacting the former with ammonia. Compounds of Formula (33) may be converted to compounds of Formula (I) by reacting the former and compounds of Formula (4), (8), (14), (21), (28), (31), or (37) and a coupling agent, with or without a first base. Examples of coupling agents include 1-ethyl-3-[3-(dimethylamino)propyl]-carbodiimide hydrochloride, 1,1'-carbonyldiimidazole, and benzotriazol-1-yl-oxytripyrrolidinophosphonium hexafluorophosphate. Examples of first bases include triethylamine, N,N-diisopropylethylamine, 4-(dimethylamino)pyridine, and mixtures thereof

SCHEME 9

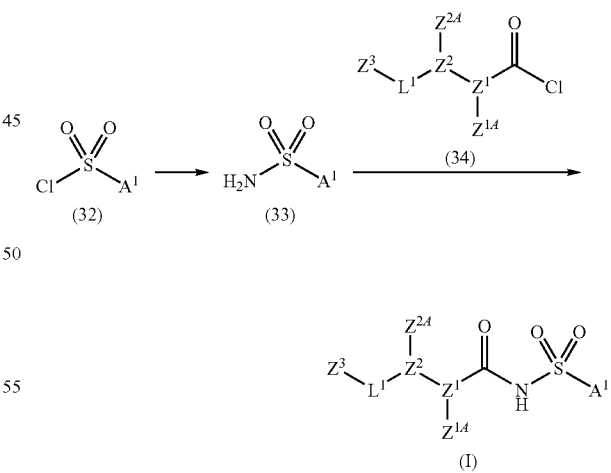

Compounds of Formula (33), prepared as described in SCHEME 1, may also be converted to compounds of Formula (I) by reacting the former and compounds of Formula (34) and a first base. Examples of first bases include but are not limited to sodium hydride, triethylamine, N,N-diisopropylethylamine, 4-(dimethylamino)pyridine, and mixtures thereof

SCHEME 10

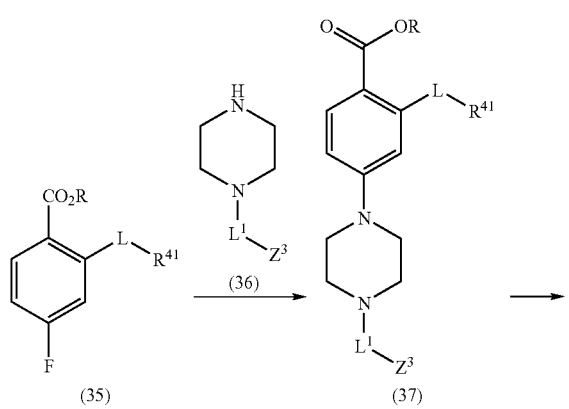

(35) (36) (37)

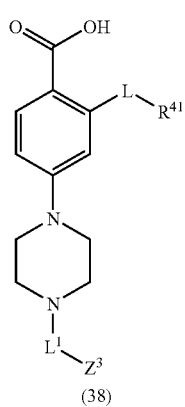

(38)

As shown in SCHEME 10, compounds of Formula (35), wherein L is a bond, alkyl, O, S, S(O), S(O)$_2$, NH, etc., can be reacted with compounds of Formula (36), to provide compounds of Formula (37). The reaction is typically performed at elevated temperatures in a solvent such as but not limited to dimethylsulfoxide, and may require the use of a base such as but not limited to potassium phosphate, potassium carbonate, and the like. Compounds of Formula (38) can be prepared from compounds of Formula (37) as described in SCHEME 1, and can be used as described in SCHEME 8 to prepare compounds of Formula I.

SCHEME 11

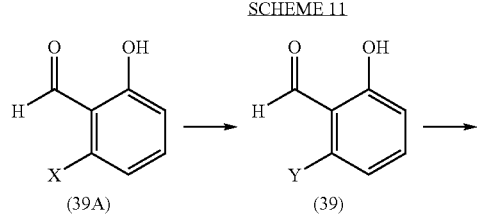

(39A) (39)

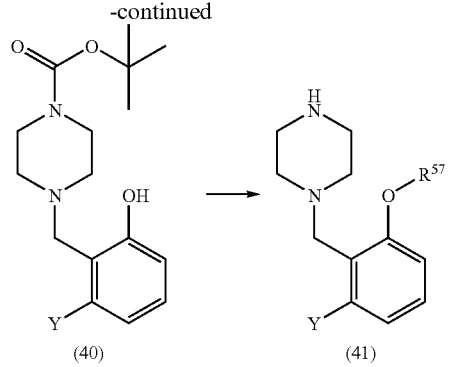

(40) (41)

Compounds of Formula (39), wherein Y is as described herein for substituents on Z$^3$, can be prepared from compounds of Formula (39A) wherein X is a halide or triflate, and Y—B(OH)$_2$ using Suzuki coupling conditions known to those skilled in the art and readily available in the literature. Compounds of Formula (39) can be reacted with tert-butyl piperazine-1-carboxylate and a reducing agent such as sodium triacetoxyborohydride to provide compounds of Formula (40). The reaction is typically performed in a solvent such as but not limited to methylene chloride. Compounds of Formula (41) can be prepared from compounds of Formula (40) by reacting the latter with R$^{57}$X, wherein X is a halide, and NaH in a solvent such as N,N-dimethylformamide, and then the resulting material can be treated with triethylsilane and trifluoroacetic acid in dichloromethane. Compounds of Formula (41) can be used as described in Scheme 10 wherein L$^1$-Z$^3$ is as shown in Formula (41).

SCHEME 12

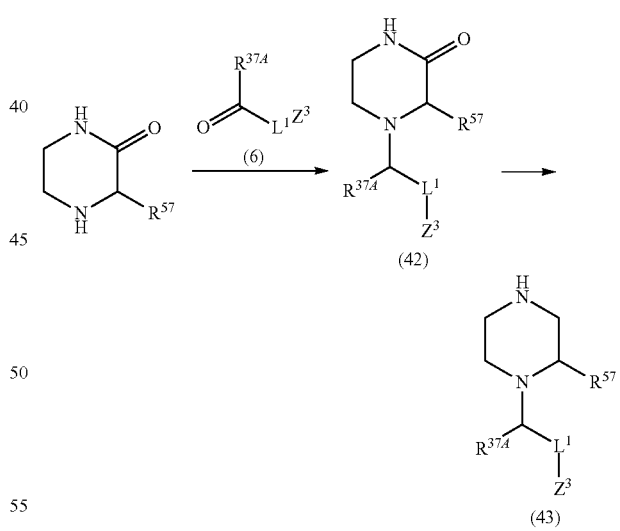

(42)

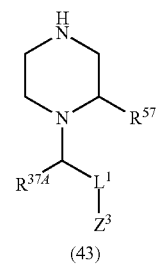

(43)

As shown in SCHEME 12, substituted piperazin-2-ones wherein R$^{57}$ is alkyl, can be reacted with compounds of Formula (6) and a reducing agent such as sodium triacetoxyborohydride in dichloromethane to provide compounds of Formula (42). Compounds of Formula (42) can be reduced to compounds of Formula (43) using a reducing agent such as but not limited to lithium aluminum hydride in a solvent such as but not limited to tetrahydrofuran. Compounds of Formula (43) can be used as described in Scheme 10 wherein L$^1$-Z$^3$ is as shown in Formula (43).

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

Example 1

4-[4-(cyclohexylmethyl)-4-methoxypiperidin-1-yl]-N-{5-({(1R)-3-(dimethylamino)-1-[(phenylthio)methyl]propyl}amino)-4-nitrothien-2-yl]sulfonyl}benzamide Example 1A (R)-benzyl 4-(dimethylamino)-1-hydroxy-4-oxobutan-2-ylcarbamate A solution of 3-(S)-((carbobenzyloxy)amino)-γ-butyrolactone (prepared according to the procedure described in McGarvey, G. J.; Williams, J. M.; Hiner, R. N.; Matsubara, Y.; Oh, T. J. Am. Chem. Soc. 1986, 108, 4943-4952, 7.72 g) in THF (100 mL) was saturated with gaseous dimethylamine, stirred at room temperature for 16 hours, and concentrated. The residue was filtered through a plug of silica gel eluting with 50% acetone in hexanes to give the desired product.

Example 1B (R)-benzyl 4-(dimethylamino)-4-oxo-1-(phenylthio)butan-2-ylcarbamate

A solution of EXAMPLE 1A (8.45 g) in toluene (15 mL) was treated with tributylphosphine (9.76 mL), and diphenyldisulfide (7.30 g) and was heated to 80° C. for 16 hours. The reaction mixture was concentrated and purified by column chromatography on silica gel eluting with a gradient of 0-50% ethyl acetate in hexanes to give the desired product.

Example 1C (R)-3-amino-N,N-dimethyl-4-(phenylthio)butanamide

A suspension of EXAMPLE 1B (10.60 g) in 50 mL 30% HBr/acetic acid was stirred at room temperature overnight. The resulting homogeneous reaction mixture was concentrated, diluted with water (200 mL) and 5% HCl (100 mL), and washed with diethyl ether (3×). The aqueous phase was adjusted to pH ~8-9 with solid $Na_2CO_3$ and extracted with dichloromethane (5×). The combined organic phases were dried ($MgSO_4$), filtered, and concentrated to give the desired product.

Example 1D (R)-$N^1$,$N^1$-dimethyl-4-(phenylthio)butane-1,3-diamine

A solution of EXAMPLE 1C (8.68 g) in THF (200 mL) was treated with $BH_3$-dimethylsulfide (18.2 mL) at room temperature, stirred overnight, treated slowly with methanol (20 mL), followed by 2N HCl (50 mL), stirred overnight, and concentrated. The resulting residue was purified by silica gel chromatography eluting with 5% 7N $NH_3/CH_3OH$ in dichloromethane to give the desired product.

Example 1E (R)-5-(4-(dimethylamino)-1-(phenylthio)butan-2-ylamino)-4-nitrothiophene-2-sulfonamide 2-Chloro-3-nitrothiophene-5-sulfonamide (2.18 g), EXAMPLE 1D (1.14 g), and triethylamine (1 g) were stirred in dioxane (30 mL) at 90° C. for 24 hours. The solution was diluted with ethyl acetate, washed with $NaH_2PO_4$ solution and brine, dried over $Na_2SO_4$, filtered and concentrated. The product was triturated from ethyl acetate.

Example 1F ethyl 4-(4-(cyclohexylmethyl)-4-hydroxypiperidin-1-yl)benzoate

A solution of cyclohexylmethylmagnesium bromide (1.90 mL of a 2M solution in THF) at −78° C. was treated with ethyl 4-(4-oxo-1-piperidinyl)benzoate (prepared according to the procedure described in Synthesis 1981, 606-608, 0.30 g), and was allowed to warm to room temperature overnight. The reaction mixture was partitioned between ethyl acetate and saturated aqueous $NH_4Cl$ and the aqueous layer was extracted with ethyl acetate (2×). The combined organic layers were dried ($MgSO_4$), filtered, and concentrated. The resulting residue was purified by silica gel chromatography eluting with 20% ethyl acetate to give the product.

Example 1G ethyl 4-(4-(cyclohexylmethyl)-4-methoxypiperidin-1-yl)benzoate

A solution of EXAMPLE 1F (380 mg) in THF (5 mL) was treated with NaH (96 mg, 60% dispersion in mineral oil), heated to 50° C. for 2 hours, and treated with hexamethylphosphoramide (1 mL) followed by MeI (1 mL). The reaction mixture was refluxed overnight, cooled to 0° C., and diluted with saturated aqueous $NaHSO_4$ solution (10 mL). The resulting two-phase mixture was separated, the aqueous phase was extracted twice with ether, and the combined organic layers washed with water and brine. After drying over $MgSO_4$, the mixture was concentrated in vacuo and purified by silica gel chromatography eluting with 15% ethyl acetate in hexanes.

Example 1H 4-(4-(cyclohexylmethyl)-4-methoxypiperidin-1-yl)benzoic acid

A solution of EXAMPLE 1G (300 mg) in dioxane (5 mL) was treated with 1N NaOH (2 mL), stirred overnight, acidified with 1N HCl, extracted with ethyl acetate (3×), dried ($MgSO_4$), and filtered. Concentration of the filtrate gave the desired product.

Example 1I

4-[4-(cyclohexylmethyl)-4-methoxypiperidin-1-yl]-N-{5-({(1R)-3-(dimethylamino)-1-[(phenylthio)methyl]propyl}amino)-4-nitrothien-2-yl]sulfonyl}benzamide EXAMPLE 1E (60 mg), EXAMPLE 1H (65 mg), 1-ethyl-3-[3-(dimethylamino)propyl]-carbodiimide hydrochloride (65 mg), and 4-dimethylaminopyridine (22 mg) were stirred in CH$_2$Cl$_2$ (4 mL) for 24 hours. The reaction was cooled and chromatographed on silica gel with 50-100% ethyl acetate in hexanes followed by Jan. 10, 1989 triethylamine/methanol/ethyl acetate. $^1$H NMR (400 MHz, DMSO-d$_6$) δ 9.06 (br s, 1H), 7.77 (d, 2H), 7.44 (s, 1H), 7.35 (d, 2H), 7.26 (dd, 2H), 7.11 (t, 1H), 6.84 (d, 2H), 3.60 (m, 1H), 3.45 (m, 2H), 3.32 (m, 1H), 3.07 (m, 4H), 2.97 (m, 2H), 2.77 (m, 1H), 2.66 (m, 1H), 2.43 (s, 6H), 2.05 (m, 2H), 1.75 (m, 2H), 1.59 (m, 2H), 1.48 (m, 2H), 1.33 (m, 2H), 1.17 (m, 6H), 0.94 (m, 2H).

Example 2

N-{[5-({(1R)-3-(dimethylamino)-1-[(phenylthio)methyl]propyl}amino)-4-nitrothien-2-yl]sulfonyl}-4-[4-methoxy-4-(3-methylbenzyl)piperidin-1-yl]benzamide Example 2A ethyl 4-(4-hydroxy-4-(3-methylbenzyl)piperidin-1-yl)benzoate This EXAMPLE was prepared by substituting 3-methylbenzylmagnesium chloride for cyclohexylmethylmagnesium bromide in EXAMPLE 1F.

Example 2B ethyl 4-(4-methoxy-4-(3-methylbenzyl)piperidin-1-yl)benzoate

This EXAMPLE was prepared by substituting EXAMPLE 2A for EXAMPLE 1F in EXAMPLE 1G.

Example 2C 4-(4-methoxy-4-(3-methylbenzyl)piperidin-1-yl)benzoic acid

This EXAMPLE was prepared by substituting EXAMPLE 2B for EXAMPLE 1G in EXAMPLE 1H.

Example 2D

N-{[5-({(1R)-3-(dimethylamino)-1-[(phenylthio)methyl]propyl}amino)-4-nitrothien-2-yl]sulfonyl}-4-[4-methoxy-4-(3-methylbenzyl)piperidin-1-yl]benzamide This EXAMPLE was prepared by substituting EXAMPLE 2C for EXAMPLE 1H in EXAMPLE 1I. $^1$H NMR (400 MHz, DMSO-d$_6$) δ 9.00 (br s, 1H), 7.76 (d, 2H), 7.44 (s, 1H), 7.35 (d, 2H), 7.26 (dd, 2H), 7.16 (m, 2H), 6.89 (m, 3H), 6.82 (d, 2H), 4.05 (m, 1H), 3.61 (m, 1H), 3.48 (m, 2H), 3.32 (m, 2H), 3.27 (s, 3H), 3.17 (s, 2H), 3.07 (m, 1H), 2.92 (m, 2H), 2.74 (s, 6H), 2.27 (s, 3H), 2.07 (m, 2H), 1.67 (m, 2H), 1.52 (m, 2H).

Example 3

N-{[5-({(1R)-3-(dimethylamino)-1-[(phenylthio)methyl]propyl}amino)-4-nitrothien-2-yl]sulfonyl}-4-[4-(3,3-diphenylprop-2-enyl)piperazin-1-yl]benzamide Example 3A ethyl 4-(4-(3,3-diphenylallyl)piperazin-1-yl)benzoate A suspension of ethyl 4-piperazin-1-ylbenzoate (1.36 g) and 3,3-diphenylacrylaldehyde (1.56 g) in dichloromethane (10 mL) and methanol (10 mL) was treated with polymer-supported cyanoborohydride (2.47 mmol/g, 6 g), shaken at room temperature for 24 hours, and filtered. The resin was washed with 1:1 dichloromethane/methanol (10 mL×3) and the combined filtrates were concentrated. The concentrate was purified by silica gel chromatography eluting with a gradient from 10%-50% ethyl acetate/hexanes to provide the desired product.

Example 3B 4-(4-(3,3-diphenylallyl)piperazin-1-yl)benzoic acid

This EXAMPLE was prepared by substituting EXAMPLE 3A for EXAMPLE 1G in EXAMPLE 1H.

Example 3C

N-{[5-({(1R)-3-(dimethylamino)-[4(phenylthio)methyl]propyl}amino)-4-nitrothien-2-yl]sulfonyl}-4-[4-(3,3-diphenylprop-2-enyl)piperazin-1-yl]benzamide This EXAMPLE was prepared by substituting EXAMPLE 3B for EXAMPLE 1H in EXAMPLE 1I. $^1$H NMR (500 MHz, DMSO-d$_6$) δ 10.25 (br s, 1H), 9.08 (br s, 1H), 7.78 (d, 2H), 7.43 (m, 2H), 7.35 (m, 3H), 7.30 (d, 2H), 7.20-7.29 (m, 5H), 7.16 (m, 3H), 6.84 (d, 2H), 6.22 (t, 1H), 3.59 (m, 1H), 3.45 (m, 4H), 3.32 (m, 4H), 3.03 (m, 4H), 2.78 (m, 1H), 2.65 (m, 1H), 2.42 (s, 6H), 2.07 (m, 2H).

Example 4

4-{4-[(4'-chloro-1,1'-biphenyl-2-yl)methyl]piperazin-1-yl}-N-[(4-{[2-(phenylthio)ethyl]amino}piperidin-1-yl)sulfonyl]benzamide Example 4A ethyl 4-(piperazin-1-yl)benzoate A suspension of piperazine (129.2 g, 1.5 mol), ethyl-4-fluorobenzoate (84 g, 0.5 mol), and potassium carbonate (103.65 g, 0.75 mol) in DMSO (200 mL) was stirred at 120° C. under N$_2$ for six hours. The reaction mixture was then cooled to room temperature, poured into water (800 mL), and stirred for 30 minutes. The desired product was collected by filtration and carried to the next step without further purification.

Example 4B ethyl 4-(4-(2-bromobenzyl)piperazin-1-yl)benzoate

A solution of EXAMPLE 4A (23.43 g, 100.0 mmol), 2-bromobenzyl bromide (26.24 g, 105.0 mmol) and diisopropylethylamine (20.94 mL, 120.0 mmol) in acetonitrile (200 mL) was stirred at room temperature for two hours. The resulting precipitate was collected by filtration to give the desired product, which was used without further purification.

Example 4C ethyl 4-(4-((4'-chlorobiphenyl-2-yl)methyl)piperazin-1-yl)benzoate

A suspension of EXAMPLE 4B (13.83 g, 34.3 mmol), 4-chlorophenylboronic acid (7.04 g, 45.0 mmol), bis(triphenylphosphine)palladium(II) dichloride (0.481 g, 0.686 mmol, 2 mol %) and aqueous 2M Na$_2$CO$_3$ (22.5 mL, 45.0 mmol) in dimethoxyethane/H$_2$O/ethanol (7:3:2, 200 mL) was heated at 90° C. for 4.5 hours and diluted with ethyl acetate (200 mL). The layers were separated and the organic phase was dried (MgSO$_4$), filtered, and concentrated. The residue was purified by silica gel chromatography eluting with a gradient from 5%-40% ethyl acetate/hexanes to give the desired product.

Example 4D 4-(4-((4'-chlorobiphenyl-2-yl)methyl)piperazin-1-yl) benzoic acid

A suspension of EXAMPLE 4C (13.0 g, 29.9 mmol) and LiOH monohydrate (3.78 g, 90.0 mmol) in dioxane (250 mL) and water (100 mL) was heated at 95° C. for 16 hours, concentrated to dryness, treated with water (600 mL), heated to 80° C., and filtered. The filtrate was treated with 1M HCl (90 mL) and the resulting precipitate was collected by filtration and dried to give the desired product.

Example 4E tert-butyl 4-oxopiperidin-1-ylsulfonylcarbamate

Chlorosulfonyl isocyante (1.044 g, 7.353 mmol) was added to dichloromethane (20 mL) and the mixture was cooled to 0° C. Tert-butanol (544 mg, 7.353 mmol) in dichloromethane (3 mL) was added and, the solution was stirred at 0° C. for 30 minutes. This solution was then added to a separate flask containing 4-piperidone hydrochloride (1.00 g, 7.353 mmol) and triethylamine (3.1 mL, 22.059 mmol) in dichloromethane (20 mL), which had been cooled to 0° C. After addition, the solution was allowed to warm to room temperature and stir for two hours. The mixture was then partitioned between dichloromethane and saturated aqueous ammonium chloride. The aqueous layer was extracted with dichloromethane three times, and the combined organic extracts were dried over anhydrous magnesium sulfate. The solution was concentrated and purified by flash column chromatography on silica gel with 0% ethyl acetate in dichloromethane increasing to 20% ethyl acetate in dichloromethane.

Example 4F 4-oxopiperidine-1-sulfonamide

EXAMPLE 4E (500 mg) was dissolved in 1,4-dioxane (4 mL), treated with 4M HCl (4 mL), and stirred at room temperature for three hours. The solution was concentrated and purified by flash column chromatography on silica gel with 0% acetonitrile (dichloromethane) increasing to 40% acetonitrile (dichloromethane).

Example 4G 4-(4-((4'-chlorobiphenyl-2-yl)methyl)piperazin-1-yl)-N-(4-oxopiperidin-1-ylsulfonyl)benzamide This EXAMPLE was prepared by substituting EXAMPLE 4F for EXAMPLE 1E and EXAMPLE 4D for EXAMPLE 1H in EXAMPLE 1I.

Example 4H

4-{4-[(4'-chloro-1,1'-biphenyl-2-yl)methyl]piperazin-1-yl}-N-[(4-{[2-(phenylthio)ethyl]amino}piperidin-1-yl)sulfonyl]benzamide EXAMPLE 4G (100 mg, 0.176 mmol), 2-(phenylthio)ethanamine (30 mg, 0.194 mmol), sodium triacetoxyborohydride (56 mg, 0.264 mmol), and acetic acid (11 μL, 0.194 mmol) were added to 1,2-dichloroethane (2 mL) and mixed at room temperature for six hours. The solvent was removed under vacuum, and the residue was treated with water. The precipitate was filtered, dried, dissolved in dimethylsulfoxide/methanol with a couple of drops of triethylamine, and purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). $^1$H NMR (400 MHz, DMSO-d$_6$) δ 11.53 (bs, 1H), 8.92 (bs, 2H), 7.76 (d, 2H), 7.70 (bs, 1H), 7.48 (m, 4H), 7.38-7.26 (m, 7H), 7.24-7.17 (m, 1H), 4.18 (bs, 2H), 3.74 (d, 4H), 3.21-3.16 (m, 6H), 3.08 (bs, 4H), 2.87 (t, 4H), 2.04 (d, 2H), 1.48 (m, 2H).

Example 5

N-[(4-{acetyl[2-(phenylthio)ethyl]amino}piperidin-1-yl)sulfonyl]-4-{4-[(4'-chloro-1,1'-biphenyl-2-yl)methyl]piperazin-1-yl}benzamide EXAMPLE 4H (30 mg, 0.0426 mmol), acetic anhydride (4.3 mg, 0.0426 mmol), and triethylamine (18 μL, 0.128 mmol) were added to dichloromethane (1 mL) and stirred at room temperature for two hours. The solvent was removed under vacuum, dissolved in dimethylsulfoxide/methanol, and purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). $^1$H NMR (400 MHz, DMSO-d$_6$) δ 11.50 (bs, 1H), 7.82 (d, 2H), 7.74 (bs, 1H), 7.52 (d, 4H), 7.40 (t, 4H), 7.35-7.25 (m, 3H), 7.18 (dt, 1H), 6.94 (d, 2H), 4.26 (bs, 2H), 3.96 (t, 1H), 3.75 (d, 4H), 3.28 (dt, 4H), 3.10-2.85 (m, 8H), 2.04 (s, 2H), 1.88 (s, 1H), 1.75-1.56 (m, 4H).

Example 6

4-{4-[(4'-chloro-1,1'-biphenyl-2-yl)methyl]piperazin-1-yl}-N-[(4-{methyl[2-(phenylthio)ethyl]amino}piperidin-1-yl)sulfonyl]benzamide EXAMPLE 4H (30 mg, 0.0426 mmol), formaldehyde (37% solution in water, 10 μL, 0.128 mmol), and sodium triacetoxyborohydride (14 mg, 0.0639 mmol) were added to acetonitrile (0.8 mL) and water (0.2 mL). The solvent was removed under vacuum, dissolved in dimethylsulfoxide/methanol, and purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A).
$^1$H NMR (400 MHz, DMSO-d$_6$) δ 11.32 (bs, 1H), 9.84 (bs, 1H), 7.54 (d, 2H), 7.49 (bs, 1H), 7.26 (d, 4H), 7.12 (d, 4H), 7.11-7.07 (m, 3H), 6.99 (t, 1H), 6.69 (d, 2H), 3.98 (bs, 2H), 3.56 (d, 2H), 3.33-3.11 (m, 4H), 3.09-2.91 (m, 7H), 2.68 (t, 4H), 2.49 (s, 3H), 1.72 (d, 2H), 1.38 (bs, 2H).

Example 7

4-{4-[(4'-chloro-1,1'-biphenyl-2-yl)methyl]piperazin-1-yl}-N-{[5-({(1R)-3-[isopropyl(methyl)amino]-1-[(phenylthio)methyl]propyl}amino)-4-nitrothien-2-yl]sulfonyl}benzamide Example 7A (R)-benzyl 4-oxo-1-(phenylthio)butan-2-ylcarbamate To a 100 mL three necked round-bottom flask charged with EXAMPLE 1B (3.75 g, 10.0 mmol) and bis(cyclopentadienyl)zirconium chloride hydride (3.85 g, 15.0 mmol) was added 50 mL of anhydrous THF through a syringe under argon (the air in the system was replaced by vacuum-argon replacement three times). The mixture was stirred at room temperature for 20 minutes, and it became a clear solution during the stirring. TLC showed the reaction was complete and the mixture was concentrated. The residue was loaded on a silica gel pad and flushed with hexane/ethyl acetate (1:1, 300 mL). Concentration gave title compound.

Example 7B (R)-benzyl 4-(isopropyl(methyl)amino)-1-(phenylthio)butan-2-ylcarbamate To a 250 mL round-bottom flask containing EXAMPLE 7A (2.87 g, 8.71 mmol) was added 50 mL of 1,2-dichloroethane and methylisopropylamine (1.92 g, 26.25 mmol) and sodium triacetoxyborohydride (3.0 g, 14.1 mmol). The mixture was stirred at room temperature under $N_2$ for two hours. The mixture was diluted with ethyl acetate (200 mL) and washed with 2N NaOH, water, brine and dried over $Na_2SO_4$. The solvent was removed under vacuum to give title compound.

Example 7C (R)-$N^1$-isopropyl-$N^1$-methyl-4-(phenylthio)butane-1,3-diamine

EXAMPLE 7B (0.56 g, 1.47 mmol) was dissolved in acetonitrile (10 mL) and trimethylsilyl iodide (400 μL) was added. The mixture was stirred at room temperature overnight. The mixture was quenched with methanol, concentrated under vacuum, and the residue was dissolved in ethyl acetate (200 mL) and washed with 1.5% HCl (50 mL) twice. The combined aqueous layers were basified with solid NaOH and extracted with ethyl acetate (100 mL×3). The combined extracts were washed with brine and dried over $Na_2SO_4$. Evaporation of solvent gave title compound.

Example 7D (R)-5-(4-(isopropyl(methyl)amino)-1-(phenylthio)butan-2-ylamino)-4-nitrothiophene-2-sulfonamide To a 20 mL vial containing EXAMPLE 7C (0.43 g, 1.69 mmol) was added 2-chloro-3-nitrothiophene-5-sulfonamide (0.409 g, 1.69 mmol) and DMSO (5 mL) followed by diisopropylethylamine (1 mL, 5.74 mmol). The mixture was stirred at 60° C. overnight, and The mixture was diluted with ethyl acetate (150 mL) and washed with aqueous $NaHCO_3$, water and brine. After drying over $Na_2SO_4$ and evaporation of solvent, the residue was loaded on a silica gel column and eluted with ethyl acetate/dichloromethane (saturated with $NH_3$) to give title compound.

Example 7E

4-{4-[(4'-chloro-1,1'-biphenyl-2-yl)methyl]piperazin-1-yl}-N-{[5-({(1R)-3-[isopropyl(methyl)amino]-1-[(phenylthio)methyl]propyl}amino)-4-nitrothien-2-yl]sulfonyl}benzamide The title compound was prepared as in EXAMPLE 1I, replacing EXAMPLE 1E and EXAMPLE 1H with EXAMPLE 7D and EXAMPLE 4D, respectively. $^1$H NMR (300 MHz, DMSO-$d_6$) δ ppm 8.98 (m, 1H), 7.83 (m, 2H), 7.70 (m, 1H), 7.52 (m, 4H), 7.35 (m, 6H), 7.16 (m, 4H), 6.96 (m, 2H), 3.77 (m, 2H), 3.59 (m, 5H), 3.21 (m, 7H), 2.64 (t, 3H), 2.52 (d, 6H), 1.19 (d, 4H).

Example 8

4-(4-{[2-(4-chlorophenyl)cyclohex-1-en-1-yl]methyl}piperazin-1-yl)-N-{[5-({(1R)-3-[isopropyl(methyl)amino]-1-[(phenylthio)methyl]propyl}amino)-4-nitrothien-2-yl]sulfonyl}benzamide Example 8A ethyl 2-(trifluoromethylsulfonyloxy)cyclohex-1-enecarboxylate To a cooled (0° C.) stirring suspension of NaH (0.983 g 60% in mineral oil, washed with hexane three times) in ether (50 ml) was added ethyl 2-oxocyclohexanecarboxylate (3.2 g, 20.5 mmol). The mixture was stirred at 0° C. for 30 minutes before the addition of trifluoromethanesulfonic anhydride (4.2 mL, 25 mmol). The mixture was then stirred at room temperature overnight. The mixture was diluted with ether (200 mL) and washed with 5% HCl, water and brine. After drying over $Na_2SO_4$, evaporation of solvent gave crude product which was used without further purification.

Example 8B ethyl 2-(4-chlorophenyl)cyclohex-1-enecarboxylate

To a solution of EXAMPLE 8A (2.88 g, 10 mmol), 4-chlorophenylboronic acid (1.88 g, 12 mmol) and tetrakis(triphenylphosphine)palladium(0) (0.578 g, 0.5 mmol) in toluene (40 ml) and ethanol (10 ml) was added 2N $Na_2CO_3$ (10 mL). The mixture was stirred at reflux overnight. The mixture was diluted ether (300 mL) and washed with water, brine and dried over $Na_2SO_4$. After evaporation of solvent, the residue was loaded on a column and eluted with 3% ethyl acetate in hexane to give title compound.

Example 8C (2-(4-chlorophenyl)cyclohex-1-enyl)methanol

To a solution of EXAMPLE 8B (1.6 g, 6.38 mmol) in ether (20 mL) was added $LiAlH_4$ (1.2 g, 32 mmol). The mixture was stirred at room temperature for four hours. The mixture was acidified carefully with 5% HCl and extracted with ethyl acetate (100 mL×3) and washed with water, brine and dried over Na$_2$SO$_4$. After evaporation, the crude product was loaded on a column and eluted with 10% ethyl acetate in hexane to give title compound.

Example 8D 2-(4-chlorophenyl)cyclohex-1-enecarbaldehyde

To a solution of oxalyl chloride (1.1 g, 8.63 mmol) in dichloromethane (30 ml) at −78° C. was added dimethylsulfoxide (6.12 mL, 86 mmol). The mixture was stirred at −78° C. for 30 minutes, and then a solution of EXAMPLE 8C (1.2 g, 5.75 mmol) in dichloromethane (10 mL) was added. The mixture was stirred at −78° C. for two hours before the addition of triethylamine (10 mL). The mixture was stirred overnight and the temperature was allowed to rise to room temperature. The mixture was diluted with ether (300 mL) and washed with water, brine and dried over Na$_2$SO$_4$. Evaporation of solvent and column purification (5% ethyl acetate in hexane) gave title compound.

Example 8E ethyl 4-(4-((2-(4-chlorophenyl)cyclohex-1-enyl)methyl)piperazin-1-yl)benzoate To a solution of EXAMPLE 8D (100 mg, 0.484 mmol) and EXAMPLE 4A (177 mg, 0.484 mmol) in 1,2-dichloroethane (10 mL) was added sodium triacetoxyborohydride (154 mg, 0.726 mmol). The mixture was stirred at room temperature overnight. The mixture was diluted with ethyl acetate (200 mL) and washed with 2% NaOH, water and brine. After drying over Na$_2$SO$_4$, the solvent was concentrated under vacuum, and the residue was loaded on a column and eluted with 30% ethyl acetate in hexane to give title compound.

Example 8F 4-(4-((2-(4-chlorophenyl)cyclohex-1-enyl)methyl)piperazin-1-yl)benzoic acid To a solution of EXAMPLE 8E (254 mg, 0.457 mmol) in tetrahydrofuran (4 mL), methanol (2 mL) and water (2 mL) was added lithium hydroxide monohydrate (126 mg, 3 mmol). The mixture was stirred at room temperature overnight. The mixture was then neutralized with 5% HCl and diluted with ethyl acetate (200 mL). After washing with brine, it was dried over Na$_2$SO$_4$. Evaporation of solvent gave title compound.

Example 8G 4-(4-{[2-(4-chlorophenyl)cyclohex-1-en-1-yl]methyl}piperazin-1-yl)-N-{[5-({(1R)-3-[isopropyl(methyl)amino]-1-[(phenylthio)methyl]propyl}amino)-4-nitrothien-2-yl]sulfonyl}benzamide The title compound was prepared as in EXAMPLE 1I, replacing EXAMPLE 1E and EXAMPLE 1H with EXAMPLE 7D and EXAMPLE 8F respectively. $^1$H NMR (300 MHz, DMSO-d$_6$) δ ppm 8.97 (m, 1H), 7.83 (m, 2H), 7.68 (m, 1H), 7.42 (m, 2H), 7.30 (m, 2H), 7.17 (m, 5H), 6.97 (m, 2H), 3.91 (m, 2H), 3.66 (m, 3H), 3.18 (m, 7H), 2.87 (m, 3H), 2.64 (t, 3H), 2.51 (d, 6H), 2.24 (m, 4H), 1.72 (m, 3H), 1.18 (m, 6H).

Example 9

4-(4-{[2-(4-chlorophenyl)-5,5-dimethylcyclohex-1-en-1-yl]methyl}piperazin-1-yl)-N-{[5-({(1R)-3-[isopropyl(methyl)amino]-1-[(phenylthio)methyl]propyl}amino)-4-nitrothien-2-yl]sulfonyl}benzamide

Example 9A methyl 5,5-dimethyl-2-oxocyclohexanecarboxylate

To a suspension of hexane-washed NaH (0.72 g, 60%, 18 mmol) in tetrahydrofuran (30 mL) was added a solution of 4,4-dimethylcyclohexanone (2.0 g, 15.6 mmol) in tetrahydrofuran (20 mL). The suspension was stirred at room temperature for 30 minutes. Then dimethylcarbonate (6.31 mL, 75 mmol) was added dropwise by syringe. The mixture was heated to reflux for four hours. The mixture was acidified with 5% HCl and extracted with dichloromethane (100 mL×3) and washed with water, brine, and dried over Na$_2$SO$_4$. After concentration, the crude product was loaded on a column and eluted with 10% ethyl acetate in hexane to give title compound.

Example 9B methyl 5,5-dimethyl-2-(trifluoromethylsulfonyloxy)cyclohex-1-enecarboxylate The title compound was prepared as in EXAMPLE 8A by substituting ethyl 2-oxocyclohexanecarboxylate with EXAMPLE 9A.

Example 9C methyl 2-(4-chlorophenyl)-5,5-dimethylcyclohex-1-enecarboxylate

The title compound was prepared as in EXAMPLE 8B by substituting EXAMPLE 8A with EXAMPLE 9B.

Example 9D (2-(4-chlorophenyl)-5,5-dimethylcyclohex-1-enyl)methanol

The title compound was prepared as in EXAMPLE 8C by substituting EXAMPLE 8B with EXAMPLE 9C.

Example 9E 2-(4-chlorophenyl)-5,5-dimethylcyclohex-1-enecarbaldehyde

The title compound was prepared as in EXAMPLE 8D by substituting EXAMPLE 8C with EXAMPLE 9D.

Example 9F ethyl 4-(4-((2-(4-chlorophenyl)-5,5-dimethylcyclohex-1-enyl)methyl)piperazin-1-yl)benzoate The title compound was prepared as in EXAMPLE 8E by substituting EXAMPLE 8D with EXAMPLE 9E.

Example 9G 4-(4-((2-(4-chlorophenyl)-5,5-dimethylcyclohex-1-enyl)methyl)piperazin-1-yl)benzoic acid The title compound was prepared as in EXAMPLE 8F by substituting EXAMPLE 8E with EXAMPLE 9F.

Example 9H 4-(4-{[2-(4-chlorophenyl)-5,5-dimethylcyclohex-1-en-1-yl]methyl}piperazin-1-yl)-N-{[5-({(1R)-3-[isopropyl(methyl)amino]-1-[(phenylthio)methyl]propyl}amino)-4-nitrothien-2-yl]sulfonyl}benzamide The title compound was prepared as in EXAMPLE 1I, replacing EXAMPLE 1E and EXAMPLE 1H with EXAMPLE 7D and EXAMPLE 9G, respectively. $^1$H NMR (300 MHz, DMSO-$d_6$) δ ppm 8.96 (m, 1H), 7.83 (m, 2H), 7.67 (m, 1H), 7.42 (m, 2H), 7.29 (m, 2H), 7.17 (m, 6H), 6.97 (m, 2H), 3.90 (m, 2H), 3.61 (m, 8H), 3.19 (m, 3H), 2.65 (m, 3H), 2.23 (m, 5H), 2.04 (m, 2H), 1.48 (m, 2H), 1.19 (m, 6H), 1.00 (s, 6H).

Example 10

N-{[(5Z)-5-(acetylimino)-4-methyl-4,5-dihydro-1,3,4-thiadiazol-2-yl]sulfonyl}-4-{4-[(4'-chloro-1,1'-biphenyl-2-yl)methyl]piperazin-1-yl}benzamide This EXAMPLE was prepared by substituting EXAMPLE 4D for EXAMPLE 1H and (Z)-N-(3-methyl-5-sulfamoyl-1,3,4-thiadiazol-2(3H)-ylidene)acetamide for EXAMPLE 1E in EXAMPLE 1I. $^1$H NMR (300 MHz, DMSO-$d_6$) δ 7.74 (d, 2H), 7.48 (m, 5H), 7.38 (m, 2H), 7.24 (m, 1H), 6.83 (d, 2H), 3.84 (s, 2H), 3.17 (m, 4H), 2.40 (m, 4H), 1.82 (s, 6H).

Example 11

N-{[2-(acetylamino)-4-methyl-1,3-thiazol-5-yl]sulfonyl}-4-{4-[(4'-chloro-1,1'-biphenyl-2-yl)methyl]piperazin-1-yl}benzamide

Example 11A

N-(4-methyl-5-sulfamoylthiazol-2-yl)acetamide

2-Acetamido-4-methylthiazole-5-sulfonyl chloride (0.50 g, 1.96 mmol) was dissolved in THF (7 mL), cooled to 0° C., and concentrated NH$_4$OH (0.7 mL) was added. After 3 hours the reaction was concentrated, diluted with water, and extracted with CHCl$_3$/methanol. The organic layer was dried over Na$_2$SO$_4$. Filtration and concentration gave the product that was used EXAMPLE 11B.

Example 11B

N-{[2-(acetylamino)-4-methyl-1,3-thiazol-5-yl]sulfonyl}-4-{4-[(4'-chloro-1,1'-biphenyl-2-yl)methyl]piperazin-1-yl}benzamide This EXAMPLE was prepared by substituting EXAMPLE 4D for EXAMPLE 1H and EXAMPLE 11A for EXAMPLE 1E in EXAMPLE 1I, except here the purification was done by preparative HPLC using a C18 column, 250×50 mm, 10μ, and eluting with a gradient of 20-100% CH$_3$CN vs. 0.1% TFA in water, giving the product as a trifluoroacetate salt. $^1$H NMR (300 MHz, DMSO-$d_6$) δ 12.60 (s, 1H), 12.30 (v br s, 1H), 9.60 (v br s, 1H), 7.80 (d, 2H), 7.75 (br s, 1H), 7.52 (m, 4H), 7.40 (d, 2H), 7.36 (m, 1H), 6.94 (d, 2H), 4.38 (br s, 1H), 3.85 (br s, 1H), 3.40-2.80 (envelope, 8H), 2.52 (s, 3H), 2.18 (s, 3H).

Example 12

N-({5-[(benzoylamino)methyl]thien-2-yl}sulfonyl)-4-{4-[(4'-chloro-1,1'-biphenyl-2-yl)methyl]piperazin-1-yl}benzamide

Example 12A

N-((5-sulfamoylthiophen-2-yl)methyl)benzamide

This EXAMPLE was prepared by substituting 5-(benzamidomethyl)thiophene-2-sulfonyl chloride for 2-acetamido-4-methylthiazole-5-sulfonyl chloride in EXAMPLE 11A.

Example 12B

N-({5-[(benzoylamino)methyl]thien-2-yl}sulfonyl)-4-{4-[(4'-chloro-1,1'-biphenyl-2-yl)methyl]piperazin-1-yl}benzamide This EXAMPLE was prepared by substituting EXAMPLE 4D for EXAMPLE 1H and EXAMPLE 12A for EXAMPLE 1E in EXAMPLE 1I, except here the purification was done as in EXAMPLE 11B. $^1$H NMR (300 MHz, DMSO-$d_6$) δ 12.20 (v br s, 1H), 9.60 (v br s, 1H), 9.26 (t, 1H), 7.87 (d, 2H), 7.79 (m, 3H), 7.67 (d, 1H), 7.51 (m, 7H), 7.40 (d, 2H), 7.36 (m, 1H), 7.09 (d, 1H), 6.90 (d, 2H), 4.64 (d, 2H), 4.38 (br s, 1H), 3.85 (br s, 1H), 3.40-2.80 (envelope, 8H).

Example 13

4-{4-[(4'-chloro-1,1'-biphenyl-2-yl)methyl]piperazin-1-yl}-N-[(6-chloroimidazo[2,1-b][1,3]thiazol-5-yl)sulfonyl]benzamide This EXAMPLE was prepared by substituting EXAMPLE 4D for EXAMPLE 1H and 6-chloroimidazo[2,1-b]thiazole-5-sulfonamide for EXAMPLE 1E in EXAMPLE 1I, except here the purification was done as in EXAMPLE 11B. $^1$H NMR (300 MHz, DMSO-$d_6$) δ 9.60 (v br s, 1H), 8.04 (d, 1H), 7.79 (m, 3H), 7.63 (d, 1H), 7.51 (m, 4H), 7.40 (d, 2H), 7.36 (m, 1H), 6.92 (d, 2H), 4.38 (br s, 1H), 3.85 (br s, 1H), 3.40-2.80 (envelope, 8H).

Example 14

4-{4-[(4'-chloro-1,1'-biphenyl-2-yl)methyl]piperazin-1-yl}-N-(morpholin-4-ylsulfonyl)benzamide This EXAMPLE was prepared by substituting EXAMPLE 4D for EXAMPLE 1H and morpholine-4-sulfonamide for EXAMPLE 1E in EXAMPLE 1I, except here the purification was done as in EXAMPLE 11B. $^1$H NMR (300 MHz, DMSO-$d_6$) δ 11.58 (br s, 1H), 9.60 (v br s, 1H), 7.82 (d, 2H), 7.75 (br s, 1H), 7.55 (m, 4H), 7.40 (d, 2H), 7.36 (m, 1H), 6.96 (d, 2H), 4.38 (br s, 1H), 3.85 (br s, 1H), 3.61 (m, 4H), 3.40-2.80 (envelope, 8H), 3.25 (m, 4H).

Example 15

4-{4-[(4'-chloro-1,1'-biphenyl-2-yl)methyl]piperazin-1-yl}-N-[(2,4-dimethyl-1,3-thiazol-5-yl)sulfonyl]benzamide This EXAMPLE was prepared by substituting EXAMPLE 4D for EXAMPLE 1H and 2,4-dimethylthiazole-5-sulfonamide for EXAMPLE 1E in EXAMPLE 1I, except here the purification was done as in EXAMPLE 11B. $^1$H NMR (300 MHz, DMSO-$d_6$) δ 12.40 (v br s, 1H), 9.60 (v br s, 1H), 7.80 (d, 2H), 7.75 (br s, 1H), 7.55 (m, 4H), 7.40 (d, 2H), 7.36 (m, 1H), 6.94 (d, 2H), 4.38 (br s, 1H), 3.85 (br s, 1H), 3.40-2.80 (envelope, 8H), 2.65 (s, 3H), 2.55 (s, 3H).

Example 16

4-{4-[(4'-chloro-1,1'-biphenyl-2-yl)methyl]piperazin-1-yl}-N-{[4-phenyl-5-(trifluoromethyl)thien-3-yl]sulfonyl}benzamide

Example 16A 4-phenyl-5-(trifluoromethyl)thiophene-3-sulfonamide

This EXAMPLE was prepared by substituting 4-phenyl-5-(trifluoromethyl)thiophene-3-sulfonyl chloride for 2-acetamido-4-methylthiazole-5-sulfonyl chloride in EXAMPLE 11A.

Example 16B

4-{4-[(4'-chloro-1,1'-biphenyl-2-yl)methyl]piperazin-1-yl}-N-{[4-phenyl-5-(trifluoromethyl)thien-3-yl]sulfonyl}benzamide This EXAMPLE was prepared by substituting EXAMPLE 4D for EXAMPLE 1H and EXAMPLE 16A for EXAMPLE 1E in EXAMPLE 1I, except here the purification was done as in EXAMPLE 11B. $^1$H NMR (300 MHz, DMSO-$d_6$) δ 11.85 (v br s, 1H), 9.60 (v br s, 1H), 8.80 (s, 1H), 7.77 (br s, 1H), 7.60 (d, 2H), 7.53 (m, 4H), 7.40 (m, 3H), 7.35 (m, 3H), 7.16 (d, 2H), 6.89 (d, 2H), 4.38 (br s, 1H), 3.85 (br s, 1H), 3.40-2.80 (envelope, 8H).

Example 17

4-{4-[(4'-chloro-1,1'-biphenyl-2-yl)methyl]piperazin-1-yl}-N-[(5-fluoro-3-methyl-1-benzothien-2-yl)sulfonyl]benzamide

Example 17A 5-fluoro-3-methylbenzo[b]thiophene-2-sulfonamide

This EXAMPLE was prepared by substituting 5-fluoro-3-methylbenzo[b]thiophene-2-sulfonyl chloride for 2-acetamido-4-methylthiazole-5-sulfonyl chloride in EXAMPLE 11A.

Example 17B

4-{4-[(4'-chloro-1,1'-biphenyl-2-yl)methyl]piperazin-1-yl}-N-[(5-fluoro-3-methyl-1-benzothien-2-yl)sulfonyl]benzamide This EXAMPLE was prepared by substituting EXAMPLE 4D for EXAMPLE 1H and EXAMPLE 17A for EXAMPLE 1E in EXAMPLE 1I, except here the purification was done as in EXAMPLE 11B. $^1$H NMR (300 MHz, DMSO-$d_6$) δ 12.60 (v br s, 1H), 9.60 (v br s, 1H), 8.12 (dd, 1H), 7.85 (d, 1H) 7.80 (m, 3H), 7.52 (m, 4H), 7.46 (dd, 1H), 7.40 (d, 2H), 7.36 (m, 1H), 6.92 (d, 2H), 4.38 (br s, 1H), 3.85 (br s, 1H), 3.40-2.80 (envelope, 8H), 2.66 (s, 3H).

Example 18

N-(1,3-benzothiazol-2-ylsulfonyl)-4-{4-[(4'-chloro-1,1'-biphenyl-2-yl)methyl]piperazin-1-yl}benzamide

Example 18A benzo[d]thiazole-2-sulfonamide

Benzo[d]thiazole-2-sulfonamide was prepared as described by Roblin, Jr, R. O.; Clapp, J. W., *J. Am. Chem. Soc.* 1950, 72, 4890-4892.

Example 18B

N-(1,3-benzothiazol-2-ylsulfonyl)-4-{4-[(4'-chloro-1,1'-biphenyl-2-yl)methyl]piperazin-1-yl}benzamide This EXAMPLE was prepared by substituting EXAMPLE 4D for EXAMPLE 1H and EXAMPLE 18A for EXAMPLE 1E in EXAMPLE 1I, except here the purification was done as in EXAMPLE 11B. $^1$H NMR (500 MHz, DMSO-$d_6$) δ 11.79 (br s, 1H), 8.17 (d, 1H), 8.03 (d, 1H), 7.78 (d, 2H), 7.74 (br s, 1H), 7.55 (m, 6H), 7.40 (d, 2H), 7.34 (d, 1H), 6.87 (d, 2H), 4.36 (m, 2H), 3.80 (m, 2H), 3.42 (m, 2H), 3.05 (m, 2H), 2.90 (m, 2H).

Example 19

4-{4-[(4'-chloro-1,1'-biphenyl-2-yl)methyl]piperazin-1-yl}-N-(thien-2-ylsulfonyl)benzamide This EXAMPLE was prepared by substituting EXAMPLE 4D for EXAMPLE 1H and thiophene-2-sulfonamide for EXAMPLE 1E in EXAMPLE 1I, except here the purification was done as in EXAMPLE 11B. $^1$H NMR (500 MHz, DMSO-$d_6$) δ 12.33 (br s, 1H), 8.02 (dd, 1H), 7.82 (dd, 1H), 7.78 (d, 2H), 7.75 (br s, 1H), 7.54 (m, 4H), 7.39 (d, 2H), 7.34 (m, 1H), 7.20 (dd, 1H), 6.94 (d, 2H), 4.33 (m, 2H), 3.89 (m, 2H), 3.25 (m, 2H), 3.12 (m, 2H), 2.91 (m, 2H).

Example 20

4-{4-[(4'-chloro-1,1'-biphenyl-2-yl)methyl]piperazin-1-yl}-N-[(5,7-dimethyl[1,2,4]triazolo[1,5-a]pyrimidin-2-yl)sulfonyl]benzamide

Example 20A 5,7-dimethyl-[1,2,4]triazolo[1,5-a]pyrimidine-2-sulfonamide

This EXAMPLE was prepared by substituting 5,7-dimethyl-[1,2,4]triazolo[1,5-a]pyrimidine-2-sulfonyl chloride for 2-acetamido-4-methylthiazole-5-sulfonyl chloride in EXAMPLE 11A.

Example 20B

4-{4-[(4'-chloro-1,1'-biphenyl-2-yl)methyl]piperazin-1-yl}-N-[(5,7-dimethyl[1,2,4]triazolo[1,5-a]pyrimidin-2-yl)sulfonyl]benzamide This EXAMPLE was prepared by substituting EXAMPLE 4D for EXAMPLE 1H and EXAMPLE 20A for EXAMPLE 1E in EXAMPLE 1I, except here the purification was done as in EXAMPLE 11B. $^1$H NMR (300 MHz, DMSO-$d_6$) δ 9.60 (v br s, 1H), 7.81 (d, 2H), 7.75 (br s, 1H), 7.55 (m, 4H), 7.40 (d, 2H), 7.39 (s, 1H), 7.36 (m, 1H), 6.94 (d, 2H), 4.38 (br s, 1H), 3.85 (br s, 1H), 3.40-2.80 (envelope, 8H), 2.78 (s, 3H), 2.62 (s, 3H).

Example 21 ethyl 4-{[(4-{4-[(4'-chloro-1,1'-biphenyl-2-yl)methyl]piperazin-1-yl}benzoyl)amino]sulfonyl}-5-methyl-1,2-diphenyl-1H-pyrrole-3-carboxylate

Example 21A ethyl 5-methyl-1,2-diphenyl-4-sulfamoyl-1H-pyrrole-3-carboxylate This EXAMPLE was prepared by substituting methyl 5-(chlorosulfonyl)-1-methyl-1H-pyrrole-2-carboxylate for 2-acetamido-4-methylthiazole-5-sulfonyl chloride in EXAMPLE 11A.

Example 21B ethyl 4-{[(4-{4-[(4'-chloro-1,1'-biphenyl-2-yl)methyl]piperazin-1-yl}benzoyl)amino]sulfonyl}-5-methyl-1,2-diphenyl-1H-pyrrole-3-carboxylate This EXAMPLE was prepared by substituting EXAMPLE 4D for EXAMPLE 1H and EXAMPLE 21A for EXAMPLE 1E in EXAMPLE 1I, except here the purification was done as in EXAMPLE 11B. $^1$H NMR (300 MHz, DMSO-$d_6$) δ 11.70 (br s, 1H), 9.60 (v br s, 1H), 7.90 (d, 2H), 7.77 (br s, 1H), 7.53 (m, 4H), 7.40 (m, 6H), 7.27 (m, 2H), 7.20 (m, 3H), 7.09 (m, 2H), 6.92 (d, 2H), 4.38 (br s, 1H), 4.00 (q, 2H), 3.85 (br s, 1H), 3.40-2.80 (envelope, 8H), 2.35 (s, 3H), 0.90 (t, 3H).

Example 22 methyl 5-{[(4-{4-[(4'-chloro-1,1'-biphenyl-2-yl)methyl]piperazin-1-yl}benzoyl)amino]sulfonyl}-1-methyl-1H-pyrrole-2-carboxylate

Example 22A methyl 1-methyl-5-sulfamoyl-1H-pyrrole-2-carboxylate

This EXAMPLE was prepared by substituting methyl 5-(chlorosulfonyl)-1-methyl-1H-pyrrole-2-carboxylate for 2-acetamido-4-methylthiazole-5-sulfonyl chloride in EXAMPLE 11A.

Example 22B methyl 5-{[(4-{4-[(4'-chloro-1,1'-biphenyl-2-yl)methyl]piperazin-1-yl}benzoyl)amino]sulfonyl}-1-methyl-1H-pyrrole-2-carboxylate This EXAMPLE was prepared by substituting EXAMPLE 4D for EXAMPLE 1H and EXAMPLE 22A for EXAMPLE 1E in EXAMPLE 1I, except here the purification was done as in EXAMPLE 11B. $^1$H NMR (300 MHz, DMSO-$d_6$) δ 11.90 (br s, 1H), 9.60 (v br s, 1H), 7.85 (d, 1H), 7.78 (m, 3H), 7.55 (m, 4H), 7.40 (d, 2H), 7.36 (m, 1H), 7.15 (d, 1H), 7.92 (d, 2H), 4.38 (br s, 1H), 3.90 (s, 3H), 3.85 (br s, 1H), 3.78 (s, 3H), 3.40-2.80 (envelope, 8H).

Example 23

4-{4-[(4'-chloro-1,1'-biphenyl-2-yl)methyl]piperazin-1-yl}-N-{[5-(1,3-dimethyl-1H-pyrazol-5-yl)isoxazol-4-yl]sulfonyl}benzamide

Example 23A 5-(1,3-dimethyl-1H-pyrazol-5-yl)isoxazole-4-sulfonamide

This EXAMPLE was prepared by substituting 5-(1,3-dimethyl-1H-pyrazol-4-yl)isoxazole-4-sulfonyl chloride for 2-acetamido-4-methylthiazole-5-sulfonyl chloride in EXAMPLE 11A.

Example 23B

4-{4-[(4'-chloro-1,1'-biphenyl-2-yl)methyl]piperazin-1-yl}-N-{[5-(1,3-dimethyl-1H-pyrazol-5-yl)isoxazol-4-yl]sulfonyl}benzamide This EXAMPLE was prepared by substituting EXAMPLE 4D for EXAMPLE 1H and EXAMPLE 23A for EXAMPLE 1E in EXAMPLE 1I, except here the purification was done as in EXAMPLE 11B. $^1$H NMR (300 MHz, DMSO-$d_6$) δ 11.90 (br s, 1H), 9.60 (v br s, 1H), 8.90 (s, 1H), 8.56 (s, 1H), 7.78 (m, 3H), 7.55 (m, 4H), 7.40 (d, 2H), 7.36 (m, 1H), 7.92 (d, 2H), 4.38 (br s, 1H), 3.85 (br s, 1H), 3.83 (s, 3H), 3.40-2.80 (envelope, 8H), 2.37 (s, 3H).

Example 24

4-{4-[(4'-chloro-1,1'-biphenyl-2-yl)methyl]piperazin-1-yl}-N-[(4-chloro-3-methylisothiazol-5-yl)sulfonyl]benzamide This EXAMPLE was prepared by substituting 4-chloro-3-methyl-isothiazole-5-sulfonamide for EXAMPLE 1E and EXAMPLE 4D for EXAMPLE 1H in EXAMPLE 1I. $^1$H NMR (300 MHz, DMSO-$d_6$) δ 2.36 (s, 3H), 2.87-3.10 (m, 4H), 3.71-3.90 (m, 4H), 4.33-4.50 (m, 2H), 6.81-6.91 (m, 2H), 7.35-7.46 (m, 3H), 7.47-7.63 (m, 4H), 7.72-7.84 (m, 3H), 9.45 (s, 1H).

Example 25

N-[(5-bromo-3-methyl-1-benzothien-2-yl)sulfonyl]-4-{4-[(4'-chloro-1,1'-biphenyl-2-yl)methyl]piperazin-1-yl}benzamide This EXAMPLE was prepared by substituting EXAMPLE 4D for EXAMPLE 1H and 5-bromo-3-methylbenzo[b]thiophene-2-sulfonamide for EXAMPLE 1E in EXAMPLE 1I, except here the purification was done as in EXAMPLE 11B. $^1$H NMR (300 MHz, DMSO-$d_6$) δ 12.60 (v br s, 1H), 9.60 (v br s, 1H), 8.19 (d, 1H), 8.05 (d, 1H), 7.80 (m, 3H), 7.70 (dd, 1H), 7.52 (m, 4H), 7.40 (d, 2H), 7.36 (m, 1H), 6.92 (d, 2H), 4.38 (br s, 1H), 3.85 (br s, 1H), 3.40-2.80 (envelope, 8H), 2.66 (s, 3H).

Example 26

4-{4-[(4'-chloro-1,1'-biphenyl-2-yl)methyl]piperazin-1-yl}-N-({5-[(E)-2-(1,2,4-oxadiazol-3-yl)vinyl]thien-2-yl}sulfonyl)benzamide This EXAMPLE was prepared by substituting 5-(2-[1,2,4]oxadiazol-3-yl-vinyl)-thiophene-2-sulfonamide for EXAMPLE 1E and EXAMPLE 4D for EXAMPLE 1H in EXAMPLE 1I. $^1$H NMR (300 MHz, DMSO-$d_6$) δ 2.73-2.99 (m, 2H), 3.00-3.22 (m, 2H), 3.73-4.03 (m, 4H), 4.23-4.49 (m, 2H), 6.89-6.99 (m, 2H), 7.26-7.45 (m, 4H), 7.48-7.58 (m, 4H), 7.61 (d, 1H), 7.71-7.83 (m, 5H), 7.83-7.92 (m, 1H), 9.62 (s, 1H).

Example 27

4-{4-[(4'-chloro-1,1'-biphenyl-2-yl)methyl]piperazin-1-yl}-N-{[1-(2-chloroethyl)-3,5-dimethyl-1H-pyrazol-4-yl]sulfonyl}benzamide This EXAMPLE was prepared by substituting 1-(2-chloroethyl)-3,5-dimethyl-1H-pyrazole-4-sulfonamide for EXAMPLE 1E and EXAMPLE 4D for EXAMPLE 1H in EXAMPLE 1I. $^1$H NMR (300 MHz, DMSO-D6) δ 2.02-2.09 (m, 3H), 2.29-2.35 (m, 3H), 2.77-2.97 (m, 2H), 2.98-3.17 (m, 2H), 3.81-4.00 (m, 6H), 4.28-4.45 (m, 4H), 6.86-6.99 (m, 2H), 7.32-7.44 (m, 3H), 7.48-7.60 (m, 4H), 7.71-7.82 (m, 3H), 9.52 (s, 1H), 12.01 (s, 1H).

Example 28

5-{[(4-{4-[(4'-chloro-1,1'-biphenyl-2-yl)methyl]piperazin-1-yl}benzoyl)amino]sulfonyl}-N-(1-ethylpropyl)-1,3,4-thiadiazole-2-carboxamide This EXAMPLE was prepared by substituting 5-(1-ethylpropylcarbamoyl)-[1,3,4]thiadiazole-2-sulfonamide for EXAMPLE 1E and EXAMPLE 4D for EXAMPLE 1H in EXAMPLE 1I. $^1$H NMR (300 MHz, DMSO-$d_6$) δ 0.80 (t, 6H), 1.36-1.71 (m, 4H), 2.37-2.45 (m, 1H), 2.84-3.11 (m, 4H), 3.44-3.56 (m, 2H), 3.71-3.92 (m, 2H), 4.30-4.46 (m, 2H), 6.80-6.95 (m, 2H), 7.29-7.44 (m, 3H), 7.47-7.65 (m, 4H), 7.69-7.89 (m, 3H), 9.45 (s, 1H), 12.59-12.83 (m, 1H).

Example 29

4-{4-[(4'-chloro-1,1'-biphenyl-2-yl)methyl]piperazin-1-yl}-N-[(5-chloro-1,3-dimethyl-1H-pyrazol-4-yl)sulfonyl]benzamide This EXAMPLE was prepared by substituting 5-chloro-1,3-dimethyl-1H-pyrazole-4-sulfonamide for EXAMPLE 1E and EXAMPLE 4D for EXAMPLE 1H in EXAMPLE 1I. $^1$H NMR (300 MHz, DMSO-$d_6$) δ 2.36 (s, 3H), 2.79-2.98 (m, 2H), 3.00-3.19 (m, 2H), 3.51-3.59 (m, 2H), 3.77 (s, 3H), 3.84-4.03 (m, 2H), 4.28-4.56 (m, 2H), 6.86-7.02 (m, 2H), 7.30-7.45 (m, 3H), 7.48-7.64 (m, 4H), 7.71-7.88 (m, 3H), 9.53 (s, 1H).

Example 30

4-{4-[(4'-chloro-1,1'-biphenyl-2-yl)methyl]piperazin-1-yl}-N-[(4-nitro-5-piperidin-1-ylthien-2-yl)sulfonyl]benzamide

Example 30A 4-nitro-5-(piperidin-1-yl)thiophene-2-sulfonamide

This EXAMPLE was prepared by substituting piperidine for EXAMPLE 1D in EXAMPLE 1E.

Example 30B

4-{4-[(4'-chloro-1,1'-biphenyl-2-yl)methyl]piperazin-1-yl}-N-[(4-nitro-5-piperidin-1-ylthien-2-yl)sulfonyl]benzamide This EXAMPLE was prepared by substituting EXAMPLE 4D for EXAMPLE 1H and EXAMPLE 30A for EXAMPLE 1E in EXAMPLE 1I, except here the purification was done as in EXAMPLE 11B. $^1$H NMR (500 MHz, DMSO-$d_6$) δ 11.79 (br s, 1H), 7.93 (s, 1H), 7.80 (d, 2H), 7.74 (m, 1H), 7.52 (m, 4H), 7.39 (d, 2H), 7.34 (m, 1H), 6.94 (d, 2H), 4.25 (m, 2H), 3.56 (m, 4H), 3.35 (m, 4H), 3.25 (m, 2H), 2.91 (m, 2H), 1.7 (m, 4H), 1.61 (m, 2H).

Example 31

4-{4-[(4'-chloro-1,1'-biphenyl-2-yl)methyl]piperazin-1-yl}-N-[(5-isoxazol-5-yl-2-furyl)sulfonyl]benzamide

Example 31A 5-(isoxazol-5-yl)furan-2-sulfonamide

This EXAMPLE was prepared by substituting 5-(isoxazol-5-yl)furan-2-sulfonyl chloride for 2-acetamido-4-methylthiazole-5-sulfonyl chloride in EXAMPLE 11A.

Example 31B

4-{4-[(4'-chloro-1,1'-biphenyl-2-yl)methyl]piperazin-1-yl}-N-[(5-isoxazol-5-yl-2-furyl)sulfonyl]benzamide This EXAMPLE was prepared by substituting EXAMPLE 4D for EXAMPLE 1H and EXAMPLE 31A for EXAMPLE 1E in EXAMPLE 1I, except here the purification was done as in EXAMPLE 11B. $^1$H NMR (300 MHz, DMSO-$d_6$) δ 9.60 (v br s, 1H), 8.76 (d, 1H), 7.80 (d, 2H), 7.75 (m, 1H), 7.55 (m, 4H), 7.40 (d, 2H), 7.42 (br s, 1H), 7.36 (m, 2H), 7.96 (d, 1H), 7.92 (d, 2H), 4.38 (br s, 1H), 3.85 (br s, 1H), 3.40-2.80 (envelope, 8H).

Example 32

4-{4-[(4'-chloro-1,1'-biphenyl-2-yl)methyl]piperazin-1-yl}-N-[(3,5-dimethylisoxazol-4-yl)sulfonyl]benzamide This EXAMPLE was prepared by substituting EXAMPLE 4D for EXAMPLE 1H and 3,5-dimethylisoxazole-4-sulfonamide for EXAMPLE 1E in EXAMPLE 1I, except here the purification was done as in EXAMPLE 11B. $^1$H NMR (500

MHz, DMSO-d$_6$) δ 12.33 (br s, 1H), 7.80 (d, 2H), 7.74 (m, 1H), 7.53 (m, 4H), 7.40 (m, 2H), 7.34 (m, 1H), 6.94 (d, 2H), 4.27 (m, 2H), 3.84 (m, 2H), 3.55 (m, 2H), 3.25 (m, 2H), 2.96 (m, 2H), 2.68 (s, 3H), 2.38 (s, 3H).

Example 33

4-(4-{[2-(4-chlorophenyl)-4,4-dimethylcyclohex-1-en-1-yl]methyl}piperazin-1-yl)-2-(1H-indol-5-yloxy)-N-({4-nitro-5-[(3-pyrrolidin-1-ylpropyl)amino]thien-2-yl}sulfonyl)benzamide

Example 33A ethyl 2-(1H-indol-5-yloxy)-4-fluorobenzoate

Ethyl 2,4-difluorobenzoate (12.75 g), K$_3$PO$_4$ (14.54 g) and 5-hydroxyindole (9.12 g) were stirred at 110° C. in diglyme (125 mL) for 24 hours. The reaction was cooled and poured into ether. The solution was washed three times with 1M NaOH solution, and brine, and dried. The solution was then concentrated, and the crude product was poured into hexanes, stirred, and filtered to give the product.

Example 33B methyl 4,4-dimethyl-2-(trifluoromethylsulfonyloxy)cyclohex-1-enecarboxylate To a suspension of hexane washed NaH (17 g) in dichloromethane (700 mL), 5,5-dimethyl-2-methoxycarbonylcyclohexanone (38.5 g) was added dropwise at 0° C. After stirring for 30 minutes, the mixture was cooled to −78° C. and trifluoromethanesulfonic anhydride (40 mL) was added. The reaction mixture was warmed to room temperature and stirred for 24 hours. The organic layer was washed with brine, dried, and condensed to give the product.

Example 33C methyl 2-(4-chlorophenyl)-4,4-dimethylcyclohex-1-enecarboxylate

EXAMPLE 33B (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concentrated. Ether (4×200 mL) was added and the mixture was filtered. The combined ether solution was condensed to give the product.

Example 33D (2-(4-chlorophenyl)-4,4-dimethylcyclohex-1-enyl)methanol

To a mixture of LiBH$_4$ (13 g), EXAMPLE 33C (53.8 g) and ether (400 mL), methanol (25 mL) was added slowly by syringe. The mixture was stirred at room temperature for 24 hours. The reaction was quenched with 1N HCl with ice-cooling. The mixture was diluted with water and extracted by ether (3×100 mL). The extracts were dried, and condensed. The crude product was chromatographed on silica gel with 0-30% ethyl acetate/hexanes.

Example 33E tert-butyl 4-((2-(4-chlorophenyl)-4,4-dimethylcyclohex-1-enyl)methyl)piperazine-1-carboxylate Mesyl chloride (3.11 mL) was added via syringe to EXAMPLE 33D (10.0 g) and TEA (12.2 mL) in CH$_2$Cl$_2$ (300 mL) at 0° C., and the mixture was stirred for one minute. N-t-butoxycarbonylpiperazine (8.17 g) was added and the reaction was stirred at room temperature for 24 hours. The suspension was washed with brine, dried, and condensed. The crude product was chromatographed on silica gel with 10-20% ethyl acetate/hexanes.

Example 33F 1-((2-(4-chlorophenyl)-4,4-dimethylcyclohex-1-enyl)methyl)piperazine EXAMPLE 33E (2.0 g) and triethylsilane (0.3 mL) were stirred in 40 mL trifluoroacetic acid for one hour. The solution was concentrated and taken up in Na$_2$CO$_3$ solution, and the resulting mixture was extracted twice with CH$_2$Cl$_2$. The combined extracts were washed with brine, dried, and concentrated.

Example 33G ethyl 2-(1H-indol-5-yloxy)-4-(4-((2-(4-chlorophenyl)-4,4-dimethylcyclohex-1-enyl)methyl)piperazin-1-yl)benzoate EXAMPLE 33A (225 mg), EXAMPLE 33F (240 mg), and HK$_2$PO$_4$ (131 mg) were stirred in dimethylsulfoxide (4 mL) at 135° C. for 24 hours. The reaction was diluted with ethyl acetate, washed three times with water, washed with brine, dried, and concentrated. The crude product was chromatographed on silica gel with 30% ethyl acetate/hexanes.

Example 33H 2-(1H-indol-5-yloxy)-4-(4-((2-(4-chlorophenyl)-4,4-dimethylcyclohex-1-enyl)methyl)piperazin-1-yl)benzoic acid This EXAMPLE was prepared by substituting EXAMPLE 33G for EXAMPLE 1G in EXAMPLE 1H.

Example 33I 4-nitro-5-(3-(pyrrolidin-1-yl)propylamino)thiophene-2-sulfonamide This EXAMPLE was prepared by substituting 1-(3-aminopropyl)pyrrolidine for EXAMPLE 1D in EXAMPLE 1E.

Example 33J 4-(4-{[2-(4-chlorophenyl)-4,4-dimethylcyclohex-1-en-1-yl]methyl}piperazin-1-yl)-2-(1H-indol-5-yloxy)-N-({4-nitro-5[(3-pyrrolidin-1-ylpropyl)amino]thien-2-yl}sulfonyl)benzamide This EXAMPLE was prepared by substituting EXAMPLE 33I for EXAMPLE 1E and EXAMPLE 33H for EXAMPLE 1H in EXAMPLE 1I. ¹H NMR (400 MHz, DMSO-d₆) δ 11.12 (s, 1H), 9.50 (bs, 1H), 9.28 (t, 1H), 7.80 (s, 1H), 7.58 (d, 1H), 7.40-7.35 (m, 4H), 7.15 (d, 1H), 7.08 (d, 2H), 6.85 (dd, 1H), 6.71 (dd, 1H), 6.37 (t, 1H), 6.24 (d, 1H), 3.52 (m, 4H), 3.35-3.23 (m, 4H), 3.17 (m, 4H), 2.97 (m, 4H), 2.18 (t, 2H), 2.00 (m, 8H), 1.84 (m, 2H), 1.44 (t, 2H), 0.93 (s, 6H).

Example 34

4-(4-{[2-(4-chlorophenyl)-4,4-dimethylcyclohex-1-en-1-yl]methyl}piperazin-1-yl)-N-[(5-{[3-(dimethylamino)propyl]amino}-4-nitrothien-2-yl)sulfonyl]-2-(1H-indol-5-yloxy)benzamide Example 34A 5-(3-(dimethylamino)propylamino)-4-nitrothiophene-2-sulfonamide This EXAMPLE was prepared by substituting 3-(dimethylamino)-1-propylamine for EXAMPLE 1D in EXAMPLE 1E.

Example 34B 4-(4-{[2-(4-chlorophenyl)-4,4-dimethylcyclohex-1-en-1-yl]methyl}piperazin-1-yl)-N-[(5-{[3-(dimethylamino)propyl]amino}-4-nitrothien-2-yl)sulfonyl]-2-(1H-indol-5-yloxy)benzamide This EXAMPLE was prepared by substituting EXAMPLE 34A for EXAMPLE 1E and EXAMPLE 33H for EXAMPLE 1H in EXAMPLE 1I. ¹H NMR (400 MHz, DMSO-d₆) δ 10.95 (s, 1H), 9.15 (bs, 1H), 7.58 (d, 1H), 7.43 (s, 1H), 7.35-7.27 (m, 4H), 7.03 (d, 2H), 7.01 (dd, 1H), 6.74 (dd, 1H), 6.53 (dd, 1H), 6.31 (t, 1H), 6.15 (d, 1H), 2.94 (m, 6H), 2.72 (s, 2H), 2.63 (m, 6H), 2.20-2.12 (m, 8H), 1.94 (m, 4H), 1.37 (t, 2H), 0.91 (s, 6H).

Example 35

4-(4-{[2-(4-chlorophenyl)-4,4-dimethylcyclohex-1-en-1-yl]methyl}piperazin-1-yl)-2-(1H-indol-5-yloxy)-N-({5-[(3-morpholin-4-ylpropyl)amino]-4-nitrothien-2-yl}sulfonyl)benzamide Example 35A 5-(3-morpholinopropylamino)-4-nitrothiophene-2-sulfonamide This EXAMPLE was prepared by substituting 3-(4-morpholino)-1-propylamine for EXAMPLE 1D in EXAMPLE 1E.

Example 35B 4-(4-{[2-(4-chlorophenyl)-4,4-dimethylcyclohex-1-en-1-yl]methyl}piperazin-1-yl)-2-(1H-indol-5-yloxy)-N-({5-[(3-morpholin-4-ylpropyl)amino]-4-nitrothien-2-yl}sulfonyl)benzamide This EXAMPLE was prepared by substituting EXAMPLE 35A for EXAMPLE 1E and EXAMPLE 33H for EXAMPLE 1H in EXAMPLE 1I. ¹H NMR (400 MHz, DMSO-d₆) δ 11.04 (s, 1H), 9.45 (bs, 1H), 7.61 (s, 1H), 7.56 (d, 1H), 7.35-7.30 (m, 4H), 7.09 (dd, 1H), 7.04 (d, 2H), 6.80 (dd, 1H), 6.61 (dd, 1H), 6.34 (t, 1H), 6.16 (d, 1H), 3.62 (t, 4H), 3.30 (m, 2H), 3.02 (t, 4H), 2.78 (bs, 2H), 2.54 (m, 6H), 2.25 (m, 4H), 2.14 (t, 2H), 1.95 (s, 2H), 1.83 (m, 2H), 1.38 (t, 2H), 0.91 (s, 6H).

Example 36

N-{[5-({(1R)-3-(dimethylamino)-1-[(phenylthio)methyl]propyl}amino)-4-nitrothien-2-yl]sulfonyl}-4-{4-[2-(trifluoromethyl)benzylidene]piperidin-1-yl}benzamide Example 36A ethyl 4-(4-(2-(trifluoromethyl)benzylidene)piperidin-1-yl)benzoate A suspension of 2-(trifluoromethyl)benzyl triphenylphosphonium bromide (prepared according to the procedure described in J. Chem. Soc. Perkin Trans. I 1995, 18, 2293-2308) (0.737 g) in THF (10 mL) was treated with n-butyllithium (724 μL, of a 1.6M solution in hexanes) at 0° C., treated with ethyl 4-(4-oxo-1-piperidinyl)benzoate (prepared according to the procedure described in Synthesis 1981, 606-608, 0.32 g), and gradually warmed to room temperature overnight. The reaction mixture was partitioned between ethyl acetate and saturated aqueous NH₄Cl and the aqueous layer was extracted with ethyl acetate (2×). The combined organic layers were dried (MgSO₄), filtered, and concentrated. The resulting residue was purified by silica gel chromatography eluting with 10% ethyl acetate in hexanes to give the desired product.

Example 36B 4-(4-(2-(trifluoromethyl)benzylidene)piperidin-1-yl)benzoic acid

This EXAMPLE was prepared by substituting EXAMPLE 36A for EXAMPLE 1G in EXAMPLE 1H.

Example 36C

N-{[5-({(1R)-3-(dimethylamino)-1-[(phenylthio)methyl]propyl}amino)-4-nitrothien-2-yl]sulfonyl}-4-{4-[2-(trifluoromethyl)benzylidene]piperidin-1-yl}benzamide This EXAMPLE was prepared by substituting EXAMPLE 36B for EXAMPLE 1H in EXAMPLE 1I. ¹H NMR (400 MHz, DMSO-d₆) δ 9.40 (brs, 1H), 8.91 (d, 1H), 7.79 (d, 2H), 7.72 (d, 1H), 7.64 (dd, 1H), 7.46 (m, 2H), 7.35 (m, 3H), 7.26 (m, 2H), 7.17 (t, 1H), 6.88 (d, 2H), 6.49 (s, 1H), 3.60 (m, 1H), 3.25-3.50 (m, 5H), 2.99 (m, 1H), 2.91 (m, 1H), 2.74 (s, 6H), 2.64 (s, 6H), 2.44 (m, 2H), 2.27 (m, 2H), 2.11 (m, 2H).

Example 37

4-{4-[(4'-chloro-1,1'-biphenyl-2-yl)methylene]piperidin-1-yl}-N-[(1,1-dioxidotetrahydrothien-3-yl)sulfonyl]benzamide Example 37A (4'-chlorobiphenyl-2-yl)methanol A mixture of 2-iodobenzyl alcohol (11.0 g), 4-chlorophenylbenzeneboronic acid (8.5 g), and [1,1'-bis(diphenylphosphino)ferrocene]dichloropalladium(II) (800 mg) in Na$_2$CO$_3$ (2M solution, 94 mL) and dioxane (300 mL) was heated to 80° C. for 24 hours. The mixture was cooled, the layers were separated, and the organic layer was condensed. The resulting residue was purified by silica gel chromatography eluting with 20% ethyl acetate in hexanes to give the desired product.

Example 37B 2-(bromomethyl)-4'-chlorobiphenyl

To a mixture of EXAMPLE 37A (7.9 g) and LiBr (3.45 g) in DMF (100 mL) at 0° C. was added PBr$_3$ (3.77 mL) and the reaction was stirred for 1 hour. The reaction was poured into water (400 mL), and the mixture was extracted with ether (3×200 mL). The combined ether layers were washed with 3× water, and brine, dried over Na$_2$SO$_4$, and condensed to give the title compound.

Example 37C

[(4'-chloro-1,1'-biphenyl-2-yl)methyl](triphenyl) phosphonium bromide

A mixture of EXAMPLE 37B (8.05 g) and triphenylphosphine (7.5 g) in xylene (100 mL) was heated to 110° C. for one hour. The reaction was cooled and filtered, and the solid washed with toluene, and vacuum-dried to give the title compound.

Example 37D ethyl 4-(1,4-dioxa-8-azaspiro[4.5]decan-8-yl)benzoate

Ethyl 4-fluorobenzoate (36.16 g, 215 mmol), 1,4-dioxa-8-azaspiro[4.5]decane (35.40 g, 247 mmol), and potassium carbonate (29.72 g, 215 mmol) were added to N,N-dimethylacetamide (500 mL) and heated to 100° C. for 16 hours. The solution was cooled, filtered, added to 2M HCl and extracted with 50% ethyl acetate (in hexanes). The organics were washed with water, brine, and dried on anhydrous sodium sulfate. The solution was concentrated and purified by flash column chromatography on silica gel with 20% ethyl acetate (in hexanes) increasing to 30% ethyl acetate (in hexanes).

Example 37E ethyl 4-(4-oxopiperidin-1-yl)benzoate

EXAMPLE 37D (16.23 g, 55.71 mmol) was dissolved in toluene (85 mL), and 1M HCl was added (85 mL). The solution was heated at 95° C. for three hours and cooled. 50% ethyl acetate (in hexanes) was added and the phases were separated. The organic phase was washed with water, then brine, and dried on anhydrous sodium sulfate. The solvent was removed and the material used without further purification.

Example 37F ethyl 4-(4-((4'-chlorobiphenyl-2-yl)methylene)piperidin-1-yl)benzoate Sodium hydride (60% in mineral oil, 1.617 g, 40.4 mmol) was added to dimethylsulfoxide (265 mL) and heated at 80° C. for 30 minutes. EXAMPLE 37C was added followed by EXAMPLE 37E while continuing to heat the solution at 80° C. Heating at 80° C. was continued for 45 minutes. The solution was cooled, added to water, and extracted with diethyl ether three times. The ether extracts were washed with water, then brine, and dried on anhydrous sodium sulfate. The solution was concentrated and purified by flash column chromatography on silica gel with 10% ethyl acetate (in hexanes) increasing to 20% ethyl acetate (in hexanes).

Example 37G 4-(4-((4'-chlorobiphenyl-2-yl)methylene)piperidin-1-yl)benzoic acid

This EXAMPLE was prepared by substituting EXAMPLE 37F for EXAMPLE 4C in EXAMPLE 4D.

Example 37H

4-{4-[(4'-chloro-1,1'-biphenyl-2-yl)methylene]piperidin-1-yl}-N-[(1,1-dioxidotetrahydrothien-3-yl) sulfonyl]benzamide This EXAMPLE was prepared by substituting tetrahydrothiophene-3-sulfonamide 1,1-dioxide for EXAMPLE 1E and EXAMPLE 37G for EXAMPLE 1H in EXAMPLE 1I. $^1$H NMR (400 MHz, DMSO-d$_6$) δ 7.79 (d, 2H), 7.48 (dt, 2H), 7.42-7.33 (m, 4H), 7.31-7.23 (m, 2H), 6.85 (d, 2H), 6.13 (s, 1H), 4.33 (m, 1H), 3.35-3.22 (m, 4H), 3.20-3.06 (m, 4H), 2.30 (m, 6H).

Example 38

4-{4-[(4'-chloro-1,1'-biphenyl-2-yl)methylene]piperidin-1-yl}-N-[(5-chloro-3-methyl-1-benzothien-2-yl)sulfonyl]benzamide This EXAMPLE was prepared by substituting 5-chloro-3-methylbenzo[b]thiophene-2-sulfonamide for EXAMPLE 1E and EXAMPLE 37G for EXAMPLE 1H in EXAMPLE 1I. $^1$H NMR (400 MHz, DMSO-d$_6$) δ 8.09 (d, 1H), 7.90 (s, 1H), 7.77 (d, 2H), 7.58-7.52 (m, 2H), 7.47 (dt, 2H), 7.41-7.33 (m, 4H), 7.28 (m, 1H), 6.91 (d, 2H), 6.13 (s, 1H), 3.42 (m, 2H), 3.26 (m, 2H), 2.62 (s, 3H), 2.28 (m, 4H).

Example 39

4-{4-[(4'-chloro-1,1'-biphenyl-2-yl)methyl]piperazin-1-yl}-N-[(5-chloro-3-methyl-1-benzothien-2-yl) sulfonyl]-2-phenoxybenzamide Example 39A ethyl 4-fluoro-2-phenoxybenzoate This EXAMPLE was prepared by substituting phenol for 5-hydroxyindole in EXAMPLE 33A.

Example 39B

4'-chlorobiphenyl-2-carbaldehyde 2-bromobenzaldehyde (25.05 mL, 40.0 g, 216 mmol) was added to toluene (550 mL) and degassed and flushed with nitrogen. 4-chlorophenylboronic acid (43.9 g, 281 mmol), degassed 2M sodium carbonate (757 mL, 1513 mmol), and tetrakis(triphenylphosphine)palladium(0) (5.00 g, 4.32 mmol) were added. The mixture was refluxed for 2.5 hours, cooled, and the phases were separated. The organic layer was extracted with 2M sodium carbonate, and the aqueous layer was back extracted with ethyl ether. The organic portions were combined, dried with brine and then anhydrous sodium sulfate. The solution was concentrated and purified by flash column chromatography on silica gel with 3% ethyl acetate (in hexanes) increasing to 10% ethyl acetate (in hexanes).

Example 39C tert-butyl 4((4'-chlorobiphenyl-2-yl)methyl)piperazine-1-carboxylate This EXAMPLE was prepared by substituting EXAMPLE 39B for EXAMPLE 7A and 1-(tert-butoxycarbonyl)piperazine for methylisopropylamine in EXAMPLE 7B.

Example 39D 1-((4'-chlorobiphenyl-2-yl)methyl)piperazine

This EXAMPLE was prepared by substituting EXAMPLE 39C for EXAMPLE 33E in EXAMPLE 33F.

Example 39E ethyl 4-(4-((4'-chlorobiphenyl-2-yl)methyl)piperazin-1-yl)-2-phenoxybenzoate This EXAMPLE was prepared by substituting EXAMPLE 39A for EXAMPLE 33A and 39D for EXAMPLE 33F in EXAMPLE 33G.

Example 39F 4-(4-((4'-chlorobiphenyl-2-yl)methyl)piperazin-1-yl)-2-phenoxybenzoic acid This EXAMPLE was prepared by substituting EXAMPLE 39E for EXAMPLE 1G in EXAMPLE 1H.

Example 39G

4-{4-[(4'-chloro-1,1'-biphenyl-2-yl)methyl]piperazin-1-yl}-N-[(5-chloro-3-methyl-1-benzothien-2-yl)sulfonyl]-2-phenoxybenzamide This EXAMPLE was prepared by substituting 5-chloro-3-methylbenzo[b]thiophene-2-sulfonamide for EXAMPLE 1E and EXAMPLE 39F for EXAMPLE 1H in EXAMPLE 1I. $^1$H NMR (400 MHz, DMSO-$d_6$) δ 8.06 (d, 1H), 7.98 (d, 1H), 7.60-7.34 (m, 9H), 7.27-7.18 (m, 3H), 6.94 (t, 1H), 6.83 (d, 2H), 6.75 (dd, 1H), 6.36 (d, 1H), 3.48 (m, 2H), 3.16 (bs, 4H), 2.54 (s, 3H), 2.43 (bs, 4H).

Example 40

2-(3-chlorophenoxy)-4-(4-{[2-(4-chlorophenyl)-4,4-dimethylcyclohex-1-en-1-yl]methyl}piperazin-1-yl)-N-[(5,7-dimethyl[1,2,4]triazolo[1,5-a]pyrimidin-2-yl)sulfonyl]benzamide Example 40A ethyl 2-(3-chlorophenoxy)-4-fluorobenzoate Ethyl 2,4-difluorobenzoate (6.0 g), $K_3PO_4$ (7.5 g) and 3-chlorophenol (4.1 g) were stirred at 110° C. in diglyme (25 mL) for 24 hours. The mixture was cooled and poured into ether. The solution was washed three times with 1M NaOH solution, and with brine, and dried. The solution was then concentrated. The concentrate was chromatographed on silica gel with 10% ethyl acetate/hexanes.

Example 40B methyl 4,4-dimethyl-2-(trifluoromethylsulfonyloxy)cyclohex-1-enecarboxylate To a suspension of hexane-washed NaH (17 g) in dichloromethane (700 mL) was added 5,5-dimethyl-2-methoxycarbonylcyclohexanone (38.5 g) dropwise at 0° C. After stirring for 30 minutes, the mixture was cooled to −78° C. and trifluoroacetic anhydride (40 mL) was added. The mixture was warmed to room temperature and stirred for 24 hours. The extract was washed with brine, dried and concentrated.

Example 40C methyl 2-(4-chlorophenyl)-4,4-dimethylcyclohex-1-enecarboxylate

EXAMPLE 40B (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concentrated. Ether was added, and the mixture was filtered and concentrated.

Example 40D (2-(4-chlorophenyl)-4,4-dimethylcyclohex-1-enyl)methanol

To a mixture of $LiBH_4$ (13 g), EXAMPLE 40C (53.8 g) and ether (400 mL), methanol (25 mL) was added slowly by syringe. The mixture was stirred at room temperature for 24 hours. The mixture was quenched with 1N HCl with ice cooling. The mixture was diluted with water and extracted by ether (3×100 mL). The extracts were dried, and concentrated. The concentrate was chromatographed on silica gel with 0-30% ethyl acetate/hexanes.

Example 40E tert-butyl 4¼2-(4-chlorophenyl)-4,4-dimethylcyclohex-1-enyl)methyl)piperazine-1-carboxylate Mesyl chloride (7.5 mL) was added via syringe to EXAMPLE 40D (29.3 g) and triethylamine (30 mL) in $CH_2Cl_2$ (500 mL) at 0° C., and the mixture was stirred for 1 minute. N-t-butoxycarbonylpiperazine (25 g) was added and the mixture was stirred at room temperature for 24 hours. The suspension was washed with brine, dried, and concentrated. The concentrate was chromatographed on silica gel with 10-20% ethyl acetate/hexanes.

Example 40F

1¼2-(4-chlorophenyl)-4,4-dimethylcyclohex-1-enyl)methyl)piperazine

EXAMPLE 40E (3.0 g) and triethylsilane (1 mL) were stirred in dichloromethane (30 mL) and trifluoroacetic acid (30 mL) for 2 hours. The mixture was concentrated, taken up in ether and concentrated again.

Example 40G ethyl 2-(3-chlorophenoxy)-4-(4-((2-(4-chlorophenyl)-4,4-dimethylcyclohex-1-enyl)methyl)piperazin-1-yl)benzoate EXAMPLE 40A (1.2 g), EXAMPLE 40F (1.4 g), and $HK_2PO_4$ (0.9 g) were stirred in DMSO (2 mL) at 130° C. for 24 hours. The mixture was diluted with ethyl acetate, washed three times with water, washed with brine, dried, and concentrated. The concentrate was chromatographed on silica gel with 20% ethyl acetate/hexanes.

Example 40H 2-(3-chlorophenoxy)-4-(4-((2-(4-chlorophenyl)-4,4-dimethylcyclohex-1-enyl)methyl)piperazin-1-yl) benzoic acid EXAMPLE 40G (400 mg) was stirred in 12 mL 5:1 dioxane/2M LiOH at 90° C. for 7 hours. The solution was cooled and concentrated. Water was added, and the pH was adjusted to 4 with 1M HCl, and extracted with ethyl acetate. The extract was washed with brine, dried ($Na_2SO_4$), and concentrated.

Example 40I 5,7-dimethyl-[1,2,4]triazolo[1,5-a]pyrimidine-2-sulfonamide 5,7-Dimethyl-[1,2,4]triazolo[1,5-a]pyrimidine-2-sulfonyl chloride (2.9 g, prepared by the method of EP142152(A2, A3)) was dissolved in THF (40 mL), cooled to 0° C., concentrated, and $NH_4OH$ was added (4.0 mL). The reaction was stirred cold for 10 minutes, then at room temperature for 30 minutes. The supernatant was decanted and the solids partitioned between water and $CHCl_3$/isopropyl alcohol (3/1). The aqueous layer was extracted twice more with $CHCl_3$/isopropyl alcohol (3/1). The combined organic layers were dried ($Na_2SO_4$), and concentrated.

Example 40J 2-(3-chlorophenoxy)-4-(4-{[2-(4-chlorophenyl)-4,4-dimethylcyclohex-1-en-1-yl]methyl}piperazin-1-yl)-N-[(5,7-dimethyl[1,2,4]triazolo[1,5-a]pyrimidin-2-yl)sulfonyl]benzamide EXAMPLE 40H (170 mg), EXAMPLE 40I (68 mg), 1-ethyl-3-(3-(dimethylamino)propyl)-carbodiimide hydrochloride (113 mg), and 4-dimethylaminopyridine (72 mg) were stirred in $CH_2Cl_2$ (3 mL) for 24 hours. After concentration and redissolving the mixture in DMSO/methanol, purification was done by preparative HPLC using a C18 column, 250×50 mm, 10μ, and eluting with a gradient of 20-100% $CH_3CN$ vs. 0.1% TFA in water. The resultant salt was neutralized by partitioning between $CH_2Cl_2$ and saturated $NaHCO_3$. $^1H$ NMR (500 MHz, DMSO-$d_6$) δ 7.82 (d, 1H), 7.38 (d, 2H), 7.20 (s, 1H), 7.13 (dd, 1H), 7.08 (d, 2H), 6.87 (d, 1H), 6.76 (dd, 1H), 6.43 (s, 1H), 6.42 (d, 1H), 6.36 (s, 1H), 3.13 (br s, 4H), 2.80 (br s, 2H), 2.68 (s, 3H), 2.59 (s, 3H), 2.25 (br s, 4H), 2.19 (br m, 2H), 1.98 (s, 2H), 1.40 (t, 2H), 0.93 (s, 6H).

Example 41

4-(4-{[2-(4-chlorophenyl)-4,4-dimethylcyclohex-1-en-1-yl]methyl}piperazin-1-yl)-N-[(5,7-dimethyl[1,2,4]triazolo[1,5-a]pyrimidin-2-yl)sulfonyl]-2-[(6-fluoro-1H-indol-5-yl)oxy]benzamide

Example 41A ethyl 4-fluoro-2-(6-fluoro-1H-indol-5-yloxy)benzoate

This EXAMPLE was prepared by substituting 6-fluoro-5-hydroxyindole (prepared by the method of WO02/12227) for 3-chlorophenol in EXAMPLE 40A.

Example 41B ethyl 4-(4-((2-(4-chlorophenyl)-4,4-dimethylcyclohex-1-enyl)methyl)piperazin-1-yl)-2-(6-fluoro-1H-indol-5-yloxy)benzoate This EXAMPLE was prepared by substituting EXAMPLE 41A for EXAMPLE 40A in EXAMPLE 40G.

Example 41C 4-(4-(2-(4-chlorophenyl)-4,4-dimethylcyclohex-1-enyl)methyl)piperazin-1-yl)-2-(6-fluoro-1H-indol-5-yloxy)benzoic acid This EXAMPLE was prepared by substituting EXAMPLE 41B for EXAMPLE 40G in EXAMPLE 40H.

Example 41D 4-(4-{[2-(4-chlorophenyl)-4,4-dimethylcyclohex-1-en-1-yl]methyl}piperazin-1-yl)-N-[(5,7-dimethyl[1,2,4]triazolo[1,5-a]pyrimidin-2-yl)sulfonyl]-2-[(6-fluoro-1H-indol-5-yl)oxy]benzamide This EXAMPLE was prepared by substituting EXAMPLE 41C for EXAMPLE 40H in EXAMPLE 40J. $^1H$ NMR (500 MHz, DMSO-$d_6$) δ 11.07 (s, 1H), 7.78 (d, 1H), 7.36 (d, 2H), 7.30 (m, 1H), 7.24 (d, 1H), 7.20 (s, 1H), 7.08 (d, 3H), 6.59 (dd, 1H), 6.30 (s, 1H), 6.05 (s, 1H), 2.95 (br s, 4H), 2.75 (br s, 2H), 2.68 (s, 3H), 2.59 (s, 3H), 2.22 (br s, 4H), 2.17 (br m, 2H), 1.95 (s, 2H), 1.40 (t, 2H), 0.93 (s, 6H).

Example 42

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-[(5,7-dimethyl[1,2,4]triazolo[1,5-a]pyrimidin-2-yl)sulfonyl]benzamide

Example 42A ethyl 2-(6,7-difluoro-1H-indol-5-yloxy)-4-fluorobenzoate

This EXAMPLE was prepared by substituting 6,7-difluoro-5-hydroxyindole (prepared by the method of WO02/12227) for 3-chlorophenol in EXAMPLE 40A.

Example 42B ethyl 4-(4-(2-(4-chlorophenyl)-4,4-dimethylcyclohex-1-enyl)methyl)piperazin-1-yl)-2-(6,7-difluoro-1H-indol-5-yloxy)benzoate This EXAMPLE was prepared by substituting EXAMPLE 42A for EXAMPLE 40A in EXAMPLE 40G.

Example 42C 4-(4-(2-(4-chlorophenyl)-4,4-dimethylcyclohex-1-enyl)methyl)piperazin-1-yl)-2-(6,7-difluoro-1H-indol-5-yloxy)benzoic acid This EXAMPLE was prepared by substituting EXAMPLE 42B for EXAMPLE 40G in EXAMPLE 40H.

Example 42D 4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-[(5,7-dimethyl[1,2,4]triazolo[1,5-a]pyrimidin-2-yl)sulfonyl]benzamide This EXAMPLE was prepared by substituting EXAMPLE 42C for EXAMPLE 40H in EXAMPLE 40J. $^1$H NMR (500 MHz, DMSO-$d_6$) δ 11.58 (s, 1H), 7.80 (d, 1H), 7.33 (d, 2H), 7.31 (s, 1H), 7.17 (s, 1H), 7.03 (d, 2H), 6.70 (d, 1H), 6.65 (dd, 1H), 6.35 (m, 1H), 6.19 (s, 1H), 3.00 (br s, 4H), 2.71 (br s, 2H), 2.68 (s, 3H), 2.59 (s, 3H), 2.20 (br s, 4H), 2.17 (br m, 2H), 1.95 (s, 2H), 1.39 (t, 2H), 0.93 (s, 6H).

Example 43 tert-butyl (2S)-2-{[(5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-4-methyl-1,3-thiazol-2-yl)oxy]methyl}morpholine-4-carboxylate

Example 43A 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 mL) was added 1M lithium hexamethyldisilazide in tetrahydrofuran (86 mL), and after 10 minutes, TIPS-Cl (triisopropylchlorosilane) (18.2 mL) was added. The mixture was stirred at room temperature for 24 hours. The reaction was diluted with ether, and the resulting solution was washed twice with water. The extracts were dried ($Na_2SO_4$), filtered, and concentrated. The crude product was chromatographed on silica gel with 10% ethyl acetate/hexanes.

Example 43B 1-(triisopropylsilyl)-1H-pyrrolo[2,3-b]pyridin-5-ol

To a mixture of EXAMPLE 43A (24.3 g) in tetrahydrofuran (500 mL) at −78° C. was added 2.5 M n-butyllithium (30.3 mL). After 2 minutes, trimethylborate (11.5 mL) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 mL) at 0° C., and 1M aqueous NaOH (69 mL) was added, followed by 30% aqueous $H_2O_2$ (8.43 mL), and the solution was stirred for 1 hour. $Na_2S_2O_3$ (10 g) was added, and the pH was adjusted to 4-5 with concentrated HCl and solid $NaH_2PO_4$. The solution was extracted twice with ethyl acetate, and the combined extracts were washed with brine, dried ($Na_2SO_4$), filtered, and concentrated. The crude product was chromatographed on silica gel with 5-25% ethyl acetate/hexanes.

Example 43C methyl 2-(1H-pyrrolo[2,3-b]pyridin-5-yloxy)-4-fluorobenzoate

A mixture of EXAMPLE 43B (8.5 g), methyl 2,4-difluorobenzoate (7.05 g), and $K_3PO_4$ (9.32 g) in diglyme (40 mL) at 115° C. was stirred for 24 hours. The reaction was cooled, diluted with ether (600 mL), and washed twice with water, and brine, and concentrated. The crude product was chromatographed on silica gel with 2-50% ethyl acetate/hexanes.

Example 43D methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of EXAMPLE 43C (1.55 g), EXAMPLE 33F (2.42 g), and $HK_2PO_4$ (1.42 g) in dimethylsulfoxide (20 mL) at 135° C. was stirred for 24 hours. The reaction was cooled, diluted with ether (400 mL), and washed three times with 1M NaOH, and brine, and concentrated. The crude product was chromatographed on silica gel with 10-50% ethyl acetate/hexanes.

Example 43E 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic acid EXAMPLE 43D (200 mg) in dioxane (10 mL) and 1M aqueous NaOH (6 mL) at 50° C. was stirred for 24 hours. The reaction was cooled, added to $NaH_2PO_4$ solution, and extracted three times with ethyl acetate. The combined extracts were washed with brine, and concentrated to give the pure product.

Example 43F 2-chloro-4-methylthiazole-5-sulfonamide

A solution of 2-chloro-4-methylthiazole-5-sulfonyl chloride (1.0 g) in isopropyl alcohol (10 mL) was cooled with an ice-bath. Then, ammonium hydroxide (2.89 ml) was added slowly. The resulting solution was stirred at ambient temperature overnight. The solution was concentrated, the residue was mixed with water (10 mL) and extracted with ethyl acetate (2×20 mL). The crude product was purified on a silica gel column eluting with 60% ethyl acetate-hexane.

Example 43G (S)-tert-butyl 2-((4-methyl-5-sulfamoylthiazol-2-yloxy)methyl)morpholine-4-carboxylate To a solution of (S)-tert-butyl 2-(hydroxymethyl)morpholine-4-carboxylate (123 mg) in anhydrous tetrahydrofuran (5 mL) was added sodium hydride (60% dispersion with mineral oil, 94 mg). The mixture was stirred at room temperature for 30 minutes, followed by addition of EXAMPLE 43F (100 mg). The mixture was stirred at room temperature overnight. The reaction was quenched with water (15 mL) and extracted with ethyl acetate. The crude product was purified on a silica gel column eluting with 60% ethyl acetate in hexane to give the title compound.

Example 43H tert-butyl (2S)-2-{[(5-{[4-(4-{[2-(4-chlorophenyl)-4, 4-dimethylcyclohex-1-en-1-yl]methyl}piperazin-1-yl)-2-(1H-pyrrolo[2,3-b]pyridin-5-yloxy)benzoyl] sulfamoyl}-4-methyl-1,3-thiazol-2-yl)oxy] methyl}morpholine-4-carboxylate This example was prepared by substituting EXAMPLE 43E for EXAMPLE 1H and EXAMPLE 43G for EXAMPLE 1E in EXAMPLE 1I. $^1$H NMR (500 MHz, pyridine-$d_5$) δ 13.00 (s, 1H), 8.43 (d, 1H), 8.11 (d, 1H), 7.68 (d, 1H), 7.67 (t, 1H), 7.45 (d, 2H), 7.08 (d, 2H), 6.76 (dd, 1H), 6.54 (d, 1H), 6.50 (dd, 1H), 4.52-4.45 (m, 2H), 3.90-3.70 (m, 4H), 3.47 (dt, 1H), 3.07 (m, 4H), 2.98-2.84 (m, 2H), 2.77 (s, 2H), 2.76 (s, 3H), 2.26 (m, 2H), 2.14 (m, 4H), 1.97 (s, 2H), 1.52 (s, 9H), 1.39 (t, 2H), 0.94 (s, 6H).

Example 44 tert-butyl (2S)-2-{[(5-{[2-(1H-benzimidazol-4-yloxy)-4-(4-{[2-(4-chlorophenyl)-4,4-dimethylcyclohex-1-en-1-yl]methyl}piperazin-1-yl)benzoyl]sulfamoyl}-4-methyl-1,3-thiazol-2-yl)oxy] methyl}morpholine-4-carboxylate Example 44A methy 4-fluoro-2-(3-fluoro-2-nitrophenoxy)benzoate To a solution of methyl 4-fluoro-2-hydroxybenzoate (3.0 g) in tetrahydrofuran (65 ml) was added potassium t-butoxide (1.979 g) portionwise. The resulting solution was stirred at ambient temperature for 30 minutes and a solution of 1,3-difluoro-2-nitrobenzene (2.338 g) in tetrahydrofuran (15 ml) was added dropwise. After 1 hour the reaction was heated at reflux for 18 hours. The reaction was quenched with water (10 ml), diluted with brine (75 ml) and extracted with twice methylene chloride (75 ml). The crude product was isolated by concentration and purified on silica gel, and eluted with a 10, 20, 50% ethyl acetate in hexane step gradient.

Example 44B methyl 2(3-(bis(4-methoxyphenyl)methylamino)-2-nitrophenoxy)-4-fluorobenzoate To a solution of EXAMPLE 44A (3.82 g) and bis(4-methoxyphenyl)methanamine (4.51 g) in N-methyl-2-pyrrolidinone (65. ml) was added N-ethyl-N-isopropylpropan-2-amine (4.30 ml) and the mixture was heated at 100° C. for 24 hours. The crude product, isolated by concentration, was purified on silica gel, eluted with a 10, 25, 65% ethyl acetate in hexane step gradient.

Example 44C methyl 2-(2-amino-3-(bis(4-methoxyphenyl)methylamino)phenoxy)-4-fluorobenzoate To a solution of EXAMPLE 44B (2.76 g) in tetrahydrofuran (125 ml) in a stainless steel bottle was added nickel catalyst (2.76 g). The mixture was stirred for 1 hour under 30 psi of hydrogen at ambient temperature. The mixture was filtered through a nylon membrane to remove the catalyst and the title compound was obtained upon evaporation of the solvent (2.54 g).

Example 44D methyl 2-(1-(bis(4-methoxyphenyl)methyl)-1H-benzo[d]imidazol-4-yloxy)-4-fluorobenzoate To a solution EXAMPLE 44C (1.25 g) in triethyl orthoformate (30 ml) was added concentrated hydrochloric acid (0.75 ml). The mixture was stirred for 18 hours, quenched by the slow addition of 50% saturated sodium carbonate solution (100 ml) and extracted with ethyl acetate (2×100 ml). The crude product was isolated by concentration and purified on silica gel, and was eluted with a 25, 50, 70% ethyl acetate in hexane step gradient.

Example 44E methyl 2-(1-(bis(4-methoxyphenyl)methyl)-1H-benzo[d]imidazol-4-yloxy)-4-(piperazin-1-yl)benzoate A solution of EXAMPLE 44D (500 mg) and piperazine (420 mg) in dimethylsulfoxide (9 ml) was heated at 100° C. for 3 hours. The crude product was isolated by concentration and, following an aqueous work up, was purified on silica gel, and was eluted with a 5, 10% methanol in methylene chloride step gradient.

Example 44F 2-(4-chlorophenyl)-4,4-dimethylcyclohex-1-enecarbaldehyde

This example was prepared by substituting EXAMPLE 33D for EXAMPLE 8C in EXAMPLE 8D.

Example 44G methyl 2-(1-(bis(4-methoxyphenyl)methyl)-1H-benzo[d]imidazol-4-yloxy)-4-(4-((2-(4-chlorophenyl)-4,4-dimethylcyclohex-1-enyl)methyl)piperazin-1-yl)benzoate To a solution of EXAMPLE 44E (430 mg) and EXAMPLE 44F (259 mg) in dichloromethane (13 ml) was added sodium triacetoxyborohydride (323 mg) portionwise. After stirring 42 hours, the reaction was quenched slowly with saturated aqueous sodium bicarbonate solution (80 ml) and extracted with methylene chloride (2×70 ml). The crude product was isolated by concentration and purified on silica gel, and was eluted with a 0, 2, 10% methanol in methylene chloride step gradient.

Example 44H 2-(1-(bis(4-methoxyphenyl)methyl)-1H-benzo[d] imidazol-4-yloxy)-4-(4-((2-(4-chlorophenyl)-4,4-dimethylcyclohex-1-enyl)methyl)piperazin-1-yl) benzoic acid To a solution of EXAMPLE 44G (545 mg) in a mixture of methanol (7.50 ml) and tetrahydrofuran (7.50 ml) was added a solution of sodium hydroxide (269 mg) in water (3.0 ml). The reaction mixture was heated at 50° C. for 18 hours and was concentrated. The residue was mixed with water (100 ml), the pH was adjusted to ca. 7 with 1M aqueous hydrochloric acid, and the mixture was extracted with 10% methanol in methylene chloride (10×50 ml).

Example 44I

8-[4-[[2-(4-chlorophenyl)-4,4-dimethyl-1-cyclohexen-1-yl]methyl]-1-piperazinyl]-11H-benz[b]imidazo[1,5,4-ef][1,5]benzoxazepin-11-one A solution of EXAMPLE 44G (4.5 g) in anhydrous dichloromethane (100 ml) was cooled in an ice bath and catalytic N,N-dimethylformamide was added. This was followed by the dropwise addition of a solution of oxalyl dichloride (1.231 ml) in anhydrous methylene chloride (5 ml). The ice bath was removed and the reaction stirred for 1 hour. The reaction was quenched by the addition of ice (ca. 150 ml) and saturated sodium bicarbonate solution (100 ml). The mixture further diluted with saturated aqueous sodium bicarbonate solution (200 ml) and methylene chloride (200 ml). The crude product was isolated by concentration of the organic layer and the residue was purified on silica gel, eluting with a 0, 10, 25, 100% ethyl acetate in methylene chloride step gradient.

Example 44J tert-butyl (2S)-2-{[(5-{[2-(1H-benzimidazol-4-yloxy)-4-(4-{[2-(4-chlorophenyl)-4,4-dimethylcyclohex-1-en-1-yl]methyl}piperazin-1-yl)benzoyl]sulfamoyl}-4-methyl-1,3-thiazol-2-yl)oxy] methyl}morpholine-4-carboxylate To a solution of EXAMPLE 43G (35 mg) in anhydrous tetrahydrofuran (4 mL) was added 2,3,4,6,7,8,9,10-octahydropyrimido[1,2-a]azepine (19.95 µl). The mixture was stirred at room temperature for 30 minutes. EXAMPLE 44I (49.2 mg) was added and the solution was stirred overnight at room temperature. The solution was concentrated. The residue was re-dissolved in dimethylsulfoxide-methanol and was purified on a HPLC (Waters LC4000 Prep system, C18 column) using 10 mM of ammonium acetate buffered water-acetonitrile as the mobile phase. $^1$H NMR (500 MHz, pyridine-$d_5$) δ 8.55 (s, 1H), 8.00 (d, 1H), 7.53 (d, 1H), 7.44 (d, 2H), 7.27 (t, 1H), 7.22 (m, 2H), 7.07 (d, 2H), 6.73 (d, 1H), 6.71 (dd, 1H), 4.52-4.45 (m, 2H), 3.90-3.70 (m, 4H), 3.47 (dt, 1H), 3.04 (m, 4H), 2.98-2.83 (m, 2H), 2.77 (s, 2H), 2.76 (s, 3H), 2.26 (m, 2H), 2.15 (m, 4H), 1.97 (s, 2H), 1.52 (s, 9H), 1.39 (t, 2H), 0.94 (s, 6H).

Example 45

4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-pyrrolo[2,3-b]pyridin-5-yloxy)benzamide Example 45A 2-((4-fluorotetrahydro-2H-pyran-4-yl)methoxy)-4-methylthiazole-5-sulfonamide This example was prepared by substituting (4-fluorotetrahydro-2H-pyran-4-yl)methanol for (S)-tert-butyl 2-(hydroxymethyl)morpholine-4-carboxylate in EXAMPLE 43G.

Example 45B 4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-pyrrolo[2,3-b]pyridin-5-yloxy)benzamide This example was prepared by substituting EXAMPLE 43E for EXAMPLE 1H and EXAMPLE 45A for EXAMPLE 1E in EXAMPLE 1I. $^1$H NMR (500 MHz, pyridine-$d_5$) δ 13.01 (s, 1H), 8.43 (d, 1H), 8.15 (d, 1H), 7.70 (d, 1H), 7.65 (t, 1H), 7.45 (d, 2H), 7.08 (d, 2H), 6.77 (dd, 1H), 6.55 (d, 1H), 6.50 (dd, 1H), 4.52 (dd, 2H), 3.83-3.79 (m, 2H), 3.72-3.70 (m, 2H), 3.07 (m, 4H), 2.80 (s, 3H), 2.78 (s, 2H), 2.26 (m, 2H), 2.15 (m, 4H), 1.97 (s, 2H), 1.82-1.75 (m, 4H), 1.39 (t, 2H), 0.94 (s, 6H).

Example 46

2-(1H-benzimidazol-4-yloxy)-4-(4-{[2-(4-chlorophenyl)-4,4-dimethylcyclohex-1-en-1-yl] methyl}piperazin-1-yl)-N-({2-[(4-fluorotetrahydro-2H-pyran-4-yl)methoxy]-4-methyl-1,3-thiazol-5-yl}sulfonyl)benzamide This example was prepared by substituting EXAMPLE 45A for EXAMPLE 43G in EXAMPLE 44J. $^1$H NMR (500 MHz, pyridine-$d_5$) δ 8.56 (s, 1H), 8.02 (d, 1H), 7.53 (d, 1H), 7.44 (d, 2H), 7.27 (t, 1H), 7.21 (m, 2H), 7.08 (d, 2H), 6.74 (d, 1H), 6.71 (dd, 1H), 4.54 (dd, 2H), 3.84-3.79 (m, 2H), 3.73-3.70 (m, 2H), 3.05 (m, 4H), 2.79 (s, 3H), 2.78 (s, 2H), 2.26 (m, 2H), 2.16 (m, 4H), 1.98 (s, 2H), 1.82-1.75 (m, 4H), 1.39 (t, 2H), 0.94 (s, 6H).

Example 47

(S)-tert-butyl 2-((5-(N-(2-(1H-indazol-4-yloxy)-4-(4-((2-(4-chlorophenyl)-4,4-dimethylcyclohex-1-enyl) methyl)piperazin-1-yl)benzoyl)sulfamoyl)-4-methylthiazol-2-yloxy)methyl)morpholine-4-carboxylate Example 47A tert-butyl 4-hydroxy-1H-indazole-1-carboxylate and tert-butyl 4-hydroxy-2H-indazole-2-carboxylate 4-Hydroxyindazole (3.94 g) was added to tetrahydrofuran (250 mL) and the mixture was cooled to 0° C. using an ice bath. Sodium hydride (60% dispersion in mineral oil, 1.23 g)

was added, and the mixture was stirred at 0° C. for five minutes. The solution was allowed to warm to room temperature and was stirred for an additional 20 minutes. The solution was again cooled to 0° C. using an ice bath, and tert-butyldimethylchlorosilane (4.65 g) was added. The solution was allowed to warm to room temperature and stirred for 16 hours. Solvent volume was reduced under vacuum, the residue was vacuum filtered over a pad of silica gel and washed with ethyl acetate. The combined solutions were concentrated. The resulting residue was mixed with acetonitrile (200 mL), di-tert-butyl dicarbonate (7.06 g), and 4-(dimethylamino)pyridine (0.359 g). The solution was stirred at room temperature for three hours, and the solvent was removed under vacuum. To the residue was added tetrahydrofuran (200 mL) and tetrabutylammonium fluoride (1M in tetrahydrofuran, 82 mL). After stirring at room temperature for four days, the solvent was removed under vacuum, and the residue was taken up in ethyl acetate. The solution was washed with saturated aqueous ammonium chloride and brine, then dried over anhydrous sodium sulfate. The solution was filtered over silica gel, and the solvent was removed under vacuum to give the title compounds.

Example 47B

4-Fluoro-2-(1H-indazol-4-yloxy)-benzoic acid methyl ester

To a solution of EXAMPLE 47A (5.56 g) in diglyme (200 mL) was added potassium tert-butoxide (1M in tetrahydrofuran, 30.8 mL). The solution was stirred at room temperature for 15 minutes. Methyl 2,4-difluorobenzoate was added and the solution was stirred at 115° C. for 16 hours. The solution was cooled and the solvent removed under vacuum. The residue was taken up in dichloromethane (100 mL), and trifluoroacetic acid (22.6 mL) was added. The solution was stirred at room temperature for 16 hours. The solvent was removed under vacuum, the residue was taken up in ethyl acetate and washed with a saturate aqueous sodium bicarbonate solution, and the organic layer dried with anhydrous sodium sulfate. The material was purified by flash column chromatography on silica gel using 30% ethyl acetate (hexanes) increasing to 40% ethyl acetate (hexanes).

Example 47C 2-(1H-Indazol-4-yloxy)-4-piperazin-1-yl-benzoic acid methyl ester

This example was prepared by substituting EXAMPLE 47B for EXAMPLE 44D in EXAMPLE 44E.

Example 47D

4-{4-[2-(4-Chloro-phenyl)-4,4-dimethyl-cyclohex-1-enylmethyl]-piperazin-1-yl}-2-(1H-indazol-4-yloxy)-benzoic acid methyl ester This example was prepared by substituting EXAMPLE 47C for EXAMPLE 44E in EXAMPLE 44G.

Example 47E 2-(1H-indazol-4-yloxy)-4-(4-((2-(4-chlorophenyl)-4,4-dimethylcyclohex-1-enyl)methyl)piperazin-1-yl) benzoic acid This example was prepared by substituting EXAMPLE 47D for EXAMPLE 44G in EXAMPLE 44H.

Example 47F (S)-tert-butyl 2-((5-(N-(2-(1H-indazol-4-yloxy)-4-((2-(4-chlorophenyl)-4,4-dimethylcyclohex-1-enyl)methyl)piperazin-1-yl)benzoyl)sulfamoyl)-4-methylthiazol-2-yloxy)methyl)morpholine-4-carboxylate This example was prepared by substituting EXAMPLE 47E for EXAMPLE 1H and EXAMPLE 43G for EXAMPLE 1E in EXAMPLE 1I. $^1$H NMR (500 MHz, pyridine-$d_5$) δ 8.36 (s, 1H), 8.11 (d, 1H), 7.47 (d, 2H), 7.38 (d, 1H), 7.22 (m, 2H), 7.11 (d, 2H), 6.88-6.80 (m, 2H), 6.62 (d, 1H), 4.52-4.45 (m, 2H), 3.90-3.70 (m, 4H), 3.45 (dt, 1H), 3.15 (m, 4H), 2.98-2.83 (m, 2H), 2.82 (s, 2H), 2.63 (s, 3H), 2.30 (m, 2H), 2.23 (m, 4H), 1.99 (s, 2H), 1.52 (s, 9H), 1.39 (t, 2H), 0.94 (s, 6H).

Example 48

2-(1H-indazol-4-yloxy)-4-(4-((2-(4-chlorophenyl)-4,4-dimethylcyclohex-1-enyl)methyl)piperazin-1-yl)-N-(2-((4-fluorotetrahydro-2H-pyran-4-yl)methoxy)-4-methylthiazol-5-ylsulfonyl)benzamide This example was prepared by substituting EXAMPLE 47E for EXAMPLE 1H and EXAMPLE 45A for EXAMPLE 1E in EXAMPLE 1I. $^1$H NMR (500 MHz, pyridine-$d_5$) δ 8.36 (s, 1H), 8.14 (d, 1H), 7.47 (d, 2H), 7.38 (d, 1H), 7.22 (m, 2H), 7.11 (d, 2H), 6.88-6.80 (m, 2H), 6.62 (d, 1H), 4.52 (dd, 2H), 3.84-3.78 (m, 2H), 3.73-3.70 (dt, 2H), 3.15 (m, 4H), 2.82 (s, 2H), 2.67 (s, 3H), 2.30 (m, 2H), 2.23 (m, 4H), 1.99 (s, 2H), 1.82-1.75 (m, 4H), 1.41 (t, 2H), 0.96 (s, 6H).

What is claimed is:

1. A compound having Formula I

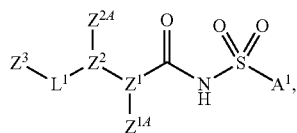

(I)

or a therapeutically acceptable salt thereof, wherein
$A^1$ is thiazolyl substituted with one or two substituents independently selected from $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(N)C(O)R^1$, $C(O)NHR^1$, $C(O)N(R^1)_2$, $C(O)NHOH$, $C(O)NHOR^1$, $C(O)NHSO_2R^1$, $NHC(O)R^1$, $NR^1C(O)R^1$, $NHC(O)OR^1$, $NR^1C(O)OR^1$, $NR^1C(O)NHR^1$, $NR^1C(O)N(R^1)_2$, $NHC(O)NH_2$, $NHC(O)NHR^1$, $NHC(O)N(R^1)_2$, $SO_2NH_2$, $SO_2NHR^1$, $SO_2N(R^1)_2$, $NHS(O)R^1$, $NHSO_2R^1$, $NR^1SO_2R^1$, $NHSO_2NHR^1$, $N(CH_3)SO_2N(CH_3)R^1$, (O), $NH_2$, $NO_2$, $N_3$, OH, F, Cl, Br, I, CN, $CF_3$, $OCF_3$, $CF_2CF_3$, $OCF_2CF_3$, $C(O)H$, $C(O)OH$, $C(N)NH_2$, $C(N)NHR^1$, $C(N)N(R^1)_2$, CNOH, $CNOCH_3$, $C(O)NH_2$ and $C(O)OR^{1A}$;
$R^1$ is $R^2$, $R^3$, $R^4$ or $R^5$;
$R^{1A}$ is cycloalkyl, cycloalkenyl or cycloalkynyl;
$R^2$ is phenyl, which is unfused or fused with benzene, heteroarene or $R^{2A}$; $R^{2A}$ is cycloalkane, cycloalkene, heterocycloalkane or heterocycloalkene;
$R^3$ is heteroaryl, which is unfused or fused with benzene, heteroarene or $R^{3A}$; $R^{3A}$ is cycloalkane, cycloalkene, heterocycloalkane or heterocycloalkene;
$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;
$R^5$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), $C(O)OH$, (O), $N_3$, CN, $NH_2$, $CF_3$, $CF_2CF_3$, F, Cl, Br or I substituents;
$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;
$R^{6A}$ and $R^{6B}$ are each independently selected alkyl;
$R^7$ is $R^8$, $R^9$, $R^{10}$ or $R^{11}$;

$R^8$ is phenyl, which is unfused or fused with benzene, heteroarene or $R^{8A}$; $R^{8A}$ is cycloalkane, cycloalkene, heterocycloalkane or heterocycloalkene;
$R^9$ is heteroaryl, which is unfused or fused with benzene, heteroarene or $R^{9A}$; $R^{9A}$ is cycloalkane, cycloalkene, heterocycloalkane or heterocycloalkene;
$R^{10}$ is cycloalkyl, cycloalkenyl, heterocycloalkyl, or heterocycloalkenyl each of which is unfused or fused with benzene, heteroarene or $R^{10A}$; $R^{10A}$ is cycloalkane, cycloalkene, heterocycloalkane or heterocycloalkene;
$R^{11}$ is alkyl, alkenyl or alkynyl, each of which is unsubstituted or substituted with one or two or three independently selected $R^{12}$, $OR^{12}$, $SR^{12}$, $S(O)R^{12}$, $SO_2R^{12}$, $C(O)R^{12}$, $C(O)OR^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;
$R^{12}$ is $R^{13}$, $R^{14}$, $R^{15}$ or $R^{16}$;
$R^{13}$ is phenyl, which is unfused or fused with benzene, heteroarene or $R^{13A}$; $R^{13A}$ is cycloalkane, cycloalkene, heterocycloalkane or heterocycloalkene;
$R^{14}$ is heteroaryl, which is unfused or fused with benzene, heteroarene or $R^{14A}$; $R^{14A}$ is cycloalkane, cycloalkene, heterocycloalkane or heterocycloalkene;
$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;
$R^{16}$ is alkyl, alkenyl or alkynyl;
$Z^1$ is $R^{26}$;
$Z^2$ is $R^{30}$;
$Z^{1A}$ and $Z^{2A}$ are both absent;
$R^{26}$ is phenylene substituted with $OR^{41}$;
$R^{30}$ is heterocycloalkylene;
$L^1$ is alkylene;
$Z^3$ is cycloalkenyl substituted with $R^{57}$;
$R^{41}$ is $R^{42}$, $R^{43}$, $R^{44}$ or $R^{45}$;
$R^{42}$ is phenyl, which is unfused or fused with benzene, heteroarene or $R^{42A}$; $R^{42A}$ is cycloalkane, cycloalkene, heterocycloalkane or heterocycloalkene;
$R^{43}$ is heteroaryl, which is unfused or fused with benzene, heteroarene or $R^{43A}$; $R^{43A}$ is cycloalkane, cycloalkene, heterocycloalkane or heterocycloalkene;
$R^{44}$ is cycloalkyl, cycloalkenyl, heterocycloalkyl, or heterocycloalkenyl, each of which is unfused or fused with benzene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $SR^{46}$, $S(O)R^{46}$, $SO_2R^{46}$, $C(O)R^{46}$, $C(O)OR^{46}$, $OC(O)R^{46}$, $OC(O)OR^{46}$, $NH_2$, $NHR^{46}$, $N(R^{46})_2$, $NHC(O)R^{46}$, $NR^{46}C(O)R^{46}$, $NHS(O)_2R^{46}$, $NR^{46}S(O)_2R^{46}$, $NHC(O)OR^{46}$, $NR^{46}C(O)OR^{46}$, $NHC(O)NH_2$, $NHC(O)NHR^{46}$, $NR^{46}C(O)N(R^{46})_2$, $C(O)NH_2$, $C(O)NHR^{46}$, $C(O)N(R^{46})_2$, $NHC(O)N(R^{46})_2$, $NR^{46}C(O)NHR^{46}$, $C(O)NHOH$, $C(O)NHOR^{46}$, $C(O)NHSO_2R^{46}$, $C(O)NR^{46}SO_2R^{46}$, $SO_2NH_2$, $SO_2NHR^{46}$, $SO_2N(R^{46})_2$, $C(O)H$, $C(O)OH$, $C(N)NH_2$, $C(N)NHR^{46}$, $C(N)N(R^{46})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{46}$ is alkyl, alkenyl, alkynyl, $R^{47}$, $R^{48}$ or $R^{49}$;

$R^{47}$ is phenyl, which is unfused or fused with benzene, heteroarene or $R^{47A}$; $R^{47A}$ is cycloalkane, cycloalkene, heterocycloalkane or heterocycloalkene;

$R^{48}$ is heteroaryl, which is unfused or fused with benzene, heteroarene or $R^{48A}$; $R^{48A}$ is cycloalkane, cycloalkene, heterocycloalkane or heterocycloalkene;

$R^{49}$ is cycloalkyl, cycloalkenyl, heterocycloalkyl, or heterocycloalkenyl, each of which is unfused or fused with benzene, heteroarene or $R^{49A}$; $R^{49A}$ is cycloalkane, cycloalkene, heterocycloalkane or heterocycloalkene;

the moieties represented by $R^{42}$, $R^{43}$, $R^{44}$, $R^{47}$, $R^{48}$, and $R^{49}$ are independently unsubstituted or substituted with one or more independently selected $R^{50}$, $OR^{50}$, $SR^{50}$, $S(O)R^{50}$, $SO_2R^{50}$, $C(O)R^{50}$, $C(O)OR^{50}$, $OC(O)R^{50}$, $OC(O)OR^{50}$, $NH_2$, $NHR^{50}$, $N(R^{50})_2$, $NHC(O)R^{50}$, $NR^{50}C(O)R^{50}$, $NHS(O)_2R^{50}$, $NR^{50}S(O)_2R^{50}$, $NHC(O)OR^{50}$, $NR^{50}C(O)OR^{50}$, $NHC(O)NH_2$, $NHC(O)NHR^{50}$, $NHC(O)N(R^{50})_2$, $NR^{50}C(O)NHR^{50}$, $NR^{50}C(O)N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{50}SO_2R^{50}$, $SO_2NH_2$, $SO_2NHR^{50}$, $SO_2N(R^{50})_2$, $C(O)H$, $C(O)OH$, $C(N)NH_2$, $C(N)NHR^{50}$, $C(N)N(R^{50})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl, which is unfused or fused with benzene, heteroarene or $R^{51A}$; $R^{51A}$ is cycloalkane, cycloalkene, heterocycloalkane or heterocycloalkene;

$R^{52}$ is heteroaryl, which is unfused or fused with benzene, heteroarene or $R^{52A}$; $R^{52A}$ is cycloalkane, cycloalkene, heterocycloalkane or heterocycloalkene;

$R^{53}$ is cycloalkyl, cycloalkenyl, heterocycloalkyl, or heterocycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $C(O)R^{55}$, $C(O)OR^{55}$, $OC(O)R^{55}$, $OC(O)OR^{55}$, $NH_2$, $NHR^{55}$, $N(R^{55})_2$, $NHC(O)R^{55}$, $NR^{55}C(O)R^{55}$, $NHS(O)_2R^{55}$, $NR^{55}S(O)_2R^{55}$, $NHC(O)OR^{55}$, $NR^{55}C(O)OR^{55}$, $NHC(O)NH_2$, $NHC(O)NHR^{55}$, $NHC(O)N(R^{55})_2$, $NR^{55}C(O)NHR^{55}$, $NR^{55}C(O)N(R^{55})_2$, $C(O)NH_2$, $C(O)NHR^{55}$, $C(O)N(R^{55})_2$, $C(O)NHOH$, $C(O)NHOR^{55}$, $C(O)NHSO_2R^{55}$, $C(O)NR^{55}SO_2R^{55}$, $SO_2NH_2$, $SO_2NHR^{55}$, $SO_2N(R^{55})_2$, $C(O)H$, $C(O)OH$, $C(N)NH_2$, $C(N)NHR^{55}$, $C(N)N(R^{55})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{55}$ is alkyl, alkenyl, alkynyl, phenyl, heteroaryl, cycloalkyl, cycloalkenyl, heterocycloalkyl, or heterocycloalkenyl;

wherein each cyclic moiety represented by $R^{1A}$, $R^2$, $R^3$, $R^4$, $R^8$, $R^9$, $R^{10}$, $R^{13}$, $R^{14}$, $R^{15}$, $R^{30}$, $R^{51}$, $R^{52}$, $R^{53}$ and $R^{55}$ is independently unsubstituted, substituted or further substituted with one or more independently selected $R^{57}$, $OR^{57}$, $SR^{57}$, $S(O)R^{57}$, $SO_2R^{57}$, $C(O)R^{57}$, $C(O)OR^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl, or alkynyl, each of which is unsubstituted or substituted with one or two or three independently selected $R^{62}$, $OR^{62}$, $SR^{62}$, $S(O)R^{62}$, $SO_2R^{62}$, $C(O)R^{62}$, $C(O)OR^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl, or alkynyl, each of which is unsubstituted or substituted with one or two or three independently selected $R^{67}$, $OR^{67}$, $SR^{67}$, $S(O)R^{67}$, $SO_2R^{67}$, $C(O)R^{67}$, $C(O)OR^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

R$^{67}$ is alkyl, alkenyl, alkynyl, phenyl, heteroaryl, cycloalkyl, cycloalkenyl, heterocycloalkyl or heterocycloalkenyl;

wherein the moieties represented by R$^{58}$, R$^{59}$, R$^{60}$, R$^{63}$, R$^{64}$, R$^{65}$, and R$^{67}$ are unsubstituted or substituted with one or more independently selected R$^{68}$, OR$^{68}$, SR$^{68}$, S(O)R$^{68}$, SO$_2$R$^{68}$, C(O)R$^{68}$, C(O)OR$^{68}$, OC(O)R$^{68}$, OC(O)OR$^{68}$, NH$_2$, NHR$^{68}$, N(R$^{68}$)$_2$, NHC(O)R$^{68}$, NR$^{68}$C(O)R$^{68}$, NHS(O)$_2$R$^{68}$, NR$^{68}$S(O)$_2$R$^{68}$, NHC(O)OR$^{68}$, NR$^{68}$C(O)OR$^{68}$, NHC(O)NH$_2$, NHC(O)NHR$^{68}$, NHC(O)N(R$^{68}$)$_2$, NR$^{68}$C(O)NHR$^{68}$, NR$^{68}$C(O)N(R$^{68}$)$_2$, C(O)NH$_2$, C(O)NHR$^{68}$, C(O)N(R$^{68}$)$_2$, C(O)NHOH, C(O)NHOR$^{68}$, C(O)NHSO$_2$R$^{68}$, C(O)NR$^{68}$SO$_2$R$^{68}$, SO$_2$NH$_2$, SO$_2$NHR$^{68}$, SO$_2$N(R$^{68}$)$_2$, C(O)H, C(O)OH, C(N)NH$_2$, C(N)NHR$^{68}$, C(N)N(R$^{68}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{68}$ is R$^{69}$, R$^{70}$, R$^{71}$ or R$^{72}$;

R$^{69}$ is phenyl, which is unfused or fused with benzene, heteroarene or R$^{69A}$; R$^{69A}$ is cycloalkane, cycloalkene, heterocycloalkane or heterocycloalkene;

R$^{70}$ is heteroaryl, which is unfused or fused with benzene, heteroarene or R$^{70A}$; R$^{70A}$ is cycloalkane, cycloalkene, heterocycloalkane or heterocycloalkene;

R$^{71}$ is cycloalkyl, cycloalkenyl, heterocycloalkyl or heterocycloalkenyl, each of which is unfused or fused with benzene, heteroarene or R$^{71A}$; R$^{71A}$ is cycloalkane, cycloalkene, heterocycloalkane or heterocycloalkene;

R$^{72}$ is alkyl, alkenyl, or alkynyl, each of which is unsubstituted or substituted with one or two or three independently selected R$^{73}$, OR$^{73}$, SR$^{73}$, S(O)R$^{73}$, SO$_2$R$^{73}$, C(O)R$^{73}$, C(O)OR$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$ R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)NH$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO$_2$NH$_2$, SO$_2$NHR$^{73}$, SO$_2$N(R$^{73}$)$_2$, C(O)H, C(O)OH, C(N)NH$_2$, C(N)NHR$^{73}$, C(N)N(R$^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{73}$ is alkyl, alkenyl, alkenyl, phenyl, heteroaryl, cycloalkyl, cycloalkenyl, heterocycloalkyl, or heterocycloalkenyl; and the moieties represented by R$^{69}$, R$^{70}$, and R$^{71}$ are unsubstituted or substituted with one or more independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, OCF$_3$, OCF$_2$CF$_3$, F, Cl, Br or I substituents.

2. The compound of claim 1 or therapeutically acceptable salt thereof,
wherein
A$^1$ is substituted with one or two substituents independently selected from R$^1$, OR$^1$, C(O)OR$^1$, NHR$^1$, N(R$^1$)$_2$, C(N)C(O)R$^1$, C(O)NHR$^1$, NHC(O)R$^1$, NR$^1$C(O)R$^1$, (O), NO$_2$, F, Cl, Br, I, and CF$_3$;

R$^1$ is R$^2$, R$^3$, R$^4$ or R$^5$;
R$^2$ is phenyl;
R$^3$ is heteroaryl;
R$^4$ is heterocycloalkyl;
R$^5$ is alkyl, or alkenyl, each of which is unsubstituted or substituted with a substituent selected from R$^7$, SR$^7$, N(R$^7$)$_2$, NHC(O)R$^7$, F, Cl, Br and I;
R$^7$ is R$^8$, R$^9$, R$^{10}$ or R$^{11}$;
R$^8$ is phenyl;
R$^9$ is heteroaryl;
R$^{10}$ is heterocycloalkyl;
R$^{11}$ is alkyl;
Z$^1$ is R$^{26}$;
Z$^2$ is R$^{30}$;
R$^{26}$ is phenylene substituted with OR$^{41}$;
R$^{30}$ is heterocycloalkylene;
L$^1$ is alkylene;
Z$^3$ is cycloalkenyl substituted with R$^{57}$;
R$^{41}$ is R$^{12}$, or R$^{43}$;
R$^{42}$ is phenyl, which is unfused or fused with heteroarene;
R$^{43}$ is heteroaryl, which is unfused or fused with heteroarene;
wherein each cyclic moiety represented by R$^2$, R$^3$, R$^4$, R$^8$, R$^9$, R$^{10}$, R$^{30}$, R$^{42}$ and R$^{43}$ is independently unsubstituted, substituted or further substituted with one or more independently selected R$^{57}$, OR$^{57}$, C(O)OR$^{57}$, F, Cl, Br or I substituents;
R$^{57}$ is R$^{58}$, or R$^{61}$;
R$^{58}$ is phenyl;
R$^{61}$ is alkyl; and
wherein R$^{58}$ is unsubstituted or substituted with one or more independently selected F, Cl, Br or I substituents.

3. A compound having formula III

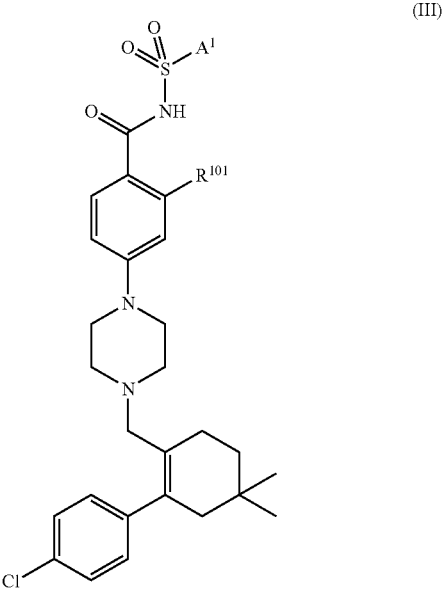

(III)

or a therapeutically acceptable salt thereof, wherein
A$^1$ is thiazolyl substituted with one or two substituents independently selected from R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(N)C(O)R$^1$, C(O)NHR$^1$, C(O)N(R$^1$)$_2$, C(O)NHOH, C(O)NHOR$^1$, C(O)NHSO$_2$R$^1$, NHC(O)R$^1$, NR$^1$C(O) R$^1$, NHC(O)OR$^1$, NR$^1$C(O)OR$^1$, NR$^1$C(O)NHR$^1$, NR$^1$C(O)N(R$^1$)$_2$, NHC(O)NH$_2$, NHC(O)NHR$^1$, NHC(O)N(R$^1$)$_2$, SO$_2$NH$_2$, SO$_2$NHR$^1$, SO$_2$N(R$^1$)$_2$, NHS(O) R$^1$, NHSO$_2$R$^1$, NR$^1$SO$_2$R$^1$, NHSO$_2$NHR$^1$, N(CH$_3$) SO$_2$N(CH$_3$)R$^1$, (O), NH$_2$, NO$_2$, N$_3$, OH, F, Cl, Br, I, CN, CF$_3$, OCF$_3$, CF$_2$CF$_3$, OCF$_2$CF$_3$, C(O)H, C(O)OH, C(N) NH$_2$, C(N)NHR$^1$, C(N)N(R$^1$)$_2$, CNOH, CNOCH$_3$, C(O)NH$_2$ and C(O)OR$^{1A}$;

R$^1$ is R$^2$, R$^3$, R$^4$ or R$^5$;
R$^{1A}$ is cycloalkyl, cycloalkenyl or cycloalkynyl;
R$^2$ is phenyl, which is unfused or fused with benzene, heteroarene or R$^{2A}$; R$^{2A}$ is cycloalkane, cycloalkene, heterocycloalkane or heterocycloalkene;

$R^3$ is heteroaryl, which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(C_{1-3})NHC(O)CH(CH_3)NH_2$, $NHC(O)CH(CH_3)NHC(O)CH(CH_3)NHR^1$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are each independently selected alkyl;

$R^7$ is $R^8$, $R^9$, $R^{10}$ or $R^{11}$;

$R^8$ is phenyl, which is unfused or fused with benzene, heteroarene or $R^{8A}$; $R^{8A}$ is cycloalkane, cycloalkene, heterocycloalkane or heterocycloalkene;

$R^9$ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl, or heterocycloalkenyl each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $SR^{12}$, $S(O)R^{12}$, $SO_2R^{12}$, $C(O)R^{12}$, $C(O)OR^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, C(O)NHOH, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, C(O)H, C(O)OH, $C(N)NH_2$, $C(N)NHR^{12}$, $C(N)N(R^{12})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$R^{101}$ is $OR^{41}$;

$R^{41}$ is $R^{42}$, $R^{43}$, $R^{44}$ or $R^{45}$;

$R^{42}$ is phenyl, which is unfused or fused with benzene, heteroarene or $R^{42A}$; $R^{42A}$ is cycloalkane, cycloalkene, heterocycloalkane or heterocycloalkene;

$R^{43}$ is heteroaryl, which is unfused or fused with benzene, heteroarene or $R^{43A}$; $R^{43A}$ is cycloalkane, cycloalkene, heterocycloalkane or heterocycloalkene;

$R^{44}$ is cycloalkyl, cycloalkenyl, heterocycloalkyl, or heterocycloalkenyl, each of which is unfused or fused with benzene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $SR^{46}$, $S(O)R^{46}$, $SO_2R^{46}$, $C(O)R^{46}$, $C(O)OR^{46}$, $OC(O)R^{46}$, $OC(O)OR^{46}$, $NH_2$, $NHR^{46}$, $N(R^{46})_2$, $NHC(O)R^{46}$, $NR^{46}C(O)R^{46}$, $NHS(O)_2R^{46}$, $NR^{46}S(O)_2R^{46}$, $NHC(O)OR^{46}$, $NR^{46}C(O)OR^{46}$, $NHC(O)NH_2$, $NHC(O)NHR^{46}$, $NHC(O)N(R^{46})_2$, $NR^{46}C(O)NHR^{46}$, $NR^{46}C(O)N(R^{46})_2$, $C(O)NH_2$, $C(O)NHR^{46}$, $C(O)N(R^{46})_2$, C(O)NHOH, $C(O)NHOR^{46}$, $C(O)NHSO_2R^{46}$, $C(O)NR^{46}SO_2R^{46}$, $SO_2NH_2$, $SO_2NHR^{46}$, $SO_2N(R^{46})_2$, C(O)H, C(O)OH, $C(N)NH_2$, $C(N)NHR^{46}$, $C(N)N(R^{46})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

K is alkyl, alkenyl, alkynyl, $R^{47}$, $R^{48}$ or $R^{49}$;

$R^{47}$ is phenyl, which is unfused or fused with benzene, heteroarene or $R^{47A}$; $R^{47A}$ is cycloalkane, cycloalkene, heterocycloalkane or heterocycloalkene;

$R^{48}$ is heteroaryl, which is unfused or fused with benzene, heteroarene or $R^{48A}$; $R^{48A}$ is cycloalkane, cycloalkene, heterocycloalkane or heterocycloalkene;

$R^{49}$ is cycloalkyl, cycloalkenyl, heterocycloalkyl, or heterocycloalkenyl, each of which is unfused or fused with benzene, heteroarene or $R^{49A}$; $R^{49A}$ is cycloalkane, cycloalkene, heterocycloalkane or heterocycloalkene;

the moieties represented by $R^{42}$, $R^{43}$, $R^{44}$, $R^{47}$, $R^{48}$, and $R^{49}$ are independently unsubstituted or substituted with one or more independently selected $R^{50}$, $OR^{50}$, $SR^{50}$, $S(O)R^{50}$, $SO_2R^{50}$, $C(O)R^{50}$, $C(O)OR^{50}$, $OC(O)R^{50}$, $OC(O)OR^{50}$, $NH_2$, $NHR^{50}$, $N(R^{50})_2$, $NHC(O)R^{50}$, $NR^{50}C(O)R^{50}$, $NHS(O)_2R^{50}$, $NR^{50}S(O)_2R^{50}$, $NHC(O)OR^{50}$, $NR^{50}C(O)OR^{50}$, $NHC(O)NH_2$, $NHC(O)NHR^{50}$, $NHC(O)N(R^{50})_2$, $NR^{50}C(O)NHR^{50}$, $NR^{50}C(O)N(R^{50})_2$, $C(O)NH_2$, $C(O)NHR^{50}$, $C(O)N(R^{50})_2$, C(O)NHOH, $C(O)NHOR^{50}$, $C(O)NHSO_2R^{50}$, $C(O)NR^{50}SO_2R^{50}$, $SO_2NH_2$, $SO_2NHR^{50}$, $SO_2N(R^{50})_2$, C(O)H, C(O)OH, $C(N)NH_2$, $C(N)NHR^{50}$, $C(N)N(R^{50})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl, which is unfused or fused with benzene, heteroarene or $R^{51A}$; $R^{51A}$ is cycloalkane, cycloalkene, heterocycloalkane or heterocycloalkene;

$R^{52}$ is heteroaryl, which is unfused or fused with benzene, heteroarene or $R^{52A}$; $R^{52A}$ is cycloalkane, cycloalkene, heterocycloalkane or heterocycloalkene;

$R^{53}$ is cycloalkyl, cycloalkenyl, heterocycloalkyl, or heterocycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $C(O)R^{55}$, $C(O)OR^{55}$, $OC(O)R^{55}$, $OC(O)OR^{55}$, $NH_2$, $NHR^{55}$, $N(R^{55})_2$, $NHC(O)R^{55}$, $NR^{55}C(O)R^{55}$, $NHS(O)_2R^{55}$, $NR^{55}S(O)_2R^{55}$, $NHC(O)OR^{55}$, $NR^{55}C(O)OR^{55}$, $NHC(O)NH_2$, $NHC(O)NHR^{55}$, $NHC(O)N(R^{55})_2$, $NR^{55}C(O)NHR^{55}$, $NR^{55}C(O)N(R^{55})_2$, $C(O)NH_2$, $C(O)NHR^{55}$, $C(O)N(R^{55})_2$, C(O)NHOH, $C(O)NHOR^{55}$, $C(O)NHSO_2R^{55}$, $C(O)NR^{55}SO_2R^{55}$, $SO_2NH_2$, $SO_2NHR^{55}$, $SO_2N(R^{55})_2$, C(O)H, C(O)OH, $C(N)NH_2$, C(N)NHR$^{55}$, C(N)N(R$^{55}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{55}$ is alkyl, alkenyl, alkynyl, phenyl, heteroaryl, cycloalkyl, cycloalkenyl, heterocycloalkyl, or heterocycloalkenyl;

wherein each cyclic moiety represented by R$^{1A}$, R$^2$, R$^3$, R$^{14}$, R$^{15}$, R$^{51}$, R$^{52}$, R$^{53}$ and R$^{55}$ is independently unsubstituted, substituted or further substituted with one or more independently selected R$^{57}$, OR$^{57}$, SR$^{57}$, S(O)R$^{57}$, SO$_2$R$^{57}$, C(O)R$^{57}$, C(O)OR$^{57}$, OC(O)R$^{57}$, OC(O)OR$^{57}$, NH$_2$, NHR$^{57}$, N(R$^{57}$)$_2$, NHC(O)R$^{57}$, NR$^{57}$C(O)R$^{57}$, NHS(O)$_2$R$^{57}$, NR$^{57}$S(O)$_2$R$^{57}$, NHC(O)OR$^{57}$, NR$^{57}$C(O)OR$^{57}$, NHC(O)NH$_2$, NHC(O)NHR$^{57}$, NHC(O)N(R$^{57}$)$_2$, NR$^{57}$C(O)NHR$^{57}$, NR$^{57}$C(O)N(R$^{57}$)$_2$, C(O)NH$_2$, C(O)NHR$^{57}$, C(O)N(R$^{57}$)$_2$, C(O)NHOH, C(O)NHOR$^{57}$, C(O)NHSO$_2$R$^{57}$, C(O)NR$^{57}$SO$_2$R$^{57}$, SO$_2$NH$_2$, SO$_2$NHR$^{57}$, SO$_2$N(R$^{57}$)$_2$, C(O)H, C(O)OH, C(N)NH$_2$, C(N)NHR$^{57}$, C(N)N(R$^{57}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{57}$ is R$^{58}$, R$^{59}$, R$^{60}$ or R$^{61}$;

R$^{58}$ is phenyl, which is unfused or fused with benzene, heteroarene or R$^{58A}$; R$^{58A}$ is cycloalkane, cycloalkene, heterocycloalkane or heterocycloalkene;

R$^{59}$ is heteroaryl, which is unfused or fused with benzene, heteroarene or R$^{59A}$; R$^{59A}$ is cycloalkane, cycloalkene, heterocycloalkane or heterocycloalkene;

R$^{60}$ is cycloalkyl, cycloalkenyl, heterocycloalkyl or heterocycloalkenyl, each of which is unfused or fused with benzene, heteroarene or R$^{60A}$; R$^{60A}$ is cycloalkane, cycloalkene, heterocycloalkane or heterocycloalkene;

R$^{61}$ is alkyl, alkenyl, or alkynyl, each of which is unsubstituted or substituted with one or two or three independently selected R$^{62}$, OR$^{62}$, SR$^{62}$, S(O)R$^{62}$, SO$_2$R$^{62}$, C(O)R$^{62}$, C(O)OR$^{62}$, OC(O)R$^{62}$, OC(O)OR$^{62}$, NH$_2$, NHR$^{62}$, N(R$^{62}$)$_2$, NHC(O)R$^{62}$, NR$^{62}$C(O)R$^{62}$, NHS(O)$_2$ R$^{62}$, NR$^{62}$S(O)$_2$R$^{62}$, NHC(O)OR$^{62}$, NR$^{62}$C(O)OR$^{62}$, NHC(O)NH$_2$, NHC(O)NHR$^{62}$, NHC(O)N(R$^{62}$)$_2$, NR$^{62}$C(O)NHR$^{62}$, NR$^{62}$C(O)N(R$^{62}$)$_2$, C(O)NH$_2$, C(O)NHR$^{62}$, C(O)N(R$^{62}$)$_2$, C(O)NHOH, C(O)NHOR$^{62}$, C(O)NHSO$_2$R$^{62}$, C(O)NR$^{62}$SO$_2$R$^{62}$, SO$_2$NH$_2$, SO$_2$NHR$^{62}$, SO$_2$N(R$^{62}$)$_2$, C(O)H, C(O)OH, C(N)NH$_2$, C(N)NHR$^{62}$, C(N)N(R$^{62}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{62}$ is R$^{63}$, R$^{64}$, R$^{65}$ or R$^{66}$;

R$^{63}$ is phenyl, which is unfused or fused with benzene, heteroarene or R$^{63A}$; R$^{63A}$ is cycloalkane, cycloalkene, heterocycloalkane or heterocycloalkene;

R$^{64}$ is heteroaryl, which is unfused or fused with benzene, heteroarene or R$^{64A}$; R$^{64A}$ is cycloalkane, cycloalkene, heterocycloalkane or heterocycloalkene;

R$^{65}$ is cycloalkyl, cycloalkenyl, heterocycloalkyl or heterocycloalkenyl, each of which is unfused or fused with benzene, heteroarene or R$^{65A}$; R$^{65A}$ is cycloalkane, cycloalkene, heterocycloalkane or heterocycloalkene;

R$^{66}$ is alkyl, alkenyl, or alkynyl, each of which is unsubstituted or substituted with one or two or three independently selected R$^{67}$, OR$^{67}$, SR$^{67}$, S(O)R$^{67}$, SO$_2$R$^{67}$, C(O)R$^{67}$, C(O)OR$^{67}$, OC(O)R$^{67}$, OC(O)OR$^{67}$, NH$_2$, NHR$^{67}$, N(R$^{67}$)$_2$, NHC(O)R$^{67}$, NR$^{67}$C(O)R$^{67}$, NHS(O)$^2$ R$^{67}$, NR$^{67}$S(O)$_2$R$^{67}$, NHC(O)OR$^{67}$, NR$^{67}$C(O)OR$^{67}$, NHC(O)NH$_2$, NHC(O)NHR$^{67}$, NHC(O)N(R$^{67}$)$_2$, NR$^{67}$C(O)NHR$^{67}$, NR$^{67}$C(O)N(R$^{67}$)$_2$, C(O)NH$_2$, C(O)NHR$^{67}$, C(O)N(R$^{67}$)$_2$, C(O)NHOH, C(O)NHOR$^{67}$, C(O)NHSO$_2$R$^{67}$, C(O)NR$^{67}$SO$_2$R$^{67}$, SO$_2$NH$_2$, SO$_2$NHR$^{67}$, SO$_2$N(R$^{67}$)$_2$, C(O)H, C(O)OH, C(N)NH$_2$, C(N)NHR$^{67}$, C(N)N(R$^{67}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{67}$ is alkyl, alkenyl, alkynyl, phenyl, heteroaryl, cycloalkyl, cycloalkenyl, heterocycloalkyl or heterocycloalkenyl;

wherein the moieties represented by R$^{58}$, R$^{59}$, R$^{60}$, R$^{63}$, R$^{64}$, R$^{65}$, and R$^{67}$ are unsubstituted or substituted with one or more independently selected R$^{68}$, OR$^{68}$, SR$^{68}$, S(O)R$^{68}$, SO$_2$R$^{68}$, C(O)R$^{68}$, C(O)OR$^{68}$, OC(O)R$^{68}$, OC(O)OR$^{68}$, NH$_2$, NHR$^{68}$, N(R$^{68}$)$_2$, NHC(O)R$^{68}$, NR$^{68}$C(O)R$^{68}$, NHS(O)$_2$R$^{68}$, NR$^{68}$S(O)$_2$R$^{68}$, NHC(O)OR$^{68}$, NR$^{68}$C(O)OR$^{68}$, NHC(O)NH$_2$, NHC(O)NHR$^{68}$, NHC(O)N(R$^{68}$)$_2$, NR$^{68}$C(O)NHR$^{68}$, NR$^{68}$C(O)N(R$^{68}$)$_2$, C(O)NH$_2$, C(O)NHR$^{68}$, C(O)N(R$^{68}$)$_2$, C(O)NHOH, C(O)NHOR$^{68}$, C(O)NHSO$_2$R$^{68}$, C(O)NR$^{68}$SO$_2$R$^{68}$, SO$_2$NH$_2$, SO$_2$NHR$^{68}$, SO$_2$N(R$^{68}$)$_2$, C(O)H, C(O)OH, C(N)NH$_2$, C(N)NHR$^{68}$, C(N)N(R$^{68}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{68}$ is R$^{69}$, R$^{70}$, R$^{71}$ or R$^{72}$;

R$^{69}$ is phenyl, which is unfused or fused with benzene, heteroarene or R$^{69A}$; R$^{69A}$ is cycloalkane, cycloalkene, heterocycloalkane or heterocycloalkene;

R$^{70}$ is heteroaryl, which is unfused or fused with benzene, heteroarene or R$^{70A}$; R$^{70A}$ is cycloalkane, cycloalkene, heterocycloalkane or heterocycloalkene;

R$^{71}$ is cycloalkyl, cycloalkenyl, heterocycloalkyl or heterocycloalkenyl, each of which is unfused or fused with benzene, heteroarene or R$^{71A}$; R$^{71A}$ is cycloalkane, cycloalkene, heterocycloalkane or heterocycloalkene;

R$^{72}$ is alkyl, alkenyl, or alkynyl, each of which is unsubstituted or substituted with one or two or three independently selected R$^{73}$, OR$^{73}$, SR$^{73}$, S(O)R$^{73}$, SO$_2$R$^{73}$, C(O)R$^{73}$, C(O)OR$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$ R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)N(R$^{73}$)$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO$_2$NH$_2$, SO$_2$NHR$^{73}$, SO$_2$N(R$^{73}$)$_2$, C(O)H, C(O)OH, C(N)NH$_2$, C(N)NHR$^{73}$, C(N)N(R$^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{73}$ is alkyl, alkenyl, alkenyl, phenyl, heteroaryl, cycloalkyl, cycloalkenyl, heterocycloalkyl, or heterocycloalkenyl; and the moieties represented by R$^{69}$, R$^{70}$, and R$^{71}$ are unsubstituted or substituted with one or more independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, OCF$_3$, OCF$_2$CF$_3$, F, Cl, Br or substituents.

4. A compound or a therapeutically acceptable salt thereof, wherein the compound is chosen from:

tert-butyl (2S)-2-{[(5-{[4-(4-[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-4-methyl-1,3-thiazol-2-yl)oxy]methyl}morpholine-4-carboxylate;

tert-butyl (2S)-2-{[(5-{[2-(1H-benzimidazol-4-yloxy)-4-(4-{[2-(4-chlorophenyl)-4,4-dimethylcyclohex-1-en-1-yl]methyl}piperazin-1-yl)benzoyl]sulfamoyl}-4-methyl-1,3-thiazol-2-yl)oxy]methyl}morpholine-4-carboxylate;

4-(4-{[2-(4-chlorophenyl)-4,4-dimethylcyclohex-1-en-1-yl]methyl}piperazin-1-yl)-N-({2[(4-fluorotetrahydro-2H-pyran-4-yl)methoxy]-4-methyl-1,3-thiazol-5-yl}sulfonyl)-2-(1H-pyrrolo[2,3-b]pyridin-5-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)benzamide;

tert-butyl (2S)-2-{[(5-{[4-(4-{[2-(4-chlorophenyl)-4,4-dimethylcyclohex-1-en-1-yl]methyl}piperazin-1-yl)-2-(1H-indazol-4-yloxy)benzoyl]sulfamoyl}-4-methyl-1,3-thiazol-2-yl)oxy]methyl}morpholine-4-carboxylate; and 4-(4-{[2-(4-chlorophenyl)-4,4-dimethylcyclohex-1-en-1-yl]methyl}piperazin-1-yl)-N-(2-[(4-fluorotetrahydro-2H-pyran-4-yl)methoxy]-4-methyl-1,3-thiazol-5-yl}sulfonyl)-2-(1H-indazol-4-yloxy)benzamide.

5. A composition comprising an excipient and a therapeutically effective amount of the compound of claim 1, or therapeutically acceptable salt thereof.

6. 4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-pyrrolo[2,3-b]pyridin-5-yloxy)benzamide or a therapeutically acceptable salt thereof.

* * * * *

UNITED STATES PATENT AND TRADEMARK OFFICE
CERTIFICATE OF CORRECTION

PATENT NO. : 8,338,466 B2
APPLICATION NO. : 12/689133
DATED : December 25, 2012
INVENTOR(S) : Kunzer et al.

It is certified that error appears in the above-identified patent and that said Letters Patent is hereby corrected as shown below:

In the Claims

Column 113, line 44, claim 1: "heterocycloalkene" to read as --heterocycloalkane-- (1st occurrence)

Column 119, line 10, claim 3: "$NC(R^{6A})(R^{6B})R^7$," to read as --$NC(R^{6A})(R^{6B}), R^7$,--

Column 119, line 14, claim 3: "$NHC(O)CH(C_{1-3})$" to read as --$NHC(O)CH(CH_3)$--

Column 119, line 40, claim 3: "$NHC(O)_{NHR}{}^{12}$," to read as --$NHC(O)NHR^{12}$,--

Column 119, line 41, claim 3: "$NR^{12}C(O)_{NHR}{}^{12}$," to read as --$NR^{12}C(O)NHR^{12}$,--

Column 120, line 20, claim 3: "K" to read as --$R^{46}$--

Column 121, line 7, claim 3: "$R^{1A}, R^2, R^3$," to read as --$R^{1A}, R^2, R^3, R^4, R^8, R^9, R^{10}, R^{13}$,--

Column 122, line 41, claim 3: "$C(O)N(R^{73})_2$," to read as --$C(O)NH_2$,--

Column 122, line 55, claim 3: "Br or substituents." to read as --Br or I substituents.--

Column 124, line 2, claim 4: "N-(2" to read as --N-({2--

Signed and Sealed this
Sixth Day of May, 2014

Michelle K. Lee
*Deputy Director of the United States Patent and Trademark Office*

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: F-Bak Probe Peptide
<220> FEATURE:
<221> NAME/KEY: MOD_RES
<222> LOCATION: 1
<223> OTHER INFORMATION: Gly is modified with acetyl
<220> FEATURE:
<221> NAME/KEY: MOD_RES
```

```
<222> LOCATION: 13
<223> OTHER INFORMATION: Lys is modified with 6-FAM
<220> FEATURE:
<221> NAME/KEY: MOD_RES
<222> LOCATION: 16
<223> OTHER INFORMATION: Arg is modified with NH2

<400> SEQUENCE: 1

Gly Gln Val Gly Arg Gln Leu Ala Ile Ile Gly Asp Lys Ile Asn Arg
1               5                   10                  15
```